(12) United States Patent
Bissantz et al.

(10) Patent No.: US 9,067,943 B2
(45) Date of Patent: Jun. 30, 2015

(54) [1,2,3]TRIAZOLO[4,5-D]PYRIMIDINE DERIVATIVES

(71) Applicant: Hoffmann-La Roche Inc., Nutley, NJ (US)

(72) Inventors: Caterina Bissantz, Village-Neuf (FR); Uwe Grether, Efringen-Kirchen (DE); Atsushi Kimbara, Tokyo (JP); Matthias Nettekoven, Grenzach-Wyhlen (DE); Stephan Roever, Inzlingen (DE); Mark Rogers-Evans, Bottmingen (CH)

(73) Assignee: HOFFMANN-LA ROCHE INC., Nutley, NJ (US)

( * ) Notice: Subject to any disclaimer, the term of this patent is extended or adjusted under 35 U.S.C. 154(b) by 0 days.

(21) Appl. No.: 13/680,143

(22) Filed: Nov. 19, 2012

(65) Prior Publication Data

US 2013/0137676 A1 May 30, 2013

(30) Foreign Application Priority Data

Nov. 25, 2011 (EP) .................................... 11190777

(51) Int. Cl.
| | | |
|---|---|---|
| C07D 413/00 | (2006.01) |
| C07D 487/04 | (2006.01) |
| A61K 9/00 | (2006.01) |
| A61K 47/10 | (2006.01) |
| A61K 47/12 | (2006.01) |
| A61K 9/20 | (2006.01) |
| A61K 9/48 | (2006.01) |
| A61P 9/10 | (2006.01) |
| A61P 3/10 | (2006.01) |
| A61P 27/06 | (2006.01) |
| A61P 29/00 | (2006.01) |
| A61P 1/16 | (2006.01) |
| A61P 13/12 | (2006.01) |
| A61P 9/02 | (2006.01) |

(52) U.S. Cl.
CPC ............ *C07D 487/04* (2013.01); *A61K 9/0019* (2013.01); *A61K 47/10* (2013.01); *A61K 47/12* (2013.01); *A61K 9/2018* (2013.01); *A61K 9/2027* (2013.01); *A61K 9/2054* (2013.01); *A61K 9/2059* (2013.01); *A61K 9/4858* (2013.01)

(58) Field of Classification Search
USPC ................................ 514/261.1; 544/254, 118
See application file for complete search history.

(56) References Cited

U.S. PATENT DOCUMENTS

| | | | |
|---|---|---|---|
| 2,543,333 A * | 2/1951 | Parker et al. .................. 544/254 |
| 4,157,443 A * | 6/1979 | Fletcher ........................ 544/254 |
| 7,750,556 B2 * | 7/2010 | Gessner et al. ................ 313/504 |

| | | | |
|---|---|---|---|
| 2003/0139427 A1 | 7/2003 | Castelhano et al. |
| 2004/0214837 A1 | 10/2004 | Griffith et al. |
| 2004/0214838 A1 | 10/2004 | Carpino et al. |
| 2011/0245255 A1 | 10/2011 | Sanderson et al. |

FOREIGN PATENT DOCUMENTS

| | | |
|---|---|---|
| EP | 2070927 | 6/2009 |
| WO | 2005/061505 | 7/2005 |
| WO | 2005093007 | * 10/2005 |
| WO | 2006/047516 | 5/2006 |
| WO | 2009/059264 | 7/2009 |
| WO | 2011/123482 | 6/2011 |

OTHER PUBLICATIONS

Albert, J. Chem. Soc., Perkin Transactions 1: Org. & Bio-Org. Chem. (1972-1999) (1972), (4), 449-56.*
Timmis, et al., J. Pharmacy & Pharmacol. (1957), 9, 46-67.*
McAllister et al., "An Aromatic microdomain at the cannabinoid CB1 receptor constitutes anagonist/inverse agonist binding region," Journal of Medicinal Chemistry, vol. 46, No. 24, 2003, 5139-5152.
The English translation of the letter of opposition in the corresponding Costa Rican Application No. 2014-0222, which was notified by the Costa Rican Patent Office on Oct. 10, 2014.
Bai et al., "MBC 94, a Conjugable Ligand for Cannabinoid CB2 Receptor Imaging," Bioconjugate Chemistry,vol. 19, No. 5, 2008, 988-992.
Defer et al., The FASEB Journal 23:2120-2130 ( 2009).
Julien et al., Gastroenterology 128:742-755 ( 2005).
Mallat et al., Expert Opin. Ther. Targets 11(3):403-409 ( 2007).
Beltramo et al., Mini-Reviews in Medicinal Chemistry 9:11-25 ( 2009).
Lotersztajn et al., Gastroenterol Clin Biol 31:255-258 ( 2007).
Garcia-Gonzalez et al., Rheumatology 48:1050-1056 ( 2009).
International Search Report for PCT/EP2012/073315 dated Jan. 3, 2013.
Lotersztajn et al., British Journal of Pharmacology 153:286-289 ( 2008).
Akhmetshina et al., Arthritis & Rheumatism 60(4):1129-1136 ( 2009).

(Continued)

*Primary Examiner* — James O Wilson
*Assistant Examiner* — Oluwafemi Masha

(57) ABSTRACT

The invention relates to a compound of formula (I)

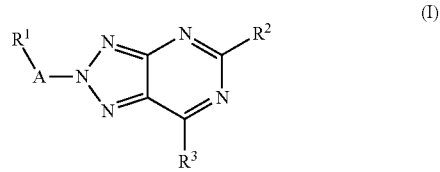

wherein A and $R^1$ to $R^3$ are defined as in the description and in the claims. The compound of formula (I) can be used as a medicament.

13 Claims, No Drawings

(56) References Cited

OTHER PUBLICATIONS

Cabral et al., Journal of Leukocyte Biology 78:1192-1197 (2005).
Munoz-Luque et al., The Journal of Pharmacology and Experimental Therapeutics 324(2):475-483 (2008).
Zhang et al., Journal of Cerebral Blood Flow & Metabolism 27:1387-1396 (2007).
Pacher et al., British Journal of Pharmacology 153:252-262 (2008).
Batkai et al., FASEB Journal 21:1788-1800 (2007).
Mach et al., Journal of Neuroendocrinology 20(Suppl 1):53-57 (2008).
Feizi et al., Experimental and Toxicologic Pathology 60:405-410 (2008).
Yang et al., Liver International 29(5):678-685 (2009).
Bab et al., British Journal of Pharmacology 153:182-188 (2008).
The Summary of the Colombian Office Action, issued on Jan. 27, 2015, in the related Colombian patent application No. 14-068.511.

* cited by examiner

[1,2,3]TRIAZOLO[4,5-D]PYRIMIDINE DERIVATIVES

PRIORITY TO RELATED APPLICATION(S)

This application claims the benefit of European Patent Application No. 11190777.0, filed Nov. 25, 2011, which is hereby incorporated by reference in its entirety.

FIELD OF THE INVENTION

The present invention relates to organic compounds useful for therapy and/or prophylaxis in a mammal, and in particular to compounds that are preferential agonists of the Cannabinoid Receptor 2. The compound of formula (I) is particularly useful in the treatment or prophylaxis of e.g. pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis.

BACKGROUND OF THE INVENTION

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor agonists has been steadily on the rise during the last decade (currently 30-40 patent applications/year) due to the fact that several of the early compounds have been shown to have beneficial effects in preclinical models for a number of human diseases including chronic pain (Beltramo, M. Mini Rev Med Chem 2009, 9(1), 11-25), atherosclerosis (Mach, F. et al. J Neuroendocrinol 2008, 20 Suppl 1, 53-7), regulation of bone mass (Bab, I. et al. Br J Pharmacol 2008, 153(2), 182-8), neuroinflammation (Cabral, G. A. et al. J Leukoc Biol 2005, 78(6), 1192-7), ischemia/reperfusion injury (Pacher, P. et al. Br J Pharmacol 2008, 153(2), 252-62), systemic fibrosis (Akhmetshina, A. et al. Arthritis Rheum 2009, 60(4), 1129-36; Garcia-Gonzalez, E. et al. Rheumatology (Oxford) 2009, 48(9), 1050-6), liver fibrosis (Julien, B. et al. Gastroenterology 2005, 128(3), 742-55; Munoz-Luque, J. et al. J Pharmacol Exp Ther 2008, 324(2), 475-83).

Ischemia/reperfusion (I/R) injury is the principal cause of tissue damage occurring in conditions such as stroke, myocardial infarction, cardiopulmonary bypass and other vascular surgeries, and organ transplantation, as well as a major mechanism of end-organ damage complicating the course of circulatory shock of various etiologies. All these conditions are characterized by a disruption of normal blood supply resulting in an insufficient tissue oxygenation. Re-oxygenation e.g., reperfusion is the ultimate treatment to restore normal tissue oxygenation. However the absence of oxygen and nutrients from blood creates a condition in which the restoration of circulation results in further tissue damage. The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane.

Remote ischemic preconditioning (RIPC) represents a strategy for harnessing the body's endogenous protective capabilities against the injury incurred by ischemia and reperfusion. It describes the intriguing phenomenon in which transient non-lethal ischemia and reperfusion of one organ or tissue confers resistance to a subsequent episode of "lethal" ischemia reperfusion injury in a remote organ or tissue. The actual mechanism through which transient ischemia and reperfusion of an organ or tissue confers protection is currently unknown although several hypotheses have been proposed.

The humoral hypothesis proposes that the endogenous substance (such as adenosine, bradykinin, opioids, CGRP, endocannabinoids, Angiotensin I or some other as yet unidentified humoral factor) generated in the remote organ or tissue enters the blood stream and activates its respective receptor in the target tissue and thereby recruiting the various intracellular pathways of cardioprotection implicated in ischemic preconditioning.

Recent data indicates that endocannabinnoids and their receptors, in particular CB2 might be involved in pre-conditioning and contribute to prevent reperfusion injury by down-regulation of the inflammatory response (Pacher, P. et al. Br J Pharmacol 2008, 153(2), 252-62). Specifically, recent studies using CB2 tool agonists demonstrated the efficacy of this concept for reducing the I/R injury in the heart (Defer, N. et al. Faseb J 2009, 23(7), 2120-30), the brain (Zhang, M. et al. J Cereb Blood Flow Metab 2007, 27(7), 1387-96), the liver (Batkai, S. et al. Faseb J 2007, 21(8), 1788-800) and the kidney (Feizi, A. et al. Exp Toxicol Pathol 2008, 60(4-5), 405-10).

Moreover, over the last few years, a growing body of literature indicates that CB2 can also be of interest in sub-chronic and chronic setting. Specific upregulation of CB1 and CB2 has been shown to be associated in animal models of chronic diseases associated with fibrosis (Garcia-Gonzalez, E. et al. Rheumatology (Oxford) 2009, 48(9), 1050-6; Yang, Y. Y. et al. Liver Int 2009, 29(5), 678-85) with a relevant expression of CB2 in myofibroblasts, the cells responsible for fibrosis progression.

Activation of CB2 receptor by selective CB2 agonist has in fact been shown to exert anti-fibrotic effect in diffuse systemic sclerosis (Garcia-Gonzalez, E. et al. Rheumatology (Oxford) 2009, 48(9), 1050-6) and CB2 receptor has emerged as a critical target in experimental dermal fibrosis (Akhmetshina, A. et al. Arthritis Rheum 2009, 60(4), 1129-36) and in in liver pathophysiology, including fibrogenesis associated with chronic liver diseases (Lotersztajn, S. et al. Gastroenterol Clin Biol 2007, 31(3), 255-8; Mallat, A. et al. Expert Opin Ther Targets 2007, 11(3), 403-9; Lotersztajn, S. et al. Br J Pharmacol 2008, 153(2), 286-9).

The compounds of the invention bind to and modulate the CB2 receptor and have lower CB1 receptor activity.

SUMMARY OF THE INVENTION

The present invention relates in part to a compound of formula (I)

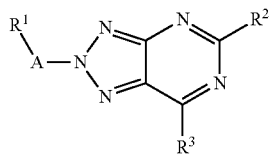

wherein

A is selected from the group consisting of alkylene, hydroxyalkylene, —CH$_2$C(O)—, —C(O)—, —SO$_2$— and a bond;

R$^1$ is selected from the group consisting of hydrogen, alkyl, haloalkyl, hydroxyl, alkoxy, haloalkoxy, phenyl, halophenyl, alkoxyphenyl, haloalkylphenyl, haloalkoxyphenyl, cyanophenyl, hydroxyalkoxyphenyl, alkylsulfonylphenyl, alkylsulfonylaminophenyl, (halo)(haloalkyl)phenyl, (halo)(alkoxy)phenyl, cyano, cycloalkyl, cycloalkylalkoxy, amino, heterocyclyl, alkylheterocyclyl, hydroxyheterocyclyl, alkylheterocyclyl, heteroaryl, haloheteroaryl, alkylheteroaryl, (alkyl)(alkylsulfonyl)heteroaryl, (halo)(alkylamino)heteroaryl, haloalkylheteroaryl, cycloalkylheteroaryl and nitrobenzo[1,2,5]oxadiazolylaminoheteroaryl, wherein said heterocyclyl is a three to eight membered carbocyclic ring comprising at least one nitrogen or oxygen atom and said heteroaryl is selected from the group consisting of pyridinyl, pyrazolyl, oxadiazolyl, furazanyl, tetrazolyl, triazolyl and oxypyridinyl;

R$^2$ is selected from the group consisting of alkyl, haloalkyl, hydroxyalkyl, alkoxyalkyl, cycloalkoxyalkyl, cycloalkylalkoxy, haloalkoxy, alkoxy and alkylamino;

R$^3$ is halogen or —NR$^4$R$^5$; and one of R$^4$ and R$^5$ is hydrogen or alkyl and the other one is alkyl or cycloalkyl;

or R$^4$ and R$^5$ together with the nitrogen atom to which they are attached form heterocyclyl or substituted heterocyclyl, wherein said heterocyclyl is selected from the group consisting of morpholinyl, piperidinyl, piperazinyl, pyrrolidinyl, 2-oxa-6-azaspiro[3.3]heptyl, azetidinyl, thiazolidinyl, thiomorpholinyl, dioxothiomorpholinyl, oxazepanyl, 2-oxa-6-azaspiro[3.4]octyl, 6-oxa-1-azaspiro[3.3]heptyl, 2-oxa-5-aza-spiro[3.4]octyl, isoxazolidinyl, aziridinyl and dioxoisothiazolidinyl and said substituted heterocyclyl is heterocyclyl substituted with one to four substituents independently selected from the group consisting of alkyl, halogen, hydroxyl, alkoxy, hydroxyalkyl, carboxyl, alkoxyalkyl, cyano and alkylcarbonylamino.

The present invention also relates to pharmaceutically acceptable salts or esters of the aforementioned compound.

DETAILED DESCRIPTION OF THE INVENTION

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C$_1$-C$_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl more particularly methyl, ethyl, propyl, isopropyl, isobutyl, tert.-butyl and isopentyl. Particular examples of alkyl are methyl, ethyl and tert.-butyl.

In the present description the term "alkylene", alone or in combination, signifies a straight-chain or branched-chain alkylene group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C$_1$-C$_8$ alkylene groups are methylene or ethylene, more particularly —CH$_2$—, —CH$_2$CH$_2$— or —CH(CH$_3$)—.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. A particular example of cycloalkyl is cyclohexyl or cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy, particularly methoxy.

The term "oxy", alone or in combination, signifies the —O— group.

The term "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens. Particular halogens are fluorine, bromine and chlorine, more particularly fluorine and chlorine.

The term "haloalkyl", alone or in combination, denotes an alkyl group substituted with at least one halogen, particularly substituted with one to five halogens, particularly one to three halogens. A particular "haloalkyl" is trifluoromethyl.

The term "haloalkoxy", alone or in combination, denotes an alkoxy group substituted with at least one halogen, particularly substituted with one to five halogens, particularly one to three halogens. A particular "haloalkoxy" is trifluoromethoxy.

The term "halophenyl", alone or in combination, denotes a phenyl group substituted with at least one halogen, particularly substituted with one to three halogens. Particular "halophenyl" are chlorophenyl, chlorofluorophenyl, dichlorophenyl, bromophenyl and chlorodifluorophenyl.

The terms "hydroxyl" and "hydroxy", alone or in combination, signify the —OH group.

The term "carbonyl", alone or in combination, signifies the —C(O)— group.

The term "carboxyl" or "carboxy", alone or in combination, signifies the —COOH group.

The term "amino", alone or in combination, signifies the primary amino group (—NH$_2$), the secondary amino group (—NH—), or the tertiary amino group (—N—).

The term "sulfonyl", alone or in combination, signifies the —SO$_2$— group.

Particular heterocyclyl groups in the definition of R$^1$ are oxetanyl, tetrahydrofuranyl, 1,1-dioxo-1λ$^6$-thietanyl and 1,1-dioxo-tetrahydro-1λ$^6$-thiophenyl.

Particular halopyrrolidinyl in the definition of $R^3$ and $R^4$ are difluoropyrrolidinyl and tetrafluoropyrrolidinyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, $3^{rd}$ Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The present invention relates in part to a compound of formula (I)

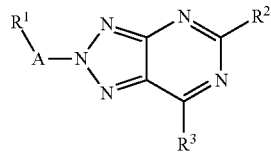

wherein

A is selected from the group consisting of alkylene, hydroxyalkylene, —$CH_2C(O)$—, —$C(O)$—, —$SO_2$— and a bond;

$R^1$ is selected from the group consisting of hydrogen, alkyl, haloalkyl, hydroxyl, alkoxy, haloalkoxy, phenyl, halophenyl, alkoxyphenyl, haloalkylphenyl, haloalkoxyphenyl, cyanophenyl, hydroxyalkoxyphenyl, alkylsulfonylphenyl, alkylsulfonylaminophenyl, (halo)(haloalkyl)phenyl, (halo)(alkoxy)phenyl, cyano, cycloalkyl, cycloalkylalkoxy, amino, heterocyclyl, alkylheterocyclyl, hydroxyheterocyclyl, alkylheterocyclyl, heteroaryl, haloheteroaryl, alkylheteroaryl, (alkyl)(alkylsulfonyl)heteroaryl, (halo)(alkylamino)heteroaryl, haloalkylheteroaryl, cycloalkylheteroaryl and nitrobenzo[1,2,5]oxadiazolylaminoheteroaryl, wherein said heterocyclyl is a three to eight membered carbocyclic ring comprising at least one nitrogen or oxygen atom and said heteroaryl is selected from the group consisting of pyridinyl, pyrazolyl, oxadiazolyl, furazanyl, tetrazolyl, triazolyl and oxypyridinyl;

$R^2$ is selected from the group consisting of alkyl, haloalkyl, hydroxyalkyl, alkoxyalkyl, cycloalkoxyalkyl, cycloalkylalkoxy, haloalkoxy, alkoxy and alkylamino;

$R^3$ is halogen or —$NR^4R^5$; and one of $R^4$ and $R^5$ is hydrogen or alkyl and the other one is alkyl or cycloalkyl; or $R^4$ and $R^5$ together with the nitrogen atom to which they are attached form heterocyclyl or substituted heterocyclyl, wherein said heterocyclyl is selected from the group consisting of morpholinyl, piperidinyl, piperazinyl, pyrrolidinyl, 2-oxa-6-azaspiro[3.3]heptyl, azetidinyl, thiazolidinyl, thiomorpholinyl, dioxothiomorpholinyl, oxazepanyl, 2-oxa-6-azaspiro[3.4]octyl, 6-oxa-1-azaspiro[3.3]heptyl, 2-oxa-5-aza-spiro[3.4]octyl, isoxazolidinyl, aziridinyl and dioxoisothiazolidinyl and said substituted heterocyclyl is heterocyclyl substituted with one to four substituents independently selected from the group consisting of alkyl, halogen, hydroxyl, alkoxy, hydroxyalkyl, carboxyl, alkoxyalkyl, cyano and alkylcarbonylamino.

The present invention also relates to pharmaceutically acceptable salts or esters of the aforementioned compound.

The invention relates in particular to a compound of formula (I) wherein

A is selected from the group consisting of alkylene, hydroxyalkylene, —$CH_2C(O)$—, —$C(O)$—, —$SO_2$— and a bond;

$R^1$ is selected from the group consisting of hydrogen, alkyl, haloalkyl, hydroxyl, alkoxy, haloalkoxy, phenyl, halophenyl, alkoxyphenyl, haloalkylphenyl, haloalkoxyphenyl, cyanophenyl, hydroxyalkoxyphenyl, alkylsulfonylphenyl, alkylsulfonylaminophenyl, cyano, cycloalkyl, cycloalkylalkoxy, amino, heterocyclyl, alkylheterocyclyl, hydroxyheterocyclyl, alkylheterocyclyl, heteroaryl and haloheteroaryl, wherein said heterocyclyl is a three to eight membered carbocyclic ring comprising at least one nitrogen or oxygen atom and said heteroaryl is selected from the group consisting of pyridinyl, pyrazolyl, oxadiazolyl and furazanyl;

R² is selected from the group consisting of alkyl, haloalkyl, hydroxyalkyl, alkoxyalkyl, cycloalkoxyalkyl and cycloalkylalkoxy;

R³ is halogen or —NR⁴R⁵; and one of R⁴ and R⁵ is hydrogen or alkyl and the other one is alkyl or cycloalkyl;

or R⁴ and R⁵ together with the nitrogen atom to which they are attached form heterocyclyl or substituted heterocyclyl, wherein said heterocyclyl is selected from the group consisting of morpholinyl, piperidinyl, piperazinyl, pyrrolidinyl, 2-oxa-6-azaspiro[3.3]heptyl, azetidinyl, thiazolidinyl, thiomorpholinyl, dioxothiomorpholinyl, oxazepanyl, 2-oxa-6-azaspiro[3.4]octyl, 6-oxa-1-azaspiro[3.3]heptyl, 2-oxa-5-aza-spiro[3.4]octyl, isoxazolidinyl, aziridinyl and dioxoisothiazolidinyl and said substituted heterocyclyl is heterocyclyl substituted with one to four substituents independently selected from the group consisting of alkyl, halogen, hydroxyl, alkoxy, hydroxyalkyl, carboxyl, alkoxyalkyl and cyano;

or a pharmaceutically acceptable salt or ester thereof.

Additional embodiments of the present invention the following:

A compound of formula (I) wherein A is selected from the group consisting of alkylene, —CH₂C(O)— and a bond;

A compound of formula (I) wherein A is alkylene;

A compound of formula (I) wherein A is selected from the group consisting of methylene, ethylene and —CH(CH₃)—;

A compound of formula (I) wherein R¹ is selected from the group consisting of hydrogen, alkyl, haloalkyl, hydroxyl, alkoxy, haloalkoxy, phenyl, halophenyl, alkoxyphenyl, haloalkylphenyl, haloalkoxyphenyl, cyanophenyl, hydroxyalkoxyphenyl, alkylsulfonylphenyl, alkylsulfonylaminophenyl, cyano, cycloalkyl, cycloalkylalkoxy, amino, heterocyclyl, alkylheterocyclyl, hydroxyheterocyclyl, alkylheterocyclyl, heteroaryl and haloheteroaryl, wherein said heterocyclyl is a three to eight membered carbocyclic ring comprising at least one nitrogen or oxygen atom and said heteroaryl is selected from the group consisting of pyridinyl, pyrazolyl, oxadiazolyl and furazanyl;

A compound of formula (I) wherein R¹ is selected from the group consisting of hydrogen, alkyl, haloalkyl, hydroxyl, alkoxy, phenyl, halophenyl, alkoxyphenyl, haloalkylphenyl, haloalkoxyphenyl, cyanophenyl, cycloalkyl, oxetanyl and pyridinyl;

A compound of formula (I) wherein R¹ is selected from the group consisting of trifluoromethyl, phenyl, chlorophenyl, bromophenyl, cyanophenyl, cyclohexyl and pyridinyl;

A compound of formula (I) wherein R¹ is selected from the group consisting of alkyl, haloalkyl, hydroxyl, alkoxy, phenyl, halophenyl, alkoxyphenyl, haloalkylphenyl, haloalkoxyphenyl, cyanophenyl, cycloalkyl, heterocyclyl, haloheteroaryl and alkylheterocyclyl, wherein said heterocyclyl is oxetanyl and said heteroaryl is pyridinyl or furazanyl;

A compound of formula (I) wherein R¹ is selected from the group consisting of alkyl, haloalkyl, hydroxyl, alkoxy, phenyl, halophenyl, alkoxyphenyl, haloalkylphenyl, haloalkoxyphenyl, cyanophenyl, cycloalkyl, oxetanyl, pyridinyl, halopyridinyl and alkylfurazanyl;

A compound of formula (I) wherein R¹ is selected from the group consisting of trifluoromethyl, phenyl, chlorophenyl, bromophenyl, cyanophenyl, cyclohexyl, pyridinyl, chloropyridinyl, methylfurazanyl and trifluoromethylphenyl;

A compound of formula (I) wherein R² is alkyl;

A compound of formula (I) wherein R² is tert.-butyl;

A compound of formula (I) wherein R³ is —NR⁴R⁵;

A compound of formula (I) wherein R⁴ and R⁵ together with the nitrogen atom to which they are attached form morpholinyl or halopyrrolidinyl;

A compound of formula (I) wherein R⁴ and R⁵ together with the nitrogen atom to which they are attached form morpholinyl or difluoropyrrolidinyl;

A compound of formula (I) wherein R⁴ and R⁵ together with the nitrogen atom to which they are attached form morpholinyl, halopyrrolidinyl or hydroxypyrrolidinyl; and A compound of formula (I) wherein R⁴ and R⁵ together with the nitrogen atom to which they are attached form morpholinyl, difluoropyrrolidinyl or hydroxypyrrolidinyl.

The invention also relates in particular to a compound of formula (I) selected from the group consisting of 5-tert-Butyl-2-(2-chloro-benzyl)-7-morpholin-4-yl-2H-[1,2,3]triazolo[4,5-d]pyrimidine;

5-tert-Butyl-2-(2-chloro-4-fluoro-benzyl)-7-morpholin-4-yl-2H-[1,2,3]triazolo[4,5-d]pyrimidine;

5-tert-Butyl-7-(3,3-difluoro-pyrrolidin-1-yl)-2-ethyl-2H-[1,2,3]triazolo[4,5-d]pyrimidine;

5-tert-Butyl-7-(3,3-difluoro-pyrrolidin-1-yl)-2-(2-methoxy-ethyl)-2H-[1,2,3]triazolo[4,5-d]pyrimidine;

2-[5-tert-Butyl-7-(3,3-difluoro-pyrrolidin-1-yl)-[1,2,3]triazolo[4,5-d]pyrimidin-2-yl]-ethanol;

5-tert-Butyl-2-cyclohexylmethyl-7-(3,3-difluoro-pyrrolidin-1-yl)-2H-[1,2,3]triazolo[4,5-d]pyrimidine;

5-tert-Butyl-2-(3-chloro-benzyl)-7-(3,3-difluoro-pyrrolidin-1-yl)-2H-[1,2,3]triazolo[4,5-d]pyrimidine;

5-tert-Butyl-2-(4-chloro-benzyl)-7-(3,3-difluoro-pyrrolidin-1-yl)-2H-[1,2,3]triazolo[4,5-d]pyrimidine;

5-tert-Butyl-2-(2,3-dichloro-benzyl)-7-(3,3-difluoro-pyrrolidin-1-yl)-2H-[1,2,3]triazolo[4,5-d]pyrimidine;

5-tert-Butyl-2-(2,4-dichloro-benzyl)-7-(3,3-difluoro-pyrrolidin-1-yl)-2H-[1,2,3]triazolo[4,5-d]pyrimidine;

5-tert-Butyl-2-(2,5-dichloro-benzyl)-7-(3,3-difluoro-pyrrolidin-1-yl)-2H-[1,2,3]triazolo[4,5-d]pyrimidine;

5-tert-Butyl-2-(2,6-dichloro-benzyl)-7-(3,3-difluoro-pyrrolidin-1-yl)-2H-[1,2,3]triazolo[4,5-d]pyrimidine;

5-tert-Butyl-2-(2-chloro-4-fluoro-benzyl)-7-(3,3-difluoro-pyrrolidin-1-yl)-2H-[1,2,3]triazolo[4,5-d]pyrimidine;

5-tert-Butyl-2-(2-chloro-6-fluoro-benzyl)-7-(3,3-difluoro-pyrrolidin-1-yl)-2H-[1,2,3]triazolo[4,5-d]pyrimidine;

5-tert-Butyl-7-(3,3-difluoro-pyrrolidin-1-yl)-2-pyridin-2-ylmethyl-2H-[1,2,3]triazolo[4,5-d]pyrimidine;

5-tert-Butyl-7-(3,3-difluoro-pyrrolidin-1-yl)-2-pyridin-3-ylmethyl-2H-[1,2,3]triazolo[4,5-d]pyrimidine;

5-tert-Butyl-7-(3,3-difluoro-pyrrolidin-1-yl)-2-pyridin-4-ylmethyl-2H-[1,2,3]triazolo[4,5-d]pyrimidine;

5-tert-Butyl-7-(3,3-difluoro-pyrrolidin-1-yl)-2-(2,2,2-trifluoro-ethyl)-2H-[1,2,3]triazolo[4,5-d]pyrimidine;

5-tert-Butyl-2-(2-chloro-4,5-difluoro-benzyl)-7-(3,3-difluoro-pyrrolidin-1-yl)-2H-[1,2,3]triazolo[4,5-d]pyrimidine;

5-tert-Butyl-2-(2-chloro-3,6-difluoro-benzyl)-7-(3,3-difluoro-pyrrolidin-1-yl)-2H-[1,2,3]triazolo[4,5-d]pyrimidine;

2-(2-Bromo-benzyl)-5-tert-butyl-7-(3,3-difluoro-pyrrolidin-1-yl)-2H-[1,2,3]triazolo[4,5-d]pyrimidine;

5-tert-Butyl-7-(3,3-difluoro-pyrrolidin-1-yl)-2-(2-trifluoromethyl-benzyl)-2H-[1,2,3]triazolo[4,5-d]pyrimidine;

5-tert-Butyl-7-(3,3-difluoro-pyrrolidin-1-yl)-2-(2-methoxy-benzyl)-2H-[1,2,3]triazolo[4,5-d]pyrimidine;

5-tert-Butyl-7-(3,3-difluoro-pyrrolidin-1-yl)-2-(2-trifluoromethoxy-benzyl)-2H-[1,2,3]triazolo[4,5-d]pyrimidine;

2-[5-tert-Butyl-7-(3,3-difluoro-pyrrolidin-1-yl)-[1,2,3]triazolo[4,5-d]pyrimidin-2-ylmethyl]-benzonitrile;

5-tert-Butyl-7-(3,3-difluoro-pyrrolidin-1-yl)-2-phenethyl-2H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-2-yl]-1-phenyl-ethanone;
5-tert-Butyl-2-[(R)-1-(2-chloro-phenyl)-ethyl]-7-(3,3-difluoro-pyrrolidin-1-yl)-2H-[1,2,3]triazolo[4,5-d]pyrimidine;
5-tert-Butyl-2-[(S)-1-(2-chloro-phenyl)-ethyl]-7-(3,3-difluoro-pyrrolidin-1-yl)-2H-[1,2,3]triazolo[4,5-d]pyrimidine;
5-tert-Butyl-2-(2-chloro-3-fluoro-benzyl)-7-(3,3-difluoro-pyrrolidin-1-yl)-2H-[1,2,3]triazolo[4,5-d]pyrimidine;
5-tert-Butyl-2-(2-chloro-5-fluoro-benzyl)-7-(3,3-difluoro-pyrrolidin-1-yl)-2H-[1,2,3]triazolo[4,5-d]pyrimidine; and
5-tert-Butyl-7-(3,3-difluoro-pyrrolidin-1-yl)-2-oxetan-3-yl-2H-[1,2,3]triazolo[4,5-d]pyrimidine.

The invention also relates in particular to a compound of formula (I) selected from the group consisting of
5-tert-Butyl-2-(2,6-dichloro-3-fluoro-benzyl)-7-(3,3-difluoro-pyrrolidin-1-yl)-2H-[1,2,3]triazolo[4,5-d]pyrimidine;
5-tert-Butyl-2-(2-chloro-pyridin-3-ylmethyl)-7-(3,3-difluoro-pyrrolidin-1-yl)-2H-[1,2,3]triazolo[4,5-d]pyrimidine;
5-tert-Butyl-2-(4-chloro-pyridin-3-ylmethyl)-7-(3,3-difluoro-pyrrolidin-1-yl)-2H-[1,2,3]triazolo[4,5-d]pyrimidine;
5-tert-Butyl-2-(3-chloro-pyridin-2-ylmethyl)-7-(3,3-difluoro-pyrrolidin-1-yl)-2H-[1,2,3]triazolo[4,5-d]pyrimidine;
5-tert-Butyl-2-(2,5-dichloro-pyridin-3-ylmethyl)-7-(3,3-difluoro-pyrrolidin-1-yl)-2H-[1,2,3]triazolo[4,5-d]pyrimidine;
5-tert-Butyl-2-(3,6-dichloro-pyridin-2-ylmethyl)-7-(3,3-difluoro-pyrrolidin-1-yl)-2H-[1,2,3]triazolo[4,5-d]pyrimidine;
5-tert-Butyl-7-(3,3-difluoro-pyrrolidin-1-yl)-2-(4-methyl-furazan-3-ylmethyl)-2H-[1,2,3]triazolo[4,5-d]pyrimidine;
5-tert-Butyl-7-(3,3-difluoro-pyrrolidin-1-yl)-2-(3-methyl-[1,2,4]oxadiazol-5-ylmethyl)-2H-[1,2,3]triazolo[4,5-d]pyrimidine;
5-tert-Butyl-2-[2-(2-chloro-phenyl)-ethyl]-7-(3,3-difluoro-pyrrolidin-1-yl)-2H-[1,2,3]triazolo[4,5-d]pyrimidine;
5-tert-Butyl-2-[2-(3-chloro-phenyl)-ethyl]-7-(3,3-difluoro-pyrrolidin-1-yl)-2H-[1,2,3]triazolo[4,5-d]pyrimidine;
5-tert-Butyl-2-[2-(4-chloro-phenyl)-ethyl]-7-(3,3-difluoro-pyrrolidin-1-yl)-2H-[1,2,3]triazolo[4,5-d]pyrimidine;
5-tert-Butyl-2-(2,4-dichloro-pyridin-3-ylmethyl)-7-(3,3-difluoro-pyrrolidin-1-yl)-2H-[1,2,3]triazolo[4,5-d]pyrimidine;
5-tert-Butyl-7-(3,3-difluoro-pyrrolidin-1-yl)-2-(R)-tetrahydro-furan-3-yl-2H-[1,2,3]triazolo[4,5-d]pyrimidine;
5-tert-Butyl-7-(3,3-difluoro-pyrrolidin-1-yl)-2-(S)-tetrahydro-furan-3-yl-2H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-2-yl]-1-(2-chloro-phenyl)-ethanone;
5-tert-Butyl-2-(2,3-dichloro-6-fluoro-benzyl)-7-(3,3-difluoro-pyrrolidin-1-yl)-2H-[1,2,3]triazolo[4,5-d]pyrimidine;
5-tert-Butyl-7-(3,3-difluoro-pyrrolidin-1-yl)-2-(2-methanesulfonyl-benzyl)-2H-[1,2,3]triazolo[4,5-d]pyrimidine;
5-tert-Butyl-7-(3,3-difluoro-pyrrolidin-1-yl)-2-(2-pyridin-2-yl-ethyl)-2H-[1,2,3]triazolo[4,5-d]pyrimidine;
5-tert-Butyl-7-(3,3-difluoro-pyrrolidin-1-yl)-2-(3-methyl-oxetan-3-ylmethyl)-2H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-2-yl]-1-(3-chloro-phenyl)-ethanone;
2-[5-tert-Butyl-7-(3,3-difluoro-pyrrolidin-1-yl)-[1,2,3]triazolo[4,5-d]pyrimidin-2-yl]-1-(4-chloro-phenyl)-ethanone;
2-[5-tert-Butyl-7-(3,3-difluoro-pyrrolidin-1-yl)-[1,2,3]triazolo[4,5-d]pyrimidin-2-yl]-1-pyridin-3-yl-ethanone;
5-tert-Butyl-7-(3,3-difluoro-pyrrolidin-1-yl)-2-(2,3,6-trichloro-benzyl)-2H-[1,2,3]triazolo[4,5-d]pyrimidine;
5-tert-Butyl-2-(2-chloro-3-trifluoromethyl-benzyl)-7-(3,3-difluoro-pyrrolidin-1-yl)-2H-[1,2,3]triazolo[4,5-d]pyrimidine;
5-tert-Butyl-2-(2-chloro-6-fluoro-3-methoxy-benzyl)-7-(3,3-difluoro-pyrrolidin-1-yl)-2H-[1,2,3]triazolo[4,5-d]pyrimidine;
5-tert-Butyl-7-(3,3-difluoro-pyrrolidin-1-yl)-2-(2-pyridin-3-yl-ethyl)-2H-[1,2,3]triazolo[4,5-d]pyrimidine;
5-tert-Butyl-7-(3,3-difluoro-pyrrolidin-1-yl)-2-(2-pyridin-4-yl-ethyl)-2H-[1,2,3]triazolo[4,5-d]pyrimidine;
5-tert-Butyl-2-(2,3-dichloro-6-trifluoromethyl-benzyl)-7-(3,3-difluoro-pyrrolidin-1-yl)-2H-[1,2,3]triazolo[4,5-d]pyrimidine;
5-tert-Butyl-2-(3,4-dichloro-pyridin-2-ylmethyl)-7-(3,3-difluoro-pyrrolidin-1-yl)-2H-[1,2,3]triazolo[4,5-d]pyrimidine;
5-tert-Butyl-7-(3,3-difluoro-pyrrolidin-1-yl)-2-(1,1-dioxo-1λ6-thietan-3-yl)-2H-[1,2,3]triazolo[4,5-d]pyrimidine;
5-tert-Butyl-7-(3,3-difluoro-pyrrolidin-1-yl)-2-(1,1-dioxo-tetrahydro-1λ6-thiophen-3-yl)-2H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-2-yl]-1-pyridin-2-yl-ethanone;
5-tert-Butyl-7-(3,3-difluoro-pyrrolidin-1-yl)-2-(5-methyl-[1,3,4]oxadiazol-2-ylmethyl)-2H-[1,2,3]triazolo[4,5-d]pyrimidine;
5-tert-Butyl-2-(3-chloro-pyridin-4-ylmethyl)-7-(3,3-difluoro-pyrrolidin-1-yl)-2H-[1,2,3]triazolo[4,5-d]pyrimidine;
5-tert-Butyl-7-(3,3-difluoro-pyrrolidin-1-yl)-2-(5-methyl-[1,2,4]oxadiazol-3-ylmethyl)-2H-[1,2,3]triazolo[4,5-d]pyrimidine;
5-tert-Butyl-7-(3,3-difluoro-pyrrolidin-1-yl)-2-(1-methyl-1H-tetrazol-5-ylmethyl)-2H-[1,2,3]triazolo[4,5-d]pyrimidine;
5-tert-Butyl-7-(3,3-difluoro-pyrrolidin-1-yl)-2-(2-methyl-2H-[1,2,4]triazol-3-ylmethyl)-2H-[1,2,3]triazolo[4,5-d]pyrimidine;
5-tert-Butyl-7-(3,3-difluoro-pyrrolidin-1-yl)-2-(5-methanesulfonyl-4-methyl-4H-[1,2,4]triazol-3-ylmethyl)-2H-[1,2,3]triazolo[4,5-d]pyrimidine;
{3-[5-tert-Butyl-7-(3,3-difluoro-pyrrolidin-1-yl)-[1,2,3]triazolo[4,5-d]pyrimidin-2-ylmethyl]-5-chloro-pyridin-4-yl}-dimethyl-amine;
5-tert-Butyl-7-(3,3-difluoro-pyrrolidin-1-yl)-2-(3-trifluoromethyl-1H-pyrazol-4-ylmethyl)-2H-[1,2,3]triazolo[4,5-d]pyrimidine;
(S)-1-[5-tert-Butyl-2-(4-methyl-furazan-3-ylmethyl)-2H-[1,2,3]triazolo[4,5-d]pyrimidin-7-yl]-pyrrolidin-3-ol;
(S)-1-[5-tert-Butyl-2-(3-methyl-[1,2,4]oxadiazol-5-ylmethyl)-2H-[1,2,3]triazolo[4,5-d]pyrimidin-7-yl]-pyrrolidin-3-ol;
(S)-1-[5-tert-Butyl-2-(3-chloro-pyridin-2-ylmethyl)-2H-[1,2,3]triazolo[4,5-d]pyrimidin-7-yl]-pyrrolidin-3-ol;
(S)-1-[5-tert-Butyl-2-(3,6-dichloro-pyridin-2-ylmethyl)-2H-[1,2,3]triazolo[4,5-d]pyrimidin-7-yl]-pyrrolidin-3-ol;

(S)-1-[5-tert-Butyl-2-(2-chloro-pyridin-3-ylmethyl)-2H-[1,2,3]triazolo[4,5-d]pyrimidin-7-yl]-pyrrolidin-3-ol;
(S)-1-[5-tert-Butyl-2-(2,3-dichloro-benzyl)-2H-[1,2,3]triazolo[4,5-d]pyrimidin-7-yl]-pyrrolidin-3-ol;
(S)-1-[5-tert-Butyl-2-(2-trifluoromethyl-benzyl)-2H-[1,2,3]triazolo[4,5-d]pyrimidin-7-yl]-pyrrolidin-3-ol;
(S)-1-[5-tert-Butyl-2-(2-methanesulfonyl-benzyl)-2H-[1,2,3]triazolo[4,5-d]pyrimidin-7-yl]-pyrrolidin-3-ol;
5-tert-Butyl-7-(3,3-difluoro-pyrrolidin-1-yl)-2-(2,5-dimethyl-2H-pyrazol-3-ylmethyl)-2H-[1,2,3]triazolo[4,5-d]pyrimidine;
5-tert-Butyl-7-(3,3-difluoro-pyrrolidin-1-yl)-2-(3-methyl-3H-[1,2,3]triazol-4-ylmethyl)-2H-[1,2,3]triazolo[4,5-d]pyrimidine;
5-tert-Butyl-7-(3,3-difluoro-pyrrolidin-1-yl)-2-(4,5-dimethyl-4H-[1,2,4]triazol-3-ylmethyl)-2H-[1,2,3]triazolo[4,5-d]pyrimidine;
5-tert-Butyl-7-(3,3-difluoro-pyrrolidin-1-yl)-2-(2-methyl-1-oxy-pyridin-3-ylmethyl)-2H-[1,2,3]triazolo[4,5-d]pyrimidine;
(S)-1-[5-tert-Butyl-2-(3,4-dichloro-pyridin-2-ylmethyl)-2H-[1,2,3]triazolo[4,5-d]pyrimidin-7-yl]-pyrrolidin-3-ol;
(S)-1-[5-tert-Butyl-2-(5-methyl-[1,2,4]oxadiazol-3-ylmethyl)-2H-[1,2,3]triazolo[4,5-d]pyrimidin-7-yl]-pyrrolidin-3-ol;
(S)-1-[5-tert-Butyl-2-(5-methyl-[1,3,4]oxadiazol-2-ylmethyl)-2H-[1,2,3]triazolo[4,5-d]pyrimidin-7-yl]-pyrrolidin-3-ol;
(S)-1-[5-tert-Butyl-2-(1-methyl-1H-tetrazol-5-ylmethyl)-2H-[1,2,3]triazolo[4,5-d]pyrimidin-7-yl]-pyrrolidin-3-ol;
(S)-1-[5-tert-Butyl-2-(2-methyl-2H-[1,2,4]triazol-3-ylmethyl)-2H-[1,2,3]triazolo[4,5-d]pyrimidin-7-yl]-pyrrolidin-3-ol;
(S)-1-[5-tert-Butyl-2-(3-methyl-3H-[1,2,3]triazol-4-ylmethyl)-2H-[1,2,3]triazolo[4,5-d]pyrimidin-7-yl]-pyrrolidin-3-ol;
(S)-1-[5-tert-Butyl-2-(2,5-dimethyl-2H-pyrazol-3-ylmethyl)-2H-[1,2,3]triazolo[4,5-d]pyrimidin-7-yl]-pyrrolidin-3-ol;
5-tert-Butyl-2-(1-cyclopropyl-1H-tetrazol-5-ylmethyl)-7-(3,3-difluoro-pyrrolidin-1-yl)-2H-[1,2,3]triazolo[4,5-d]pyrimidine;
(S)-1-{5-tert-Butyl-2-[2-(7-nitro-benzo[1,2,5]oxadiazol-4-ylamino)-pyridin-3-ylmethyl]-2H-[1,2,3]triazolo[4,5-d]pyrimidin-7-yl}-pyrrolidin-3-ol;
(S)-1-[5-tert-Butyl-2-(1-cyclopropyl-1H-tetrazol-5-ylmethyl)-2H-[1,2,3]triazolo[4,5-d]pyrimidin-7-yl]-pyrrolidin-3-ol;
(S)-1-[5-tert-Butyl-2-(2,5-dimethyl-2H-[1,2,4]triazol-3-ylmethyl)-2H-[1,2,3]triazolo[4,5-d]pyrimidin-7-yl]-pyrrolidin-3-ol;
5-tert-Butyl-7-(3,3-difluoro-pyrrolidin-1-yl)-2-(2,5-dimethyl-2H-[1,2,4]triazol-3-ylmethyl)-2H-[1,2,3]triazolo[4,5-d]pyrimidine;
(2S,3S)-1-[5-tert-Butyl-2-(1-cyclopropyl-1H-tetrazol-5-ylmethyl)-2H-[1,2,3]triazolo[4,5-d]pyrimidin-7-yl]-2-hydroxymethyl-pyrrolidin-3-ol;
(2S,3S)-1-[5-tert-Butyl-2-(4-methyl-furazan-3-ylmethyl)-2H-[1,2,3]triazolo[4,5-d]pyrimidin-7-yl]-2-hydroxymethyl-pyrrolidin-3-ol;
5-tert-Butyl-2-(4-methyl-furazan-3-ylmethyl)-7-(3,3,4,4-tetrafluoro-pyrrolidin-1-yl)-2H-[1,2,3]triazolo[4,5-d]pyrimidine;
5-tert-Butyl-2-(3-methyl-[1,2,4]oxadiazol-5-ylmethyl)-7-(3,3,4,4-tetrafluoro-pyrrolidin-1-yl)-2H-[1,2,3]triazolo[4,5-d]pyrimidine;
5-tert-Butyl-2-(5-methyl-[1,3,4]oxadiazol-2-ylmethyl)-7-(3,3,4,4-tetrafluoro-pyrrolidin-1-yl)-2H-[1,2,3]triazolo[4,5-d]pyrimidine;
5-tert-Butyl-2-(1-methyl-1H-tetrazol-5-ylmethyl)-7-(3,3,4,4-tetrafluoro-pyrrolidin-1-yl)-2H-[1,2,3]triazolo[4,5-d]pyrimidine;
5-tert-Butyl-2-(4,5-dimethyl-4H-[1,2,4]triazol-3-ylmethyl)-7-(3,3,4,4-tetrafluoro-pyrrolidin-1-yl)-2H-[1,2,3]triazolo[4,5-d]pyrimidine;
5-tert-Butyl-2-(3-methyl-3H-[1,2,3]triazol-4-ylmethyl)-7-(3,3,4,4-tetrafluoro-pyrrolidin-1-yl)-2H-[1,2,3]triazolo[4,5-d]pyrimidine;
5-tert-Butyl-2-(1-cyclopropyl-1H-tetrazol-5-ylmethyl)-7-(2-oxa-6-aza-spiro[3.3]hept-6-yl)-2H-[1,2,3]triazolo[4,5-d]pyrimidine;
5-tert-Butyl-2-(4,5-dimethyl-4H-[1,2,4]triazol-3-ylmethyl)-7-(2-oxa-6-aza-spiro[3.3]hept-6-yl)-2H-[1,2,3]triazolo[4,5-d]pyrimidine;
5-tert-Butyl-2-(2-methanesulfonyl-benzyl)-7-(2-oxa-6-aza-spiro[3.3]hept-6-yl)-2H-[1,2,3]triazolo[4,5-d]pyrimidine;
5-tert-Butyl-2-(3-chloro-pyridin-2-ylmethyl)-7-(2-oxa-6-aza-spiro[3.3]hept-6-yl)-2H-[1,2,3]triazolo[4,5-d]pyrimidine;
(S)-1-[2-(2-Chloro-benzyl)-5-(2,2,2-trifluoro-ethoxy)-2H-[1,2,3]triazolo[4,5-d]pyrimidin-7-yl]-pyrrolidin-3-ol;
(S)-1-[5-(2,2,2-Trifluoro-ethoxy)-2-(2-trifluoromethyl-benzyl)-2H-[1,2,3]triazolo[4,5-d]pyrimidin-7-yl]-pyrrolidin-3-ol;
(S)-1-[2-(2-Chloro-benzyl)-5-isopropoxy-2H-[1,2,3]triazolo[4,5-d]pyrimidin-7-yl]-pyrrolidin-3-ol;
7-(3,3-Difluoro-pyrrolidin-1-yl)-5-(2,2-dimethyl-propoxy)-2-(1-methyl-1H-tetrazol-5-ylmethyl)-2H-[1,2,3]triazolo[4,5-d]pyrimidine;
(R)-1-[5-tert-Butyl-2-(1-methyl-1H-tetrazol-5-ylmethyl)-2H-[1,2,3]triazolo[4,5-d]pyrimidin-7-yl]-pyrrolidin-3-ol;
1-[5-tert-Butyl-2-(1-methyl-1H-tetrazol-5-ylmethyl)-2H-[1,2,3]triazolo[4,5-d]pyrimidin-7-yl]-pyrrolidin-3-ol;
7-(3,3-Difluoro-pyrrolidin-1-yl)-2-(2-trifluoromethyl-benzyl)-5-((S)-2,2,2-trifluoro-1-methyl-ethoxy)-2H-[1,2,3]triazolo[4,5-d]pyrimidine;
7-(3,3-Difluoro-pyrrolidin-1-yl)-2-(2-methanesulfonyl-benzyl)-5-((S)-2,2,2-trifluoro-1-methyl-ethoxy)-2H-[1,2,3]triazolo[4,5-d]pyrimidine;
2-(3-Chloro-pyridin-2-ylmethyl)-7-(3,3-difluoro-pyrrolidin-1-yl)-5-((S)-2,2,2-trifluoro-1-methyl-ethoxy)-2H-[1,2,3]triazolo[4,5-d]pyrimidine;
7-(3,3-Difluoro-pyrrolidin-1-yl)-2-(5-methyl-[1,3,4]oxadiazol-2-ylmethyl)-5-((S)-2,2,2-trifluoro-1-methyl-ethoxy)-2H-[1,2,3]triazolo[4,5-d]pyrimidine;
7-(3,3-Difluoro-pyrrolidin-1-yl)-2-(3-methyl-[1,2,4]oxadiazol-5-ylmethyl)-5-((S)-2,2,2-trifluoro-1-methyl-ethoxy)-2H-[1,2,3]triazolo[4,5-d]pyrimidine;
7-(3,3-Difluoro-pyrrolidin-1-yl)-2-(1-methyl-1H-tetrazol-5-ylmethyl)-5-((S)-2,2,2-trifluoro-1-methyl-ethoxy)-2H-[1,2,3]triazolo[4,5-d]pyrimidine;
7-(3,3-Difluoro-pyrrolidin-1-yl)-2-(4-methyl-furazan-3-ylmethyl)-5-((S)-2,2,2-trifluoro-1-methyl-ethoxy)-2H-[1,2,3]triazolo[4,5-d]pyrimidine;
7-(3,3-Difluoro-pyrrolidin-1-yl)-5-((S)-2,2,2-trifluoro-1-methyl-ethoxy)-2-(3,3,3-trifluoro-propyl)-2H-[1,2,3]triazolo[4,5-d]pyrimidine;
2-(1-Cyclopropyl-1H-tetrazol-5-ylmethyl)-7-(3,3-difluoro-pyrrolidin-1-yl)-5-((S)-2,2,2-trifluoro-1-methyl-ethoxy)-2H-[1,2,3]triazolo[4,5-d]pyrimidine;
(S)-1-[5-tert-Butyl-2-(2-chloro-benzyl)-2H-[1,2,3]triazolo[4,5-d]pyrimidin-7-yl]-3-methyl-pyrrolidin-3-ol;

(R)-1-[5-tert-Butyl-2-(2-chloro-benzyl)-2H-[1,2,3]triazolo [4,5-d]pyrimidin-7-yl]-3-methyl-pyrrolidin-3-ol;
(S)-1-[5-tert-Butyl-2-(2-trifluoromethyl-benzyl)-2H-[1,2,3] triazolo[4,5-d]pyrimidin-7-yl]-3-methyl-pyrrolidin-3-ol;
(R)-1-[5-tert-Butyl-2-(2-trifluoromethyl-benzyl)-2H-[1,2,3] triazolo[4,5-d]pyrimidin-7-yl]-3-methyl-pyrrolidin-3-ol;
(S)-1-[5-tert-Butyl-2-(2-methanesulfonyl-benzyl)-2H-[1,2, 3]triazolo[4,5-d]pyrimidin-7-yl]-3-methyl-pyrrolidin-3-ol;
(R)-1-[5-tert-Butyl-2-(2-methanesulfonyl-benzyl)-2H-[1,2, 3]triazolo[4,5-d]pyrimidin-7-yl]-3-methyl-pyrrolidin-3-ol;
(S)-1-[5-tert-Butyl-2-(3-chloro-pyridin-2-ylmethyl)-2H-[1, 2,3]triazolo[4,5-d]pyrimidin-7-yl]-3-methyl-pyrrolidin-3-ol;
(R)-1-[5-tert-Butyl-2-(3-chloro-pyridin-2-ylmethyl)-2H-[1, 2,3]triazolo[4,5-d]pyrimidin-7-yl]-3-methyl-pyrrolidin-3-ol;
(S)-1-[5-tert-Butyl-2-(5-methyl-[1,3,4]oxadiazol-2-ylmethyl)-2H-[1,2,3]triazolo[4,5-d]pyrimidin-7-yl]-3-methyl-pyrrolidin-3-ol;
(R)-1-[5-tert-Butyl-2-(5-methyl-[1,3,4]oxadiazol-2-ylmethyl)-2H-[1,2,3]triazolo[4,5-d]pyrimidin-7-yl]-3-methyl-pyrrolidin-3-ol;
(S)-1-[5-tert-Butyl-2-(3-methyl-[1,2,4]oxadiazol-5-ylmethyl)-2H-[1,2,3]triazolo[4,5-d]pyrimidin-7-yl]-3-methyl-pyrrolidin-3-ol;
(R)-1-[5-tert-Butyl-2-(3-methyl-[1,2,4]oxadiazol-5-ylmethyl)-2H-[1,2,3]triazolo[4,5-d]pyrimidin-7-yl]-3-methyl-pyrrolidin-3-ol;
(S)-1-[5-tert-Butyl-2-(1-methyl-1H-tetrazol-5-ylmethyl)-2H-[1,2,3]triazolo[4,5-d]pyrimidin-7-yl]-3-methyl-pyrrolidin-3-ol;
(R)-1-[5-tert-Butyl-2-(1-methyl-1H-tetrazol-5-ylmethyl)-2H-[1,2,3]triazolo[4,5-d]pyrimidin-7-yl]-3-methyl-pyrrolidin-3-ol;
(S)-1-[5-tert-Butyl-2-(4-methyl-furazan-3-ylmethyl)-2H-[1, 2,3]triazolo[4,5-d]pyrimidin-7-yl]-3-methyl-pyrrolidin-3-ol;
(R)-1-[5-tert-Butyl-2-(4-methyl-furazan-3-ylmethyl)-2H-[1,2,3]triazolo[4,5-d]pyrimidin-7-yl]-3-methyl-pyrrolidin-3-ol;
(S)-1-[5-tert-Butyl-2-(3,3,3-trifluoro-propyl)-2H-[1,2,3] triazolo[4,5-d]pyrimidin-7-yl]-3-methyl-pyrrolidin-3-ol;
(R)-1-[5-tert-Butyl-2-(3,3,3-trifluoro-propyl)-2H-[1,2,3] triazolo[4,5-d]pyrimidin-7-yl]-3-methyl-pyrrolidin-3-ol;
(S)-1-[5-tert-Butyl-2-(1-cyclopropyl-1H-tetrazol-5-ylmethyl)-2H-[1,2,3]triazolo[4,5-d]pyrimidin-7-yl]-3-methyl-pyrrolidin-3-ol;
(R)-1-[5-tert-Butyl-2-(1-cyclopropyl-1H-tetrazol-5-ylmethyl)-2H-[1,2,3]triazolo[4,5-d]pyrimidin-7-yl]-3-methyl-pyrrolidin-3-ol;
N—{(S)-1-[2-(2-Chloro-benzyl)-5-(2,2-dimethyl-propoxy)-2H-[1,2,3]triazolo[4,5-d]pyrimidin-7-yl]-pyrrolidin-3-yl}-acetamide;
N—{(S)-1-[2-(3-Chloro-pyridin-2-ylmethyl)-5-(2,2-dimethyl-propoxy)-2H-[1,2,3]triazolo[4,5-d]pyrimidin-7-yl]-pyrrolidin-3-yl}-acetamide;
tert-Butyl-[7-(3,3-difluoro-pyrrolidin-1-yl)-2-(2-trifluoromethyl-benzyl)-2H-[1,2,3]triazolo[4,5-d]pyrimidin-5-yl]-amine;
tert-Butyl-[7-(3,3-difluoro-pyrrolidin-1-yl)-2-(2-methanesulfonyl-benzyl)-2H-[1,2,3]triazolo[4,5-d]pyrimidin-5-yl]-amine;
tert-Butyl-[2-(3-chloro-pyridin-2-ylmethyl)-7-(3,3-difluoro-pyrrolidin-1-yl)-2H-[1,2,3]triazolo[4,5-d]pyrimidin-5-yl]-amine;
tert-Butyl-[7-(3,3-difluoro-pyrrolidin-1-yl)-2-(1-methyl-1H-tetrazol-5-ylmethyl)-2H-[1,2,3]triazolo[4,5-d]pyrimidin-5-yl]-amine;
tert-Butyl-[7-(3,3-difluoro-pyrrolidin-1-yl)-2-(4-methyl-furazan-3-ylmethyl)-2H-[1,2,3]triazolo[4,5-d]pyrimidin-5-yl]-amine;
N—{(S)-1-[2-(2-Chloro-benzyl)-5-((S)-2,2,2-trifluoro-1-methyl-ethoxy)-2H-[1,2,3]triazolo[4,5-d]pyrimidin-7-yl]-pyrrolidin-3-yl}-acetamide;
N—{(S)-1-[2-(2-Trifluoromethyl-benzyl)-5-((S)-2,2,2-trifluoro-1-methyl-ethoxy)-2H-[1,2,3]triazolo[4,5-d]pyrimidin-7-yl]-pyrrolidin-3-yl}-acetamide;
N—{(S)-1-[2-(2-M ethanesulfonyl-benzyl)-5-((S)-2,2,2-trifluoro-1-methyl-ethoxy)-2H-[1,2,3]triazolo[4,5-d]pyrimidin-7-yl]-pyrrolidin-3-yl}-acetamide;
N—{(S)-1-[5-tert-Butylamino-2-(2-chloro-benzyl)-2H-[1, 2,3]triazolo[4,5-d]pyrimidin-7-yl]-pyrrolidin-3-yl}-acetamide; and
(S)-1-[5-tert-Butylamino-2-(1-methyl-1H-tetrazol-5-ylmethyl)-2H-[1,2,3]triazolo[4,5-d]pyrimidin-7-yl]-pyrrolidin-3-ol.

The invention further relates in particular to a compound of formula (I) selected from the group consisting of
5-tert-Butyl-2-(2-chloro-benzyl)-7-morpholin-4-yl-2H-[1,2, 3]triazolo[4,5-d]pyrimidine;
5-tert-Butyl-2-cyclohexylmethyl-7-(3,3-difluoro-pyrrolidin-1-yl)-2H-[1,2,3]triazolo[4,5-d]pyrimidine;
5-tert-Butyl-7-(3,3-difluoro-pyrrolidin-1-yl)-2-pyridin-4-ylmethyl-2H-[1,2,3]triazolo[4,5-d]pyrimidine;
5-tert-Butyl-7-(3,3-difluoro-pyrrolidin-1-yl)-2-(2,2,2-trifluoro-ethyl)-2H-[1,2,3]triazolo[4,5-d]pyrimidine;
2-(2-Bromo-benzyl)-5-tert-butyl-7-(3,3-difluoro-pyrrolidin-1-yl)-2H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-2-ylmethyl]-benzonitrile;
5-tert-Butyl-7-(3,3-difluoro-pyrrolidin-1-yl)-2-phenethyl-2H-[1,2,3]triazolo[4,5-d]pyrimidine; and
5-tert-Butyl-2-[(R)-1-(2-chloro-phenyl)-ethyl]-7-(3,3-difluoro-pyrrolidin-1-yl)-2H-[1,2,3]triazolo[4,5-d]pyrimidine.

The invention also particularly relates to a compound of formula (I) selected from the group consisting of
5-tert-Butyl-2-(4-chloro-pyridin-3-ylmethyl)-7-(3,3-difluoro-pyrrolidin-1-yl)-2H-[1,2,3]triazolo[4,5-d]pyrimidine;
5-tert-Butyl-2-(3-chloro-pyridin-2-ylmethyl)-7-(3,3-difluoro-pyrrolidin-1-yl)-2H-[1,2,3]triazolo[4,5-d]pyrimidine;
5-tert-Butyl-7-(3,3-difluoro-pyrrolidin-1-yl)-2-(4-methyl-furazan-3-ylmethyl)-2H-[1,2,3]triazolo[4,5-d]pyrimidine;
5-tert-Butyl-2-(3-chloro-pyridin-4-ylmethyl)-7-(3,3-difluoro-pyrrolidin-1-yl)-2H-[1,2,3]triazolo[4,5-d]pyrimidine; and
(S)-1-[5-tert-Butyl-2-(2-trifluoromethyl-benzyl)-2H-[1,2,3] triazolo[4,5-d]pyrimidin-7-yl]-pyrrolidin-3-ol.

The preparation of compounds of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations, 2nd Edition*, Richard C. Larock. John Wiley & Sons, New York, N.Y. 1999). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

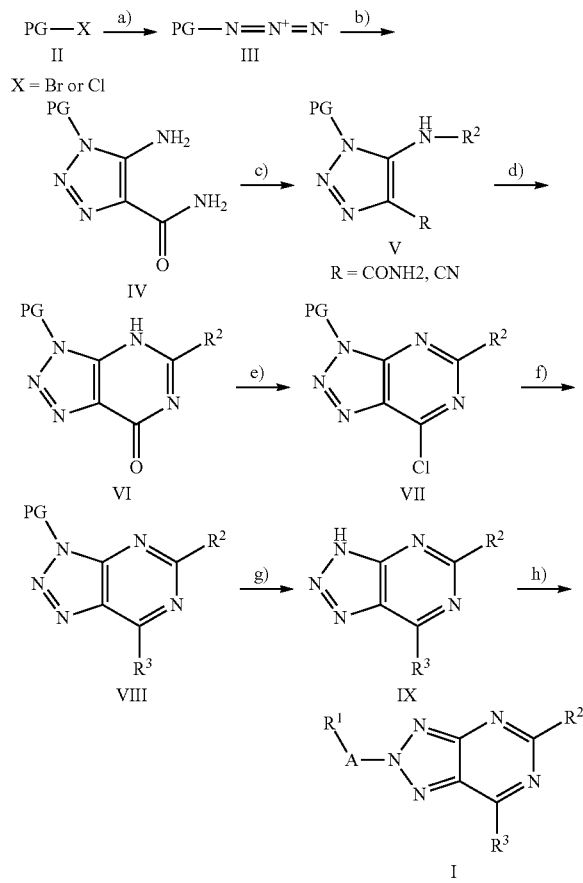

a) Halides II are either commercially available or can be synthesized according to methods known in the art. These halides II are conveniently reacted with sodium azide in a suitable solvent such as acetonitrile, ethanol or DMF to afford azide derivatives III.

b) Triazole derivatives IV can be prepared by a [2+3]cycloaddition of azide derivatives III with 2-cyanoacetamide in the presence of an appropriate base such as sodium methoxide or sodium ethoxide in a suitable solvent such as methanol, ethanol or DMF.

c) Triazole derivatives V can be obtained by acylation of IV with an acyl-halide in the presence of a base such as DIEA, DMAP, pyridine and the like.

d) Triazolopyrimidine derivatives VI can be prepared by intramolecular cyclization of triazole derivative V in the presence of a base such as $KHCO_3$, $Na_2CO_3$ and water either with or without a solvent such as methanol, ethanol, dioxane and toluene.

e) Chlorides VII can be obtained by reaction of VI with a chlorination reagent such as $POCl_3$, $SOCl_2$ or $(COCl)_2$ in the presence of an appropriate base such as N,N-diethyl aniline, lutidine, or pyridine.

f) VII are conveniently reacted with various nucleophiles particularly amines in the presence of an appropriate base such as triethylamine, DIEA or DBU in a suitable solvent such as acetonitrile, methanol, toluene or DMF to yield triazolo-pyrimidine derivatives VIII.

g) Deprotection of VIII is done under suitable conditions, in case of PG=MPM under acidic conditions (TFA and the like), hydrogenation using Pd catalyst or oxidative cleavage (DDQ or CAN and the like) to yield IX.

h) Triazole derivatives IX are conveniently reacted either with a halide (or sulfonate) in the presence of suitable base such as DIEA, DBU, $K_2CO_3$, or $Cs_2CO_3$ particularly $Ag_2SO_4$ in a solvent such as DMF, dioxane or toluene, or alternatively with an alcohol under Mitsunobu reaction conditions using a suitable diazodicarboxylate (DEAD, DIAD and the like) and a phosphine such as $PBu_3$ or $PPh_3$ in an appropriate solvent such as THF, DCM, toluene to afford final triazolo-pyrimidine derivatives I.

The invention thus also relates to a process for the preparation of a compound of formula (I) comprising the reaction of a compound of formula (A)

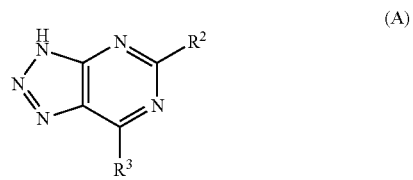

in the presence of $R^1$-A-X and a base, or in the presence of $R^1$-A-OH under Mitsunobu conditions, wherein A and $R^1$ to $R^3$ are as defined above and wherein X is halogen or $SO_2$. Reaction conditions of step h) above can thus be used in the process of the invention.

The invention also relates to a compound of formula (I) when manufactured according to a process of the invention.

The invention further relates to a compound of formula (I) for use as therapeutically active substance.

The invention further relates to a pharmaceutical composition comprising a compound of formula (I) and a therapeutically inert carrier.

The invention relates in particular to:

The use of a compound of formula (I) for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis;

The use of a compound according of formula (I) for the preparation of a medicament for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis;

A compound of formula (I) for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis; and A method for the treatment or prophylaxis of pain, atherosclerosis, age-related macular degeneration, diabetic retinopathy, glaucoma, diabetes mellitus, inflammation, inflammatory bowel disease, ischemia-reperfusion injury, acute liver failure, liver fibrosis, lung fibrosis, kidney fibrosis, systemic fibrosis, acute allograft rejection, chronic allograft nephropathy, diabetic nephropathy, glomerulonephropathy, cardiomyopathy, heart failure, myocardial ischemia, myocardial infarction, systemic sclerosis, thermal injury, burning, hypertrophic scars, keloids, gingivitis pyrexia, liver cirrhosis or tumors, regulation of bone mass, neurodegeneration, stroke, transient ischemic attack or uveitis, which method comprises administering an effective amount of a compound of formula (I) to a patient in need thereof.

The use of a compound of formula (I) for the treatment or prophylaxis of pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors is another object of the invention.

The use of a compound of formula (I) for the preparation of a medicament for the treatment or prophylaxis of chronic pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors is a further object of the invention.

The invention also relates to a compound of formula (I) for the treatment or prophylaxis of pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors.

The invention particularly relates to a compound of formula (I) for the treatment or prophylaxis of ischemia, reperfusion injury, liver fibrosis or kidney fibrosis, in particular ischemia or reperfusion injury.

The invention is further directed to a compound of formula (I), when manufactured according to a process according to the invention.

A method for the treatment or prophylaxis of pain, in particular chronic pain, atherosclerosis, regulation of bone mass, inflammation, ischemia, reperfusion injury, systemic fibrosis, liver fibrosis, lung fibrosis, kidney fibrosis, chronic allograft nephropathy, congestive heart failure, myocardial infarction, systemic sclerosis, glomerulonephropathy, thermal injury, burning, hypertrophic scars, keloids, gingivitis pyrexia, liver cirrhosis or tumors, which method comprises administering an effective amount of a compound of formula (I) is also an object of the invention.

Another embodiment of the invention provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) aresterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention will now be illustrated by the following examples which have no limiting character.

EXAMPLES

Abbreviations

MS=mass spectrometry; CAN=eerie ammonium nitrate; Ac=acetyl; DIEA=N,N-diisopropylethylamine; DBU=1,8-Diazabicyclo[5.4.0]undec-7-ene; DMF=dimethylformamide; HPLC=LC=high performance liquid chromatography; THF=tetrahydrofurane; TFA=trifluoroacetic acid; Ph=phenyl; DCM=dichloromethane; MPM=p-methoxyphenylmethyl; DDQ=2,3-Dichloro-5,6-dicyano-1,4-benzoquinone; PMB=p-methoxy-benzyl; DIPEA=diisopropylethylamine. Chiral separation of 1-(3-Benzyl-5-tert-butyl-3H-[1,2,3]triazolo[4,5-d]pyrimidin-7-yl)-3-methyl-pyrrolidin-3-ol (example 124, step a) yielded the respective enantiopure R and S derivatives. However, the unequivocal stereochemical assignment is pending. Therefore, thestereochemical assignment for enantiopure examples 124-133 has not been made.

Example 1

5-tert-Butyl-2-(2-chloro-benzyl)-7-morpholin-4-yl-2H-[1,2,3]triazolo[4,5d]pyrimidine

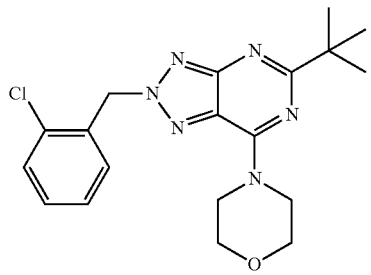 [SMILES: CC(C)(C)c1nc(N2CCOCC2)c2nn(Cc3ccccc3Cl)nc2n1]

a) 5-Amino-1-(4-methoxybenzyl)-1H-1,2,3-triazole-4-carboxamide

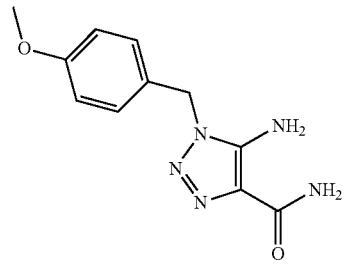 [SMILES: COc1ccc(Cn2nnc(C(N)=O)c2N)cc1]

A mixture of 1-(chloromethyl)-4-methoxybenzene (20.0 g, 128 mmol) and sodium azide (12.5 g, 192 mmol) in acetonitrile (255 mL) was refluxed for 5 h under $N_2$ atmosphere. The mixture was filtered and concentrated in vacuo. The residue was diluted in DCM, washed with $H_2O$ and brine, dried over $Na_2SO_4$ and concentrated in vacuo to afford crude 1-(azidomethyl)-4-methoxybenzene. The residue was used for the next reaction without further purification.

A mixture of the above crude residue, 2-cyanoacetamide (10.8 g, 128 mmol) and sodium ethanolate (8.71 g, 128 mmol) in ethanol (256 mL) was refluxed for 21 h under $N_2$ atmosphere. The mixture was concentrated in vacuo, diluted with 4M AcOH aq. and filtered. The residue was washed with $H_2O$ and dried in vacuo to afford 5-amino-1-(4-methoxybenzyl)-1H-1,2,3-triazole-4-carboxamide as pale-orange solid (26.5 g, 84% for 2 steps). MS (m/e): 248.1 ($MH^+$)

b) 5-tert-Butyl-3-(4-methoxybenzyl)-3H-[1,2,3]triazolo[4,5-d]pyrimidin-7(4H)-one

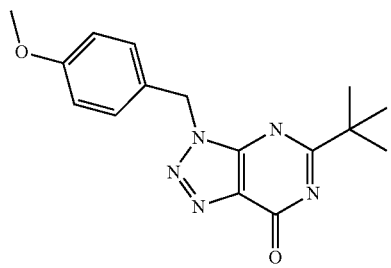 [SMILES: COc1ccc(Cn2nnc3c(=O)nc(C(C)(C)C)[nH]c32)cc1]

A mixture of 5-amino-1-(4-methoxybenzyl)-1H-1,2,3-triazole-4-carboxamide (10.0 g, 40.4 mmol) and pivaloyl chloride (7.47 mL, 60.7 mmol) in pyridine (20.2 mL) was stirred at 80° C. for 2 h under $N_2$ atmosphere. Then, to the reaction mixture was added 8 M sodium hydroxide aq. (15.2 mL, 121 mmol) and methanol (20.2 mL). After being stirred at 80° C. for 1 h, the reaction mixture was poured into 1M HCl aq., extracted with diethyl ether, washed with 2M HCl aq., water and brine, dried over $Na_2SO_4$ and concentrated in vacuo to afford the mixture of crude 1-(4-methoxybenzyl)-5-pivalamido-1H-1,2,3-triazole-4-carboxamide and N-(4-cyano-1-(4-methoxybenzyl)-1H-1,2,3-triazol-5-yl)pivalamide. The residue was used for the next reaction without further purification.

A mixture of the above crude residue and $KHCO_3$ (12.1 g, 121 mmol) in $H_2O$ (242 mL) was refluxed for 18 h. The reaction mixture was poured into 1M HCl aq., extracted with EtOAc, washed with brine, dried over Na$_2$SO$_4$ and concentrated in vacuo. The crude residue was purified by flash chromatography (silica gel, 10% to 70% EtOAc in heptane) to afford 5-tert-butyl-3-(4-methoxybenzyl)-3H-[1,2,3]triazolo[4,5-d]pyrimidin-7(4H)-one (4.44 g, 35% for 2 steps). MS (m/e): 314.2 (MH$^+$).

c) 4-(5-tert-Butyl-3-(4-methoxybenzyl)-3H-[1,2,3]triazolo[4,5-d]pyrimidin-7-yl)morpholine

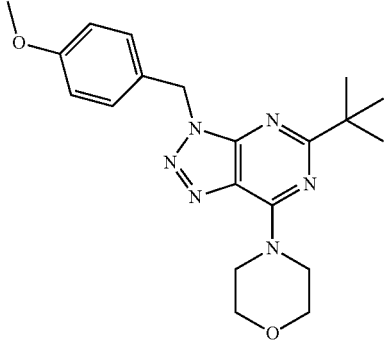 [SMILES: COc1ccc(Cn2nnc3c(N4CCOCC4)nc(C(C)(C)C)nc32)cc1]

A mixture of 5-tert-butyl-3-(4-methoxybenzyl)-3H-[1,2,3]triazolo[4,5-d]pyrimidin-7(4H)-one (50.0 mg, 160 µmol) and N,N-diethylaniline (50.8 µL, 319 µmol) in POCl$_3$ (1000 µL, 10.9 mmol) was refluxed for 4 h under N$_2$ atmosphere. The reaction mixture was concentrated in vacuo, diluted with EtOAc, washed with cold H$_2$O and brine, dried over Na$_2$SO$_4$ and concentrated in vacuo to afford crude 5-tert-butyl-7-chloro-3-(4-methoxy benzyl)-3H-[1,2,3]triazolo[4,5-d]pyrimidine. The residue was used for the next reaction without further purification.

A mixture of the above crude residue, morpholine (28.0 µL, 320 µmol) and DIEA (55.9 µL, 320 µmol) in acetonitrile (250 µL) was stirred at the room temperature overnight. The reaction mixture was directly purified by preparative HPLC (column: Gemini 5 um C18 110A 75×30 mm. mobile phase: water (0.05% Et$_3$N): acetonitrile 45:55% to 5:95%. WL: 280 nm Flow: 30 mL/min.) to afford the title compound as white solid (47.7 mg, 78% for 2 steps). MS (m/e): 383.4 (MH$^+$).

d) 5-tert-Butyl-2-(2-chloro-benzyl)-7-morpholin-4-yl-2H-[1,2,3]triazolo[4,5-d]pyrimidine A mixture of 4-(5-tert-butyl-3-(4-methoxybenzyl)-3H-[1,2,3]triazolo[4,5-d]pyrimidin-7-yl)morpholine (49.0 mg, 128 µmol) and TFA (1000 µL) was refluxed for 8 h under N$_2$ atmosphere. The reaction mixture was concentrated in vacuo to afford crude to 5-tert-butyl-7-morpholin-4-yl-3H-[1,2,3]triazolo[4,5-d]pyrimidine. The residue was used for the next reaction without further purification.

A mixture of the portion of above residue (85.3 µmol), 1-(bromomethyl)-2-chlorobenzene (22.1 µL, 171 µmol) and DBU (25.7 µL, 171 µmol) in DMF (500 µL) was stirred at the room temperature overnight. The reaction mixture was directly purified by preparative HPLC (column: Gemini 5 um C18 110A 75×30 mm. mobile phase: water (0.05% Et$_3$N): acetonitrile 65:35% to 5:95%. WL: 300 nm Flow: 30 mL/min.) to afford the title compound as white solid (8.0 mg, 24%). MS (m/e): 387.4 (MH$^+$).

Example 2

5-tert-Butyl-2-(2-chloro-4-fluoro-benzyl)-7-morpholin-4-yl-2H-[1,2,3]triazolo[4,5-d]pyrimidine

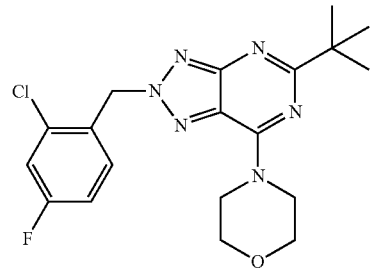 [SMILES: CC(C)(C)c1nc(N2CCOCC2)c2nn(Cc3ccc(F)cc3Cl)nc2n1]

In analogy to the procedure described for the synthesis of 5-tert-butyl-2-(2-chloro-benzyl)-7-morpholin-4-yl-2H-[1,2,3]triazolo[4,5-d]pyrimidine (example 1, step d), the title compound was prepared from 5-tert-butyl-7-morpholin-4-yl-3H-[1,2,3]triazolo[4,5-d]pyrimidine and 1-(bromomethyl)-2-chloro-4-fluorobenzene and isolated as white solid (5.1 mg, 30%). MS (m/e): 405.4 (MH$^+$).

Example 3

5-tert-Butyl-7-(3,3-difluoro-pyrrolidin-1-yl)-2-ethyl-2H-[1,2,3]triazolo[4,5-d]pyrimidine

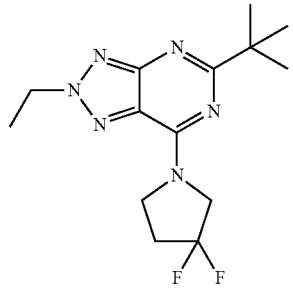 [SMILES: CCn1nc2nc(C(C)(C)C)nc(N3CCC(F)(F)C3)c2n1]

a) 5-tert-Butyl-7-(3,3-difluoro-pyrrolidin-1-yl)-3-(4-methoxy-benzyl)-3H-[1,2,3]triazolo[4,5-d]pyrimidine

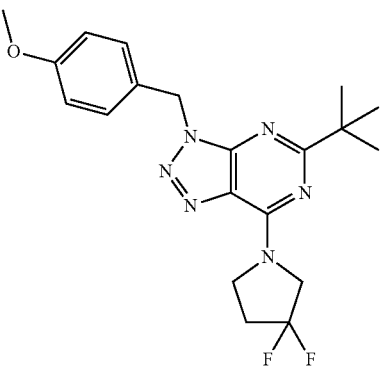 [SMILES: COc1ccc(Cn2nnc3c(N4CCC(F)(F)C4)nc(C(C)(C)C)nc32)cc1]

In analogy to the procedure described for the synthesis of 4-(5-tert-butyl-3-(4-methoxy benzyl)-3H-[1,2,3]triazolo[4,5-d]pyrimidin-7-yl)morpholine (example 1, step c), the title compound was prepared from 5-tert-butyl-7-chloro-3-(4-methoxybenzyl)-3H-[1,2,3]triazolo[4,5-d]pyrimidine and 3,3-difluoropyrrolidine hydrochloride and isolated as white solid (5.1 mg, 30%). MS (m/e): 405.4 (MH$^+$).

b) 5-tert-Butyl-7-(3,3-difluoro-pyrrolidin-1-yl)-2-ethyl-2H-[1,2,3]triazolo[4,5-d]pyrimidine A mixture of 5-tert-butyl-7-(3,3-difluoro-pyrrolidin-1-yl)-3-(4-methoxy-benzyl)-3H-[1,2,3]triazolo[4,5-d]pyrimidine (264 mg, 656 µmol) and TFA (5.00 mL) was refluxed for 8 h under N$_2$ atmosphere. The reaction mixture was concentrated in vacuo to afford crude to 5-tert-butyl-7-(3,3-difluoropyrrolidin-1-yl)-3H-[1,2,3]triazolo[4,5-d]pyrimidine. The residue was used for the next reaction without further purification.

A mixture of the portion of above residue (41.0 µmol), iodoethane (6.63 µL, 82.0 mmol) and DBU (12.4 µL, 82.0 µmol) in DMF (250 µL) was stirred at the room temperature overnight. The reaction mixture was directly purified by preparative HPLC (column: Gemini 5 um C18 110A 75×30 mm. mobile phase: water (0.05% Et$_3$N): acetonitrile 60:40% to 5:95%. WL: 300 nm Flow: 30 mL/min.) to afford the title compound as white solid (4.2 mg, 33%). MS (m/e): 311.3 (MH$^+$).

Example 4

5-tert-Butyl-7-(3,3-difluoro-pyrrolidin-1-yl)-2-(2-methoxy-ethyl)-2H-[1,2,3]triazolo[4,5-d]pyrimidine

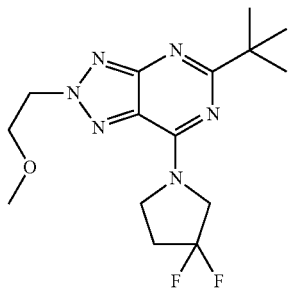 [SMILES: COCCn1nc2nc(C(C)(C)C)nc(N3CCC(F)(F)C3)c2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-bromo-2-methoxyethane and isolated as light-yellow gum (4.5 mg, 32%). MS (m/e): 341.3 (MH$^+$).

Example 5

2-[5-tert-Butyl-7-(3,3-difluoro-pyrrolidin-1-yl)-[1,2,3]triazolo[4,5-d]pyrimidin-2-yl]-ethanol

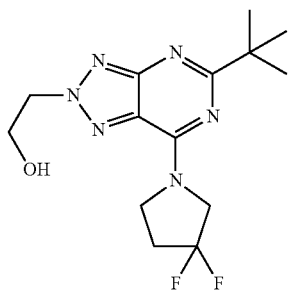 [SMILES: CC(C)(C)c1nc(N2CCC(F)(F)C2)c2nn(CCO)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-bromoethanol and isolated as white solid (1.9 mg, 14%). MS (m/e): 327.3 (MH$^+$).

Example 6

5-tert-Butyl-2-cyclohexylmethyl-7-(3,3-difluoro-pyrrolidin-1-yl)-2H-[1,2,3]triazolo[4,5-d]pyrimidine

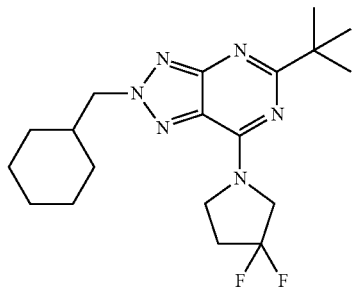 [SMILES: CC(C)(C)c1nc(N2CCC(F)(F)C2)c2nn(CC3CCCCC3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and (bromomethyl)cyclohexane and isolated as white solid (6.1 mg, 39%). MS (m/e): 379.4 (MH$^+$).

Example 7

5-tert-Butyl-2-(3-chloro-benzyl)-7-(3,3-difluoro-pyrrolidin-1-yl)-2H-[1,2,3]triazolo[4,5-d]pyrimidine

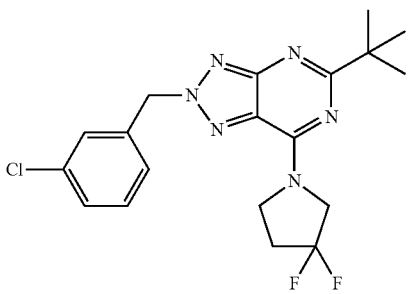 [SMILES: CC(C)(C)c1nc(N2CCC(F)(F)C2)c2nn(Cc3cccc(Cl)c3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(bromomethyl)-3-chlorobenzene and isolated as white solid (4.8 mg, 29%). MS (m/e): 407.4 (MH$^+$).

Example 8

5-tert-Butyl-2-(4-chloro-benzyl)-7-(3,3-difluoro-pyrrolidin-1-yl)-2H-[1,2,3]triazolo[4,5-d]pyrimidine

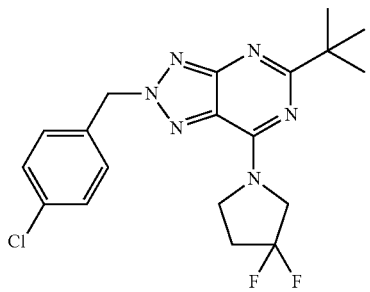 [SMILES: CC(C)(C)c1nc(N2CCC(F)(F)C2)c2nn(Cc3ccc(Cl)cc3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(bromomethyl)-4-chlorobenzene and isolated as white solid (5.1 mg, 31%). MS (m/e): 407.4 (MH$^+$).

Example 9

5-tert-Butyl-2-(2,3-dichloro-benzyl)-7-(3,3-difluoro-pyrrolidin-1-yl)-2H-[1,2,3]triazolo[4,5-d]pyrimidine

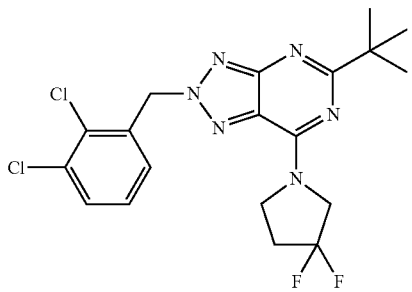 [SMILES: CC(C)(C)c1nc(N2CCC(F)(F)C2)c2nn(Cc3cccc(Cl)c3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(bromomethyl)-2,3-dichlorobenzene and isolated as white solid (5.5 mg, 30%). MS (m/e): 441.4 (MH$^+$).

Example 10

5-tert-Butyl-2-(2,4-dichloro-benzyl)-7-(3,3-difluoro-pyrrolidin-1-yl)-2H-[1,2,3]triazolo[4,5-d]pyrimidine

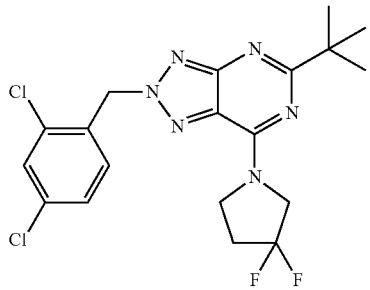 [SMILES: CC(C)(C)c1nc(N2CCC(F)(F)C2)c2nn(Cc3ccc(Cl)cc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(bromomethyl)-2,4-dichlorobenzene and isolated as white solid (5.3 mg, 29%). MS (m/e): 441.4 (MH$^+$).

Example 11

5-tert-Butyl-2-(2,5-dichloro-benzyl)-7-(3,3-difluoro-pyrrolidin-1-yl)-2H-[1,2,3]triazolo[4,5-d]pyrimidine

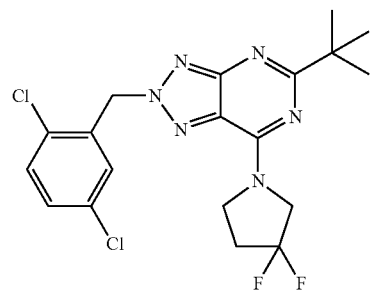 [SMILES: CC(C)(C)c1nc(N2CCC(F)(F)C2)c2nn(Cc3cc(Cl)ccc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(bromomethyl)-1,4-dichlorobenzene and isolated as white solid (4.6 mg, 25%). MS (m/e): 441.4 (MH$^+$).

Example 12

5-tert-Butyl-2-(2,6-dichloro-benzyl)-7-(3,3-difluoro-pyrrolidin-1-yl)-2H-[1,2,3]triazolo[4,5-d]pyrimidine

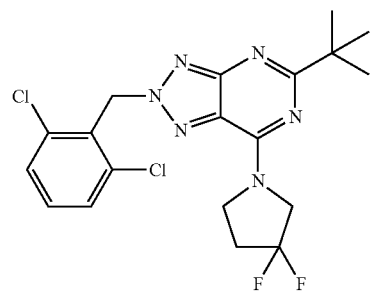 [SMILES: CC(C)(C)c1nc(N2CCC(F)(F)C2)c2nn(Cc3c(Cl)cccc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(bromomethyl)-1,3-dichlorobenzene and isolated as white solid (5.8 mg, 32%). MS (m/e): 441.4 (MH$^+$).

Example 13

5-tert-Butyl-2-(2-chloro-4-fluoro-benzyl)-7-(3,3-difluoro-pyrrolidin-1-yl)-2H-[1,2,3]triazolo[4,5-d]pyrimidine

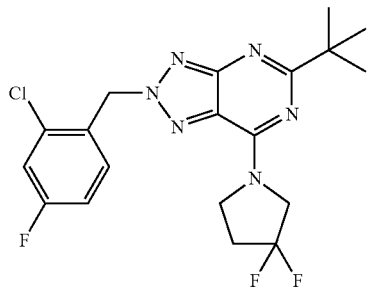 [SMILES: CC(C)(C)c1nc(N2CCC(F)(F)C2)c2nn(Cc3ccc(F)cc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(bromomethyl)-2-chloro-4-fluorobenzene and isolated as colorless gum (5.5 mg, 32%). MS (m/e): 425.4 (MH$^+$).

Example 14

5-tert-Butyl-2-(2-chloro-6-fluoro-benzyl)-7-(3,3-difluoro-pyrrolidin-1-yl)-2H-[1,2,3]triazolo[4,5-d]pyrimidine

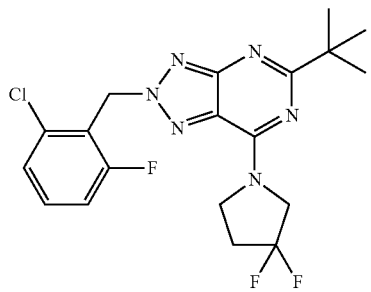 [SMILES: CC(C)(C)c1nc(N2CCC(F)(F)C2)c2nn(Cc3c(F)cccc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-chloro-2-(chloromethyl)-3-fluorobenzene and isolated as white solid (5.4 mg, 31%). MS (m/e): 425.4 (MH$^+$).

Example 15

5-tert-Butyl-7-(3,3-difluoro-pyrrolidin-1-yl)-2-pyridin-2-ylmethyl-2H-[1,2,3]triazolo[4,5-d]pyrimidine

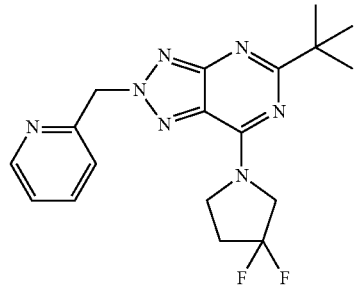 [SMILES: CC(C)(C)c1nc(N2CCC(F)(F)C2)c2nn(Cc3ccccn3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(bromomethyl)pyridine hydrobromide and isolated as white gum (5.0 mg, 33%). MS (m/e): 374.4 (MH$^+$).

Example 16

5-tert-Butyl-7-(3,3-difluoro-pyrrolidin-1-yl)-2-pyridin-3-ylmethyl-2H-[1,2,3]triazolo[4,5-d]pyrimidine

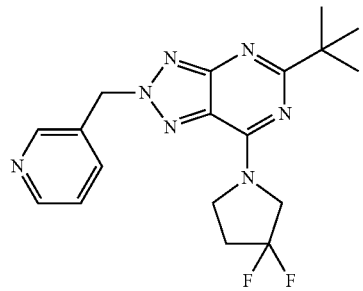 [SMILES: CC(C)(C)c1nc(N2CCC(F)(F)C2)c2nn(Cc3cccnc3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-(chloromethyl)pyridine hydrochloride and isolated as colorless gum (2.2 mg, 14%). MS (m/e): 374.4 (MH$^+$).

Example 17

5-tert-Butyl-7-(3,3-difluoro-pyrrolidin-1-yl)-2-pyridin-4-ylmethyl-2H-[1,2,3]triazolo[4,5-d]pyrimidine

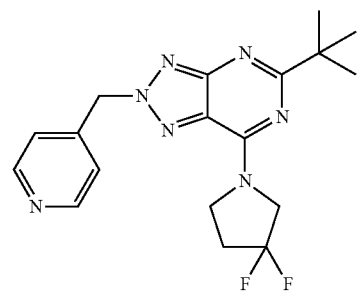 [SMILES: CC(C)(C)c1nc(N2CCC(F)(F)C2)c2nn(Cc3ccncc3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 4-(bromomethyl)pyridine hydrobromide and isolated as orange solid (4.1 mg, 27%). MS (m/e): 374.4 (MH$^+$).

Example 18

5-tert-Butyl-7-(3,3-difluoro-pyrrolidin-1-yl)-2-(2,2,2-trifluoro-ethyl)-2H-[1,2,3]triazolo[4,5-d]pyrimidine

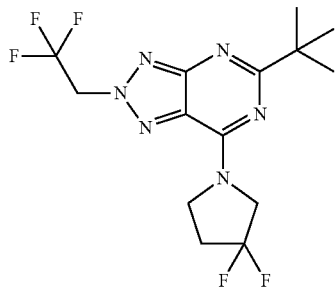 [SMILES: CC(C)(C)c1nc(N2CCC(F)(F)C2)c2nn(CC(F)(F)F)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2,2,2-trifluoroethyl trifluoromethanesulfonate and isolated as light-yellow solid (3.0 mg, 20%). MS (m/e): 365.3 (MH$^+$).

Example 19

5-tert-Butyl-2-(2-chloro-4,5-difluoro-benzyl)-7-(3,3-difluoro-pyrrolidin-1-yl)-2H-[1,2,3]triazolo[4,5-d]pyrimidine

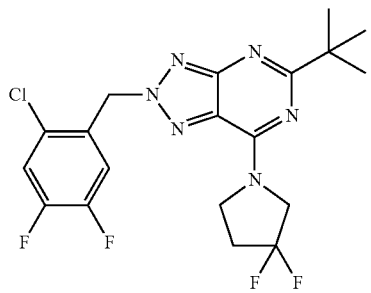 [SMILES: CC(C)(C)c1nc(N2CCC(F)(F)C2)c2nn(Cc3cc(F)c(F)cc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(bromomethyl)-2-chloro-4,5-difluorobenzene and isolated as colorless gum (6.2 mg, 34%). MS (m/e): 443.4 (MH$^+$).

Example 20

5-tert-Butyl-2-(2-chloro-3,6-difluoro-benzyl)-7-(3,3-difluoro-pyrrolidin-1-yl)-2H-[1,2,3]triazolo[4,5-d]pyrimidine

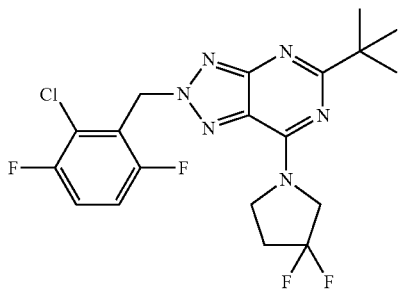 [SMILES: CC(C)(C)c1nc(N2CCC(F)(F)C2)c2nn(Cc3c(F)ccc(F)c3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(bromomethyl)-3-chloro-1,4-difluorobenzene and isolated as white solid (7.0 mg, 38%). MS (m/e): 443.4 (MH$^+$).

Example 21

2-(2-Bromo-benzyl)-5-tert-butyl-7-(3,3-difluoro-pyrrolidin-1-yl)-2H-[1,2,3]triazolo[4,5-d]pyrimidine

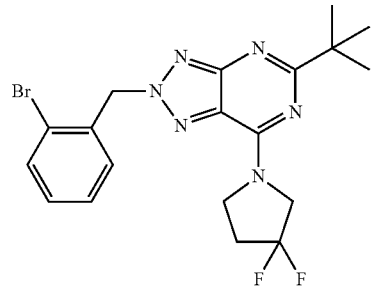 [SMILES: CC(C)(C)c1nc(N2CCC(F)(F)C2)c2nn(Cc3ccccc3Br)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-bromo-2-(bromomethyl)benzene and isolated as colorless gum (6.9 mg, 37%). MS (m/e): 451.3 (MH$^+$).

Example 22

5-tert-Butyl-7-(3,3-difluoro-pyrrolidin-1-yl)-2-(2-trifluoromethyl-benzyl)-2H-[1,2,3]triazolo[4,5-d]pyrimidine

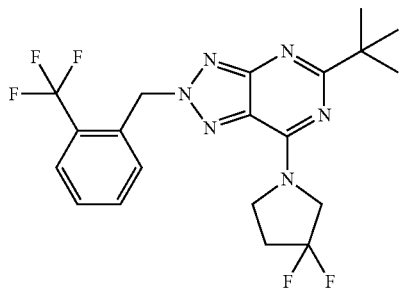 [SMILES: CC(C)(C)c1nc(N2CCC(F)(F)C2)c2nn(Cc3ccccc3C(F)(F)F)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(bromomethyl)-2-(trifluoromethyl)benzene and isolated as colorless gum (8.5 mg, 47%). MS (m/e): 441.4 (MH$^+$).

Example 23

5-tert-Butyl-7-(3,3-difluoro-pyrrolidin-1-yl)-2-(2-methoxy-benzyl)-2H-[1,2,3]triazolo[4,5-d]pyrimidine

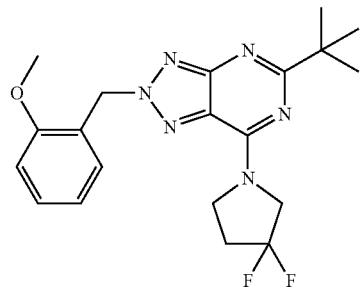 [SMILES: COc1ccccc1Cn1nc2nc(C(C)(C)C)nc(N3CCC(F)(F)C3)c2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(chloromethyl)-2-methoxybenzene and isolated as colorless gum (6.6 mg, 40%). MS (m/e): 403.4 (MH$^+$).

Example 24

5-tert-Butyl-7-(3,3-difluoro-pyrrolidin-1-yl)-2-(2-trifluoromethoxy-benzyl)-2H-[1,2,3]triazolo[4,5-d]pyrimidine

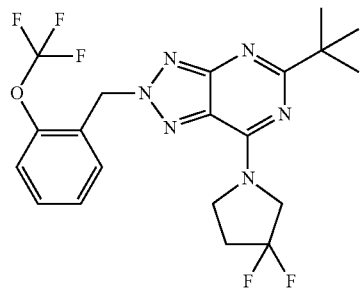 [SMILES: CC(C)(C)c1nc(N2CCC(F)(F)C2)c2nn(Cc3ccccc3OC(F)(F)F)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(bromomethyl)-2-(trifluoromethoxy)benzene and isolated as light-yellow gum (7.3 mg, 39%). MS (m/e): 457.4 (MH$^+$).

Example 25

2-[5-tert-Butyl-7-(3,3-difluoro-pyrrolidin-1-yl)-[1,2,3]triazolo[4,5-d]pyrimidin-2-yl methyl]-benzonitrile

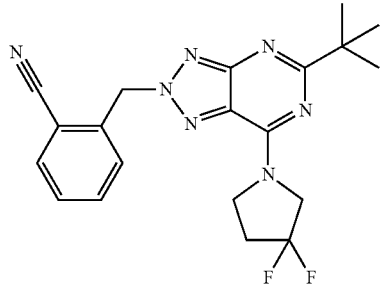 [SMILES: CC(C)(C)c1nc(N2CCC(F)(F)C2)c2nn(Cc3ccccc3C#N)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(bromomethyl)benzonitrile and isolated as white solid (6.1 mg, 37%). MS (m/e): 398.3 (MH$^+$).

Example 26

5-tert-Butyl-7-(3,3-difluoro-pyrrolidin-1-yl)-2-phenethyl-2H-[1,2,3]triazolo[4,5-d]pyrimidine

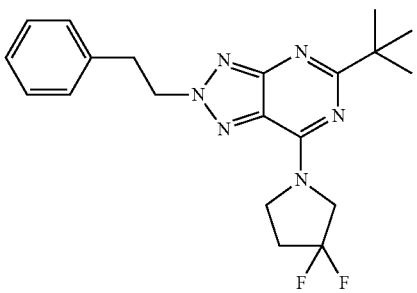 [SMILES: CC(C)(C)c1nc(N2CCC(F)(F)C2)c2nn(CCc3ccccc3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and (2-bromoethyl)benzene and isolated as light-yellow gum (7.3 mg, 46%). MS (m/e): 387.4 (MH$^+$).

Example 27

2-[5-tert-Butyl-7-(3,3-difluoro-pyrrolidin-1-yl)-[1,2,3]triazolo[4,5-d]pyrimidin-2-yl]-1-phenyl-ethanone

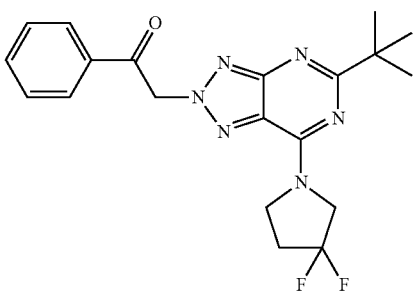 [SMILES: CC(C)(C)c1nc(N2CCC(F)(F)C2)c2nn(CC(=O)c3ccccc3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-bromo-1-phenylethanone and isolated brown gum (0.8 mg, 5%). MS (m/e): 401.4 (MH$^+$).

Example 28

5-tert-Butyl-2-[(R)-1-(2-chloro-phenyl)-ethyl]-7-(3,3-difluoro-pyrrolidin-1-yl)-2H-[1,2,3]triazolo[4,5-d]pyrimidine

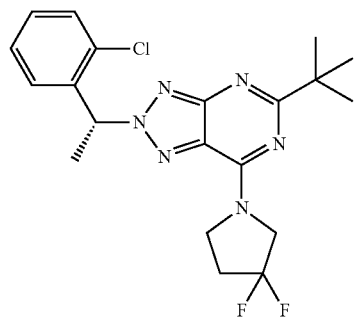 [SMILES: C[C@H](c1ccccc1Cl)n1nc2nc(C(C)(C)C)nc(N3CCC(F)(F)C3)c2n1]

To a solution of 5-tert-butyl-7-(3,3-difluoropyrrolidin-1-yl)-3H-[1,2,3]triazolo[4,5-d]pyrimidine (41.3 µmol), (S)-1-(2-chlorophenyl)ethanol (12.9 mg, 82.6 µmol) and PPh₃ (21.7 mg, 82.6 µmol) in THF (250 µL) was added DEAD (13.1 µL, 82.6 µmol) at 0° C. After being stirred at the room temperature for 2 h, the reaction mixture was directly purified by preparative HPLC (column: Gemini 5 um C18 110A 75×30 mm. mobile phase: water (0.05% Et₃N): acetonitrile 50:50% to 5:95%. WL: 300 nm Flow: 30 mL/min.) to afford the title compound as white solid (3.5 mg, 20%). MS (m/e): 421.4 (MH⁺).

Example 29

5-tert-Butyl-2-[(S)-1-(2-chloro-phenyl)-ethyl]-7-(3,3-difluoro-pyrrolidin-1-yl)-2H-[1,2,3]triazolo[4,5-d]pyrimidine

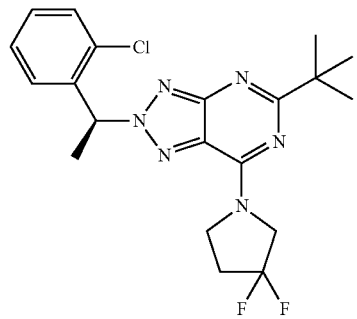 [SMILES: C[C@@H](c1ccccc1Cl)n1nc2nc(C(C)(C)C)nc(N3CCC(F)(F)C3)c2n1]

In analogy to the procedure described for the synthesis of 5-tert-butyl-2-[(R)-1-(2-chloro-phenyl)-ethyl]-7-(3,3-difluoro-pyrrolidin-1-yl)-2H-[1,2,3]triazolo[4,5-d]pyrimidine (example 28), the title compound was prepared from 5-tert-butyl-7-(3,3-difluoropyrrolidin-1-yl)-3H-[1,2,3]triazolo[4,5-d]pyrimidine and (R)-1-(2-chlorophenyl)ethanol and isolated as white solid (3.7 mg, 21%). MS (m/e): 421.4 (MH⁺).

Example 30

5-tert-Butyl-2-(2-chloro-3-fluoro-benzyl)-7-(3,3-difluoro-pyrrolidin-1-yl)-2H-[1,2,3]triazolo[4,5-d]pyrimidine

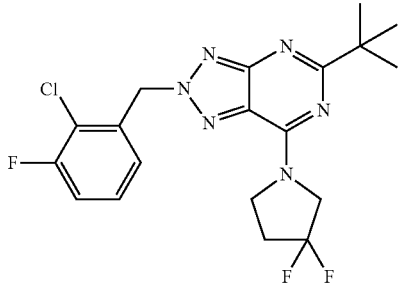 [SMILES: CC(C)(C)c1nc(N2CCC(F)(F)C2)c2nn(Cc3cccc(F)c3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(bromomethyl)-2-chloro-3-fluorobenzene and isolated as light-yellow gums (4.9 mg, 28%). MS (m/e): 425.3 (MH⁺).

Example 31

5-tert-Butyl-2-(2-chloro-5-fluoro-benzyl)-7-(3,3-difluoro-pyrrolidin-1-yl)-2H-[1,2,3]triazolo[4,5-d]pyrimidine

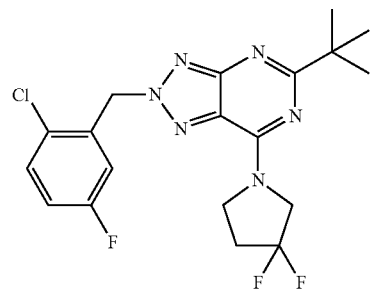 [SMILES: CC(C)(C)c1nc(N2CCC(F)(F)C2)c2nn(Cc3cc(F)ccc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(bromomethyl)-1-chloro-4-fluorobenzene and isolated as light-yellow gum (4.0 mg, 23%). MS (m/e): 425.3 (MH⁺).

Example 32

5-tert-Butyl-7-(3,3-difluoro-pyrrolidin-1-yl)-2-oxetan-3-yl-2H-[1,2,3]triazolo[4,5-d]pyrimidine

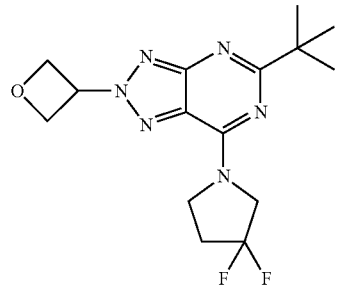 [SMILES: CC(C)(C)c1nc(N2CCC(F)(F)C2)c2nn(C3COC3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-bromooxetane and isolated as light-brown solid (2.8 mg, 20%). MS (m/e): 339.3 (MH⁺).

Example 33

5-tert-Butyl-2-(2,6-dichloro-3-fluoro-benzyl)-7-(3,3-difluoro-pyrrolidin-1-yl)-2H-[1,2,3]triazolo[4,5-d]pyrimidine

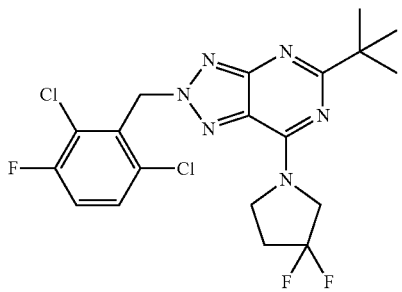 [SMILES: CC(C)(C)c1nc(N2CCC(F)(F)C2)c2nn(Cc3c(Cl)ccc(F)c3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(bromomethyl)-1,3-dichloro-4-fluorobenzene and isolated as white solid. MS (m/e): 459.2 (MH⁺).

Example 34

5-tert-Butyl-2-(2-chloro-pyridin-3-ylmethyl)-7-(3,3-difluoro-pyrrolidin-1-yl)-2H-[1,2,3]triazolo[4,5-d]pyrimidine

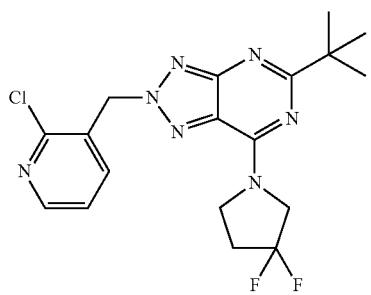 [SMILES: CC(C)(C)c1nc(N2CCC(F)(F)C2)c2nn(Cc3cccnc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-(bromomethyl)-2-chloropyridine hydrobromide and isolated as light yellow gum. MS (m/e): 408.3 (MH⁺).

Example 35

5-tert-Butyl-2-(4-chloro-pyridin-3-ylmethyl)-7-(3,3-difluoro-pyrrolidin-1-yl)-2H-[1,2,3]triazolo[4,5-d]pyrimidine

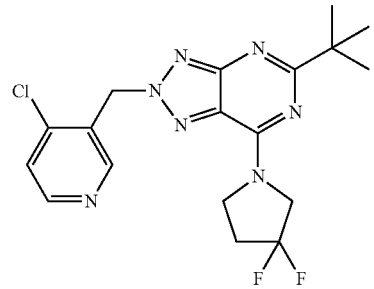 [SMILES: CC(C)(C)c1nc(N2CCC(F)(F)C2)c2nn(Cc3cnccc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 4-chloro-3-(chloromethyl)pyridine and isolated as light yellow gum. MS (m/e): 408.3 (MH⁺).

Example 36

5-tert-Butyl-2-(3-chloro-pyridin-2-ylmethyl)-7-(3,3-difluoro-pyrrolidin-1-yl)-2H-[1,2,3]triazolo[4,5-d]pyrimidine

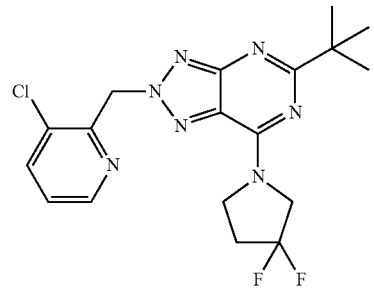 [SMILES: CC(C)(C)c1nc(N2CCC(F)(F)C2)c2nn(Cc3ncccc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-chloro-2-(chloromethyl)pyridine and isolated as light brown gum. MS (m/e): 408.3 (MH⁺).

Example 37

5-tert-Butyl-2-(2,5-dichloro-pyridin-3-ylmethyl)-7-(3,3-difluoro-pyrrolidin-1-yl)-2H-[1,2,3]triazolo[4,5-d]pyrimidine

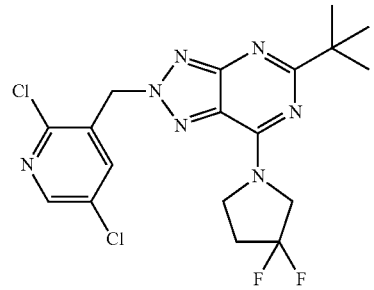 [SMILES: CC(C)(C)c1nc(N2CCC(F)(F)C2)c2nn(Cc3cc(Cl)cnc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2,5-dichloro-3-(chloromethyl)pyridine and isolated as light yellow gum. MS (m/e): 442.3 (MH+).

Example 38

5-tert-Butyl-2-(3,6-dichloro-pyridin-2-ylmethyl)-7-(3,3-difluoro-pyrrolidin-1-yl)-2H-[1,2,3]triazolo[4,5-d]pyrimidine

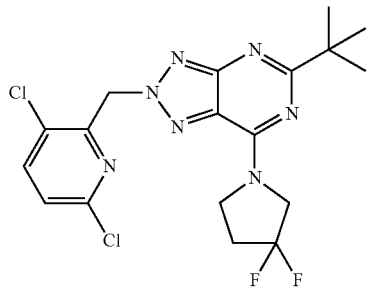 [SMILES: CC(C)(C)c1nc(N2CCC(F)(F)C2)c2nn(Cc3nc(Cl)ccc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3,6-dichloro-2-(chloromethyl)pyridine and isolated as light brown gum. MS (m/e): 442.3 (MH+).

Example 39

5-tert-Butyl-7-(3,3-difluoro-pyrrolidin-1-yl)-2-(4-methyl-furazan-3-ylmethyl)-2H-[1,2,3]triazolo[4,5-d]pyrimidine

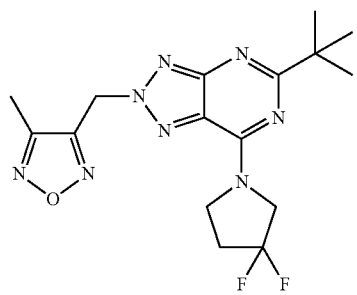 [SMILES: Cc1nonc1Cn1nc2nc(C(C)(C)C)nc(N3CCC(F)(F)C3)c2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-(bromomethyl)-4-methyl-1,2,5-oxadiazole and isolated as light yellow gum. MS (m/e): 379.3 (MH+).

Example 40

5-tert-Butyl-7-(3,3-difluoro-pyrrolidin-1-yl)-2-(3-methyl-[1,2,4]oxadiazol-5-ylmethyl)-2H-[1,2,3]triazolo[4,5-d]pyrimidine

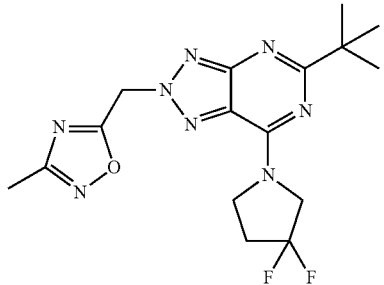 [SMILES: Cc1noc(Cn2nc3nc(C(C)(C)C)nc(N4CCC(F)(F)C4)c3n2)n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 5-(chloromethyl)-3-methyl-1,2,4-oxadiazole and isolated as light yellow gum. MS (m/e): 379.3 (MH+).

Example 41

5-tert-Butyl-2-[2-(2-chloro-phenyl)-ethyl]-7-(3,3-difluoro-pyrrolidin-1-yl)-2H-[1,2,3]triazolo[4,5-d]pyrimidine

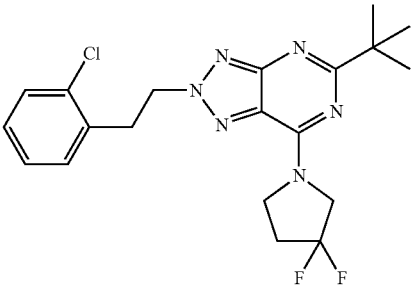 [SMILES: CC(C)(C)c1nc(N2CCC(F)(F)C2)c2nn(CCc3ccccc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(2-bromoethyl)-2-chlorobenzene and isolated as light yellow gum. MS (m/e): 421.3 (MH+).

Example 42

5-tert-Butyl-2-[2-(3-chloro-phenyl)-ethyl]-7-(3,3-difluoro-pyrrolidin-1-yl)-2H-[1,2,3]triazolo[4,5-d]pyrimidine

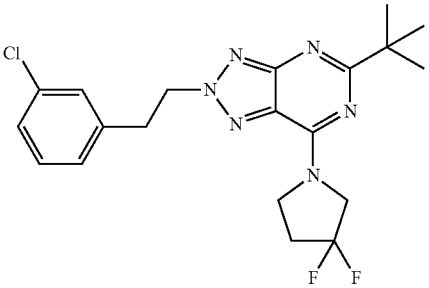 [SMILES: CC(C)(C)c1nc(N2CCC(F)(F)C2)c2nn(CCc3cccc(Cl)c3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(2-bromoethyl)-3-chlorobenzene and isolated as light yellow gum. MS (m/e): 421.3 (MH⁺).

Example 43

5-tert-Butyl-2-[2-(4-chloro-phenyl)-ethyl]-7-(3,3-difluoro-pyrrolidin-1-yl)-2H-[1,2,3]triazolo[4,5-d]pyrimidine

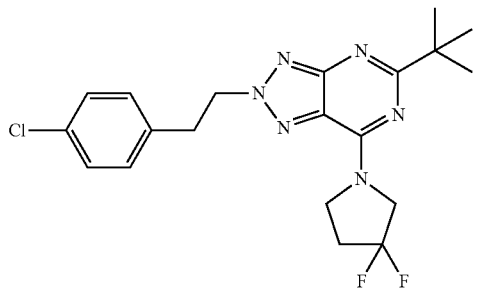 [SMILES: CC(C)(C)c1nc(N2CCC(F)(F)C2)c2nn(CCc3ccc(Cl)cc3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(2-bromoethyl)-4-chlorobenzene and isolated as white solid. MS (m/e): 421.3 (MH⁺).

Example 44

5-tert-Butyl-2-(2,4-dichloro-pyridin-3-ylmethyl)-7-(3,3-difluoro-pyrrolidin-1-yl)-2H-[1,2,3]triazolo[4,5-d]pyrimidine

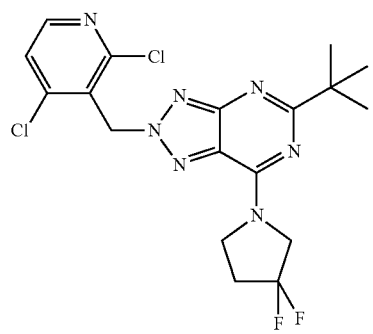 [SMILES: CC(C)(C)c1nc(N2CCC(F)(F)C2)c2nn(Cc3c(Cl)ccnc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-(bromomethyl)-2,4-dichloropyridine hydrobromide and isolated as light green solid. MS (m/e): 442.3 (MH⁺).

Example 45

5-tert-Butyl-7-(3,3-difluoro-pyrrolidin-1-yl)-2-(R)-tetrahydro-furan-3-yl-2H-[1,2,3]triazolo[4,5-d]pyrimidine

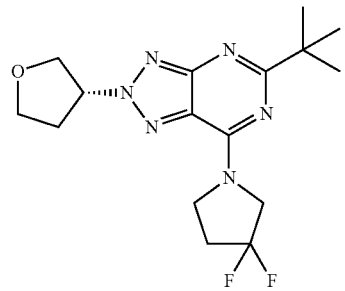 [SMILES: CC(C)(C)c1nc(N2CCC(F)(F)C2)c2nn([C@@H]3CCOC3)nc2n1]

A mixture of 5-tert-butyl-7-(3,3-difluoropyrrolidin-1-yl)-3H-[1,2,3]triazolo[4,5-d]pyrimidine (11.6 mg, 41.1 μmol), (S)-tetrahydrofuran-3-ol (7.24 mg, 6.6 μl, 82.2 μmol) and triphenylphosphine (21.6 mg, 82.2 μmol) were combined with THF (250 μl) to give a light yellow solution. To the solution was added DEAD (14.3 mg, 13.0 μl, 82.2 μmol) at 0° C. The reaction mixture was stirred at r.t. for 4 h. The crude material was purified by preparative HPLC on reversed phase eluting with a gradient formed from acetonitrile, water and NEt₃. The product containing fractions were evaporated to yield 3.1 mg (21%) of the title compound as colorless gum. MS (m/e): 353.3 (MH⁺).

Example 46

5-tert-Butyl-7-(3,3-difluoro-pyrrolidin-1-yl)-2-(S)-tetrahydro-furan-3-yl-2H-[1,2,3]triazolo[4,5-d]pyrimidine

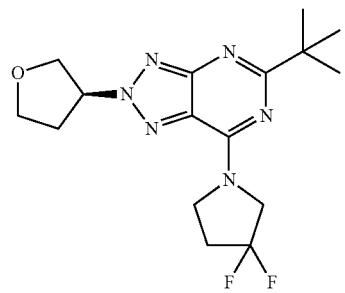 [SMILES: CC(C)(C)c1nc(N2CCC(F)(F)C2)c2nn([C@H]3CCOC3)nc2n1]

In analogy to the procedure described for the synthesis of 5-tert-Butyl-7-(3,3-difluoro-pyrrolidin-1-yl)-2-(R)-tetrahydro-furan-3-yl-2H-[1,2,3]triazolo[4,5-d]pyrimidine (example 45) the title compound was prepared from 5-tert-butyl-7-(3,3-difluoropyrrolidin-1-yl)-3H-[1,2,3]triazolo[4,5-d]pyrimidine and (R)-tetrahydrofuran-3-ol as colorless gum. MS (m/e): 353.3 (MH⁺)

Example 47

2-[5-tert-Butyl-7-(3,3-difluoro-pyrrolidin-1-yl)-[1,2,3]triazolo[4,5-d]pyrimidin-2-yl]-1-(2-chloro-phenyl)-ethanone

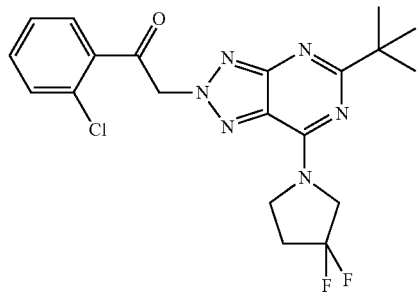 [SMILES: CC(C)(C)c1nc(N2CCC(F)(F)C2)c2nn(CC(=O)c3ccccc3Cl)nc2n1]

A mixture of 5-tert-butyl-7-(3,3-difluoropyrrolidin-1-yl)-3H-[1,2,3]triazolo[4,5-d]pyrimidine (11.6 mg, 41.1 µmol), 2-bromo-1-(2-chlorophenyl)ethanone (11.5 mg, 7.19 µl, 49.3 µmol) and DIPEA (10.6 mg, 14.4 µl, 82.2 µmol) were combined with DCM (250 µl) to give a light yellow solution. The reaction mixture was stirred at r.t. for 4 h and purified by preparative HPLC on reversed phase eluting with a gradient formed from acetonitrile, water and NEt$_3$. The product containing fractions were evaporated to yield 1.9 mg (11%) of the title compound as yellow gum. MS (m/e): 435.3 (MH$^+$).

Example 48

5-tert-Butyl-2-(2,3-dichloro-6-fluoro-benzyl)-7-(3,3-difluoro-pyrrolidin-1-yl)-2H-[1,2,3]triazolo[4,5-d]pyrimidine

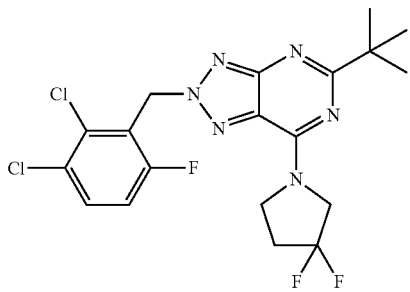 [SMILES: CC(C)(C)c1nc(N2CCC(F)(F)C2)c2nn(Cc3c(F)ccc(Cl)c3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(bromomethyl)-3,4-dichloro-1-fluorobenzene and isolated as white solid. MS (m/e): 459.3 (MH$^+$).

Example 49

5-tert-Butyl-7-(3,3-difluoro-pyrrolidin-1-yl)-2-(2-methanesulfonyl-benzyl)-2H-[1,2,3]triazolo[4,5-d]pyrimidine

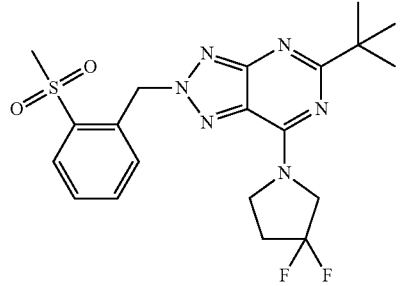 [SMILES: CC(C)(C)c1nc(N2CCC(F)(F)C2)c2nn(Cc3ccccc3S(C)(=O)=O)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(bromomethyl)-2-(methylsulfonyl)benzene and isolated as white solid. MS (m/e): 451.3 (MH$^+$).

Example 50

5-tert-Butyl-7-(3,3-difluoro-pyrrolidin-1-yl)-2-(2-pyridin-2-yl-ethyl)-2H-[1,2,3]triazolo[4,5-d]pyrimidine

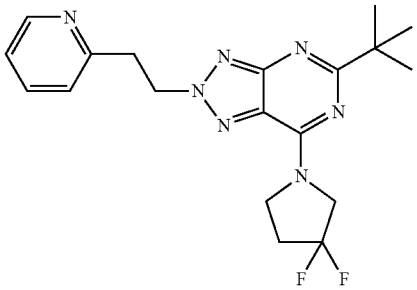 [SMILES: CC(C)(C)c1nc(N2CCC(F)(F)C2)c2nn(CCc3ccccn3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(2-bromoethyl)pyridine hydrobromide and isolated as colorless gum. MS (m/e): 388.3 (MH$^+$).

Example 51

5-tert-Butyl-7-(3,3-difluoro-pyrrolidin-1-yl)-2-(3-methyl-oxetan-3-ylmethyl)-2H-[1,2,3]triazolo[4,5-d]pyrimidine

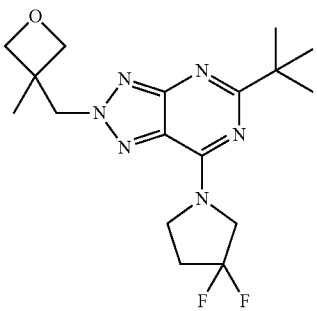 [SMILES: CC1(Cn2nc3nc(C(C)(C)C)nc(N4CCC(F)(F)C4)c3n2)COC1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-(iodomethyl)-3-methyloxetane and isolated as white solid. MS (m/e): 367.3 (MH$^+$).

Example 52

2-[5-tert-Butyl-7-(3,3-difluoro-pyrrolidin-1-yl)-[1,2,3]triazolo[4,5-d]pyrimidin-2-yl]-1-(3-chloro-phenyl)-ethanone

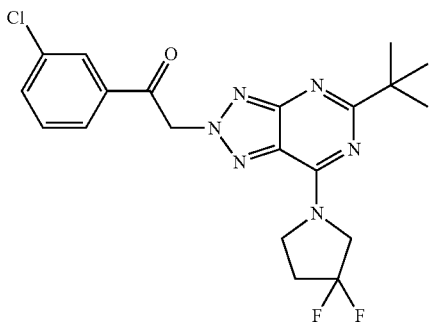 [SMILES: CC(C)(C)c1nc(N2CCC(F)(F)C2)c2nn(CC(=O)c3cccc(Cl)c3)nc2n1]

In analogy to the procedure described for the synthesis of 2-[5-tert-Butyl-7-(3,3-difluoro-pyrrolidin-1-yl)-[1,2,3]triazolo[4,5-d]pyrimidin-2-yl]-1-(2-chloro-phenyl)-ethanone (example 47), the title compound was prepared from 5-tert-butyl-7-(3,3-difluoropyrrolidin-1-yl)-3H-[1,2,3]triazolo[4,5-d]pyrimidine and 2-bromo-1-(3-chlorophenyl)ethanone and isolated as yellow solid. MS (m/e): 435.3 (MH$^+$).

Example 53

2-[5-tert-Butyl-7-(3,3-difluoro-pyrrolidin-1-yl)-[1,2,3]triazolo[4,5-d]pyrimidin-2-yl]-1-(4-chloro-phenyl)-ethanone

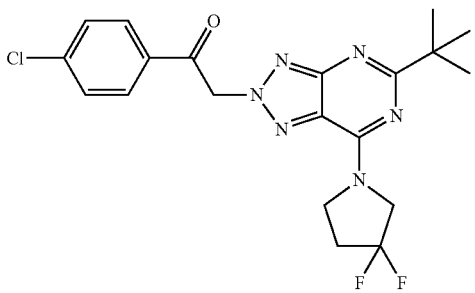 [SMILES: CC(C)(C)c1nc(N2CCC(F)(F)C2)c2nn(CC(=O)c3ccc(Cl)cc3)nc2n1]

In analogy to the procedure described for the synthesis of 2-[5-tert-Butyl-7-(3,3-difluoro-pyrrolidin-1-yl)-[1,2,3]triazolo[4,5-d]pyrimidin-2-yl]-1-(2-chloro-phenyl)-ethanone (example 47), the title compound was prepared from 5-tert-butyl-7-(3,3-difluoropyrrolidin-1-yl)-3H-[1,2,3]triazolo[4,5-d]pyrimidine and 2-bromo-1-(4-chlorophenyl)ethanone and isolated as light yellow solid. MS (m/e): 435.3 (MH$^+$).

Example 54

2-[5-tert-Butyl-7-(3,3-difluoro-pyrrolidin-1-yl)-[1,2,3]triazolo[4,5-d]pyrimidin-2-yl]-1-pyridin-3-yl-ethanone

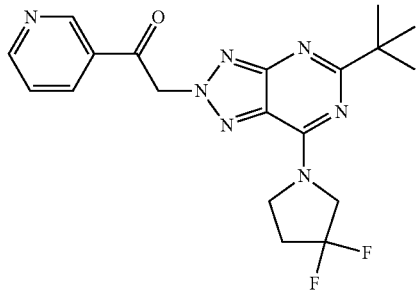 [SMILES: CC(C)(C)c1nc(N2CCC(F)(F)C2)c2nn(CC(=O)c3cccnc3)nc2n1]

In analogy to the procedure described for the synthesis of 2-[5-tert-Butyl-7-(3,3-difluoro-pyrrolidin-1-yl)-[1,2,3]triazolo[4,5-d]pyrimidin-2-yl]-1-(2-chloro-phenyl)-ethanone (example 47), the title compound was prepared from 5-tert-butyl-7-(3,3-difluoropyrrolidin-1-yl)-3H-[1,2,3]triazolo[4,5-d]pyrimidine and 2-bromo-1-(pyridin-3-yl)ethanone hydrobromide and isolated as light yellow solid. MS (m/e): 402.3 (MH$^+$).

Example 55

5-tert-Butyl-7-(3,3-difluoro-pyrrolidin-1-yl)-2-(2,3,6-trichloro-benzyl)-2H-[1,2,3]triazolo[4,5-d]pyrimidine

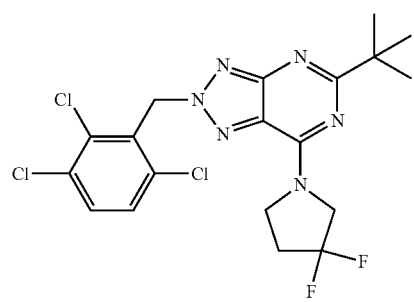 [SMILES: CC(C)(C)c1nc(N2CCC(F)(F)C2)c2nn(Cc3c(Cl)ccc(Cl)c3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(bromomethyl)-1,3,4-trichlorobenzene and isolated as light red solid. MS (m/e): 475.2 (MH$^+$).

Example 56

5-tert-Butyl-2-(2-chloro-3-trifluoromethyl-benzyl)-7-(3,3-difluoro-pyrrolidin-1-yl)-2H-[1,2,3]triazolo[4,5-d]pyrimidine

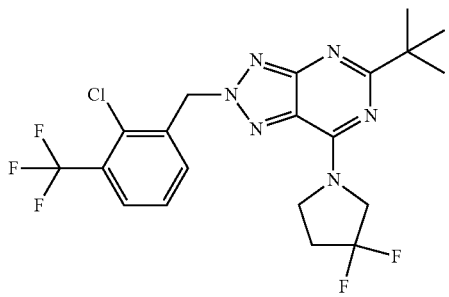 [SMILES: CC(C)(C)c1nc(N2CCC(F)(F)C2)c2nn(Cc3cccc(C(F)(F)F)c3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 1-(bromomethyl)-2-chloro-3-(trifluoromethyl)$_b$ enzene and isolated as white solid. MS (m/e): 475.3 (MH$^+$).

Example 57

5-tert-Butyl-2-(2-chloro-6-fluoro-3-methoxy-benzyl)-7-(3,3-difluoro-pyrrolidin-1-yl)-2H-[1,2,3]triazolo[4,5-d]pyrimidine

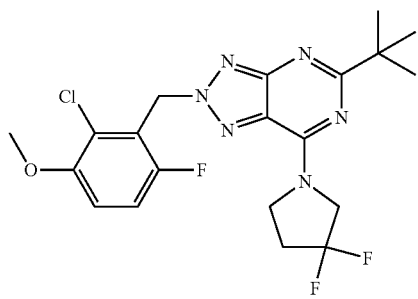 [SMILES: COc1ccc(F)c(Cn2nc3nc(C(C)(C)C)nc(N4CCC(F)(F)C4)c3n2)c1Cl]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(bromomethyl)-3-chloro-1-fluoro-4-methoxybenzene and isolated as white solid. MS (m/e): 455.3 (MH$^+$).

Example 58

5-tert-Butyl-7-(3,3-difluoro-pyrrolidin-1-yl)-2-(2-pyridin-3-yl-ethyl)-2H-[1,2,3]triazolo[4,5-d]pyrimidine

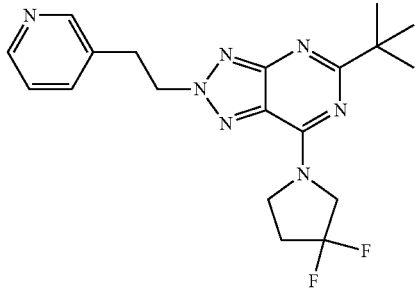 [SMILES: CC(C)(C)c1nc(N2CCC(F)(F)C2)c2nn(CCc3cccnc3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-(2-bromoethyl)pyridine hydrobromide and isolated as light yellow gum. MS (m/e): 388.3 (MH$^+$).

Example 59

5-tert-Butyl-7-(3,3-difluoro-pyrrolidin-1-yl)-2-(2-pyridin-4-yl-ethyl)-2H-[1,2,3]triazolo[4,5-d]pyrimidine

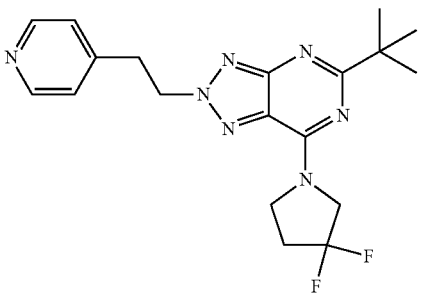 [SMILES: CC(C)(C)c1nc(N2CCC(F)(F)C2)c2nn(CCc3ccncc3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 4-(2-bromoethyl)pyridine hydrobromide and isolated as white solid. MS (m/e): 388.3 (MH$^+$).

Example 60

5-tert-Butyl-2-(2,3-dichloro-6-trifluoromethyl-benzyl)-7-(3,3-difluoro-pyrrolidin-1-yl)-2H-[1,2,3]triazolo[4,5-d]pyrimidine

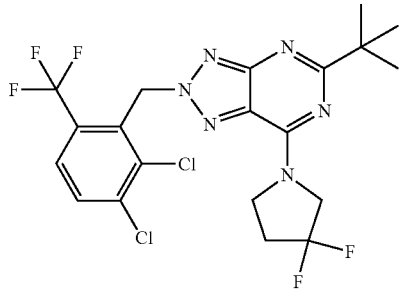 [SMILES: CC(C)(C)c1nc(N2CCC(F)(F)C2)c2nn(Cc3c(C(F)(F)F)ccc(Cl)c3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(bromomethyl)-3,4-dichloro-1-(trifluoromethyl)benzene and isolated as white solid. MS (m/e): 509.3 (MH+).

Example 61

5-tert-Butyl-2-(3,4-dichloro-pyridin-2-ylmethyl)-7-(3,3-difluoro-pyrrolidin-1-yl)-2H-[1,2,3]triazolo[4,5-d]pyrimidine

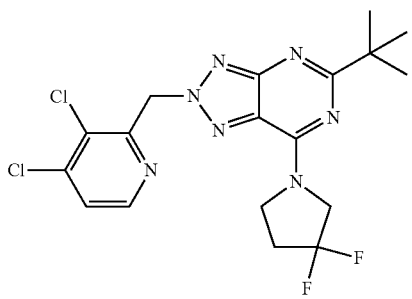 [SMILES: CC(C)(C)c1nc(N2CCC(F)(F)C2)c2nn(Cc3nccc(Cl)c3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(bromomethyl)-3,4-dichloropyridine hydrobromide and isolated as light yellow gum. MS (m/e): 442.3 (MH+).

Example 62

5-tert-Butyl-7-(3,3-difluoro-pyrrolidin-1-yl)-2-(1,1-dioxo-1λ6-thietan-3-yl)-2H-[1,2,3]triazolo[4,5-d]pyrimidine

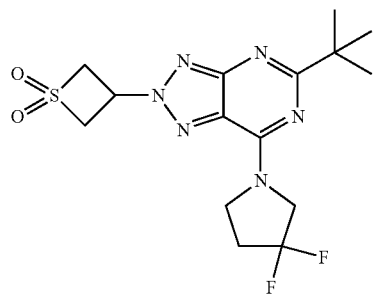 [SMILES: CC(C)(C)c1nc(N2CCC(F)(F)C2)c2nn(C3CS(=O)(=O)C3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-bromo-thietane 1,1-dioxide and isolated as white solid. MS (m/e): 387.3 (MH+).

Example 63

5-tert-Butyl-7-(3,3-difluoro-pyrrolidin-1-yl)-2-(1,1-dioxo-tetrahydro-1λ6-thiophen-3-yl)-2H-[1,2,3]triazolo[4,5-d]pyrimidine

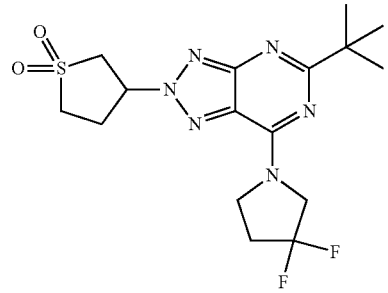 [SMILES: CC(C)(C)c1nc(N2CCC(F)(F)C2)c2nn(C3CCS(=O)(=O)C3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-bromo-tetrahydro-thiophene 1,1-dioxide and isolated as white solid. MS (m/e): 401.3 (MH+).

Example 64

2-[5-tert-Butyl-7-(3,3-difluoro-pyrrolidin-1-yl)-[1,2,3]triazolo[4,5-d]pyrimidin-2-yl]-1-pyridin-2-yl-ethanone

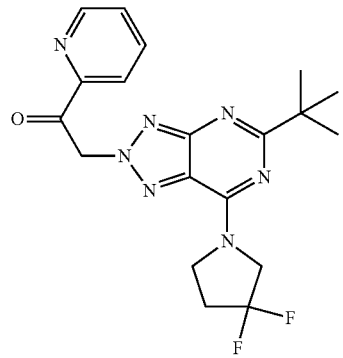 [SMILES: CC(C)(C)c1nc(N2CCC(F)(F)C2)c2nn(CC(=O)c3ccccn3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-bromo-1-(pyridin-2-yl)ethanone hydrobromide and isolated as brown solid. MS (m/e): 402.3 (MH+).

Example 65

5-tert-Butyl-7-(3,3-difluoro-pyrrolidin-1-yl)-2-(5-methyl-[1,3,4]oxadiazol-2-ylmethyl)-2H-[1,2,3]triazolo[4,5-d]pyrimidine

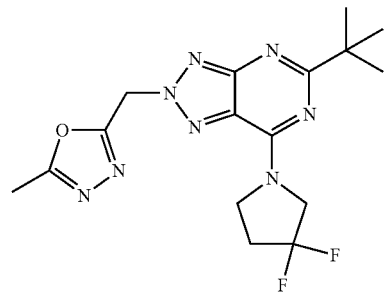 [SMILES: Cc1nnc(Cn2nc3nc(C(C)(C)C)nc(N4CCC(F)(F)C4)c3n2)o1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 2-(chloromethyl)-5-methyl-1,3,4-oxadiazole and isolated as colorless gum. MS (m/e): 379.3 (MH$^+$).

Example 66

5-tert-Butyl-2-(3-chloro-pyridin-4-ylmethyl)-7-(3,3-difluoro-pyrrolidin-1-yl)-2H-[1,2,3]triazolo[4,5-d]pyrimidine

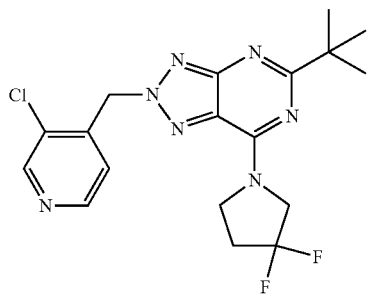 [SMILES: CC(C)(C)c1nc(N2CCC(F)(F)C2)c2nn(Cc3ccncc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 4-(bromomethyl)-3-chloropyridine hydrobromide and isolated as yellow gum. MS (m/e): 408.3 (MH$^+$).

Example 67

5-tert-Butyl-7-(3,3-difluoro-pyrrolidin-1-yl)-2-(5-methyl-[1,2,4]oxadiazol-3-ylmethyl)-2H-[1,2,3]triazolo[4,5-d]pyrimidine

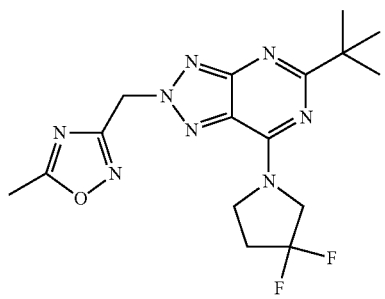 [SMILES: Cc1nc(Cn2nc3nc(C(C)(C)C)nc(N4CCC(F)(F)C4)c3n2)no1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-(chloromethyl)-5-methyl-1,2,4-oxadiazole and isolated as yellow gum. MS (m/e): 379.3 (MH$^+$).

Example 68

5-tert-Butyl-7-(3,3-difluoro-pyrrolidin-1-yl)-2-(1-methyl-1H-tetrazol-5-ylmethyl)-2H-[1,2,3]triazolo[4,5-d]pyrimidine

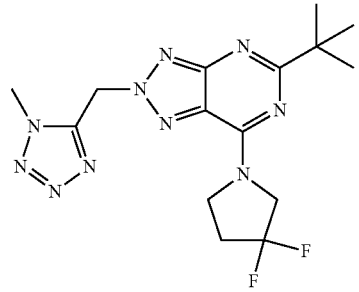 [SMILES: Cn1nnnc1Cn1nc2nc(C(C)(C)C)nc(N3CCC(F)(F)C3)c2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 5-(chloromethyl)-1-methyl-1H-tetrazole and isolated as white solid. MS (m/e): 379.3 (MH$^+$).

Example 69

5-tert-Butyl-7-(3,3-difluoro-pyrrolidin-1-yl)-2-(2-methyl-2H-[1,2,4]triazol-3-ylmethyl)-2H-[1,2,3]triazolo[4,5-d]pyrimidine

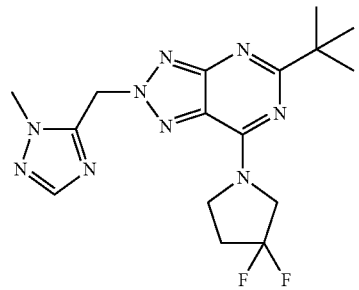 [SMILES: Cn1ncnc1Cn1nc2nc(C(C)(C)C)nc(N3CCC(F)(F)C3)c2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 5-(chloromethyl)-1-methyl-1H-1,2,4-triazole hydrochloride and isolated as colorless gum. MS (m/e): 378.3 (MH$^+$).

Example 70

5-tert-Butyl-7-(3,3-difluoro-pyrrolidin-1-yl)-2-(5-methanesulfonyl-4-methyl-4H-[1,2,4]triazol-3-ylmethyl)-2H-[1,2,3]triazolo[4,5-d]pyrimidine

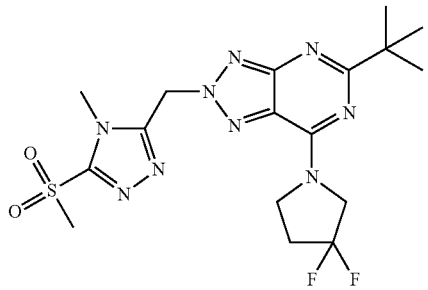 [SMILES: Cn1c(Cn2nc3nc(C(C)(C)C)nc(N4CCC(F)(F)C4)c3n2)nnc1S(C)(=O)=O]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-(iodomethyl)-4-methyl-5-(methylsulfonyl)-4H-1,2,4-triazole and isolated as white solid. MS (m/e): 456.3 (MH⁺).

Example 71

{3-[5-tert-Butyl-7-(3,3-difluoro-pyrrolidin-1-yl)-[1,2,3]triazolo[4,5-d]pyrimidin-2-ylmethyl]-5-chloro-pyridin-4-yl}-dimethyl-amine

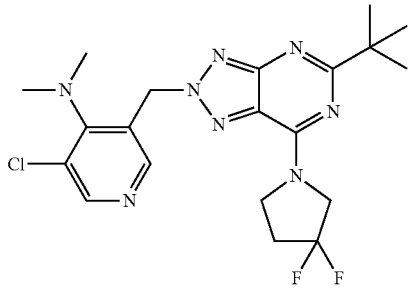 [SMILES: CN(C)c1c(Cl)cncc1Cn1nc2nc(C(C)(C)C)nc(N3CCC(F)(F)C3)c2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-(bromomethyl)-5-chloro-N,N-dimethylpyridin-4-amine hydrobromide and isolated as light yellow gum. MS (m/e): 451.4 (MH⁺).

Example 72

5-tert-Butyl-7-(3,3-difluoro-pyrrolidin-1-yl)-2-(3-trifluoromethyl-1H-pyrazol-4-ylmethyl)-2H-[1,2,3]triazolo[4,5-d]pyrimidine

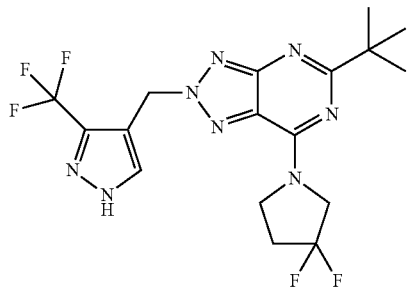 [SMILES: CC(C)(C)c1nc(N2CCC(F)(F)C2)c2nn(Cc3c[nH]nc3C(F)(F)F)nc2n1]

a) 5-tert-Butyl-7-(3,3-difluoro-pyrrolidin-1-yl)-2-(3-trifluoromethyl-1-trityl-1H-pyrazol-4-ylmethyl)-2H-[1,2,3]triazolo[4,5-d]pyrimidine

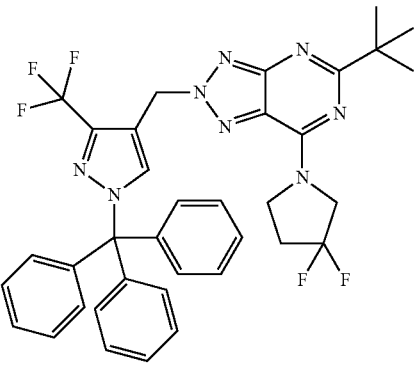 [SMILES: CC(C)(C)c1nc(N2CCC(F)(F)C2)c2nn(Cc3cn(C(c4ccccc4)(c4ccccc4)c4ccccc4)nc3C(F)(F)F)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 4-(bromomethyl)-3-(trifluoromethyl)-1-trityl-1H-pyrazole and used in the consecutive step without further purification.

b) 5-tert-Butyl-7-(3,3-difluoro-pyrrolidin-1-yl)-2-(3-trifluoromethyl-1H-pyrazol-4-ylmethyl)-2H-[1,2,3]triazolo[4,5-d]pyrimidine The crude 5-tert-Butyl-7-(3,3-difluoro-pyrrolidin-1-yl)-2-(3-trifluoromethyl-1-trityl-1H-pyrazol-4-ylmethyl)-2H-[1,2,3]triazolo[4,5-d]pyrimidine and triethylsilane in TFA was stirred at r.t. for 3 h. The reaction mixture was concentrated in vacuo and purified by preparative HPLC on reversed phase eluting with a gradient formed from acetonitrile, water and NEt₃. The product containing fractions were evaporated to yield the title compound as white solid. MS (m/e): 431.3 (MH⁺)

Example 73

(S)-1-[5-tert-Butyl-2-(4-methyl-furazan-3-ylmethyl)-2H-[1,2,3]triazolo[4,5-d]pyrimidin-7-yl]-pyrrolidin-3-ol

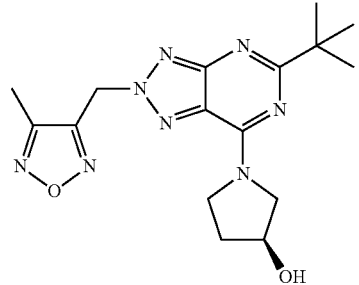 [SMILES: Cc1nonc1Cn1nc2nc(C(C)(C)C)nc(N3CC[C@H](O)C3)c2n1]

a) (S)-1-[5-tert-Butyl-3-(4-methoxy-benzyl)-3H-[1,2,3]triazolo[4,5-d]pyrimidin-7-yl]-pyrrolidin-3-ol

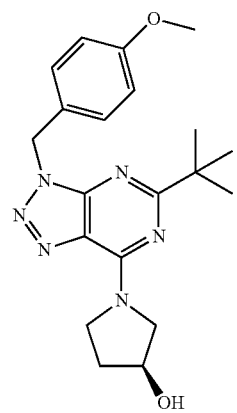 [SMILES: COc1ccc(Cn2nnc3c(N4CC[C@H](O)C4)nc(C(C)(C)C)nc32)cc1]

In analogy to the procedure described for the synthesis of 4-(5-tert-Butyl-3-(4-methoxybenzyl)-3H-[1,2,3]triazolo[4,5-d]pyrimidin-7-yl)morpholine (example 1, step c) the title compound was prepared from 5-tert-Butyl-3-(4-methoxy-benzyl)-3H-[1,2,3]triazolo[4,5-d]pyrimidin-7(4H)-one after chlorination with POCl₃ and nucleophilic substitution with (S)-pyrrolidin-3-ol as light green viscous oil which was used in the consecutive step without further purification.

b) Trifluoro-acetic acid (S)-1-(5-tert-butyl-3H-[1,2,3]triazolo[4,5-d]pyrimidin-7-yl)-pyrrolidin-3-yl-ester

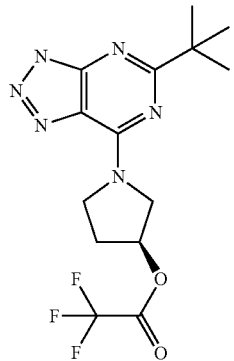 [SMILES: CC(C)(C)c1nc(N2CC[C@H](OC(=O)C(F)(F)F)C2)c2nn[nH]c2n1]

A mixture of (S)-1-[5-tert-Butyl-3-(4-methoxy-benzyl)-3H-[1,2,3]triazolo[4,5-d]pyrimidin-7-yl]-pyrrolidin-3-ol and triethylsilane in TFA was heated to 70° C. for 22 h and evaporated to dryness. The residue was used without further purification in the consecutive step.

c) (S)-1-[5-tert-Butyl-2-(4-methyl-furazan-3-ylmethyl)-2H-[1,2,3]triazolo[4,5-d]pyrimidin-7-yl]-pyrrolidin-3-ol In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from Trifluoro-acetic acid (S)-1-(5-tert-butyl-3H-[1,2,3]triazolo[4,5-d]pyrimidin-7-yl)-pyrrolidin-3-yl-ester and 3-(bromomethyl)-4-methyl-1,2,5-oxadiazole. After completion of the substitution reaction methanol was added and the mixture was stirred for 1 h at room temperature and subsequently subjected to purification with preparative HPLC on reversed phase eluting with a gradient formed from acetonitrile, water and NEt₃. After evaporation of the product containing fractions the title compound was isolated as light-yellow gum. MS (m/e): 359.3 (MH⁺).

Example 74

(S)-1-[5-tert-Butyl-2-(3-methyl-[1,2,4]oxadiazol-5-ylmethyl)-2H-[1,2,3]triazolo[4,5-d]pyrimidin-7-yl]-pyrrolidin-3-ol

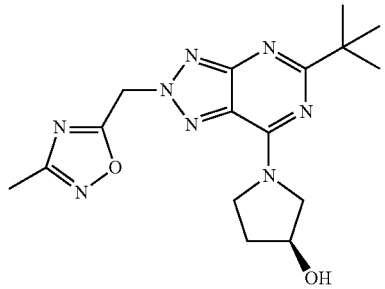 [SMILES: Cc1noc(Cn2nc3nc(C(C)(C)C)nc(N4CC[C@H](O)C4)c3n2)n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 5-(chloromethyl)-3-methyl-1,2,4-oxadiazole and isolated as brown gum. MS (m/e): 359.3 (MH⁺).

Example 75

(S)-1-[5-tert-Butyl-2-(3-chloro-pyridin-2-ylmethyl)-2H-[1,2,3]triazolo[4,5-d]pyrimidin-7-yl]-pyrrolidin-3-ol

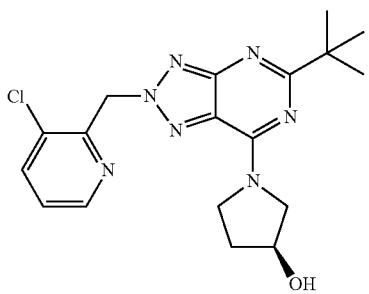 [SMILES: CC(C)(C)c1nc(N2CC[C@H](O)C2)c2nn(Cc3ncccc3Cl)nc2n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 3-chloro-2-(chloromethyl)pyridine and isolated as light yellow gum. MS (m/e): 388.3 (MH⁺).

Example 76

(S)-1-[5-tert-Butyl-2-(3,6-dichloro-pyridin-2-ylmethyl)-2H-[1,2,3]triazolo[4,5-d]pyrimidin-7-yl]-pyrrolidin-3-ol

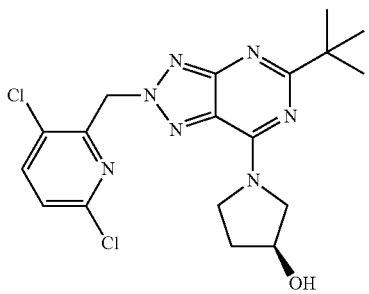 [SMILES: CC(C)(C)c1nc(N2CC[C@H](O)C2)c2nn(Cc3nc(Cl)ccc3Cl)nc2n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 3,6-dichloro-2-(chloromethyl)pyridine and isolated as light yellow gum. MS (m/e): 422.3 (MH⁺).

Example 77

(S)-1-[5-tert-Butyl-2-(2-chloro-pyridin-3-ylmethyl)-2H-[1,2,3]triazolo[4,5-d]pyrimidin-7-yl]-pyrrolidin-3-ol

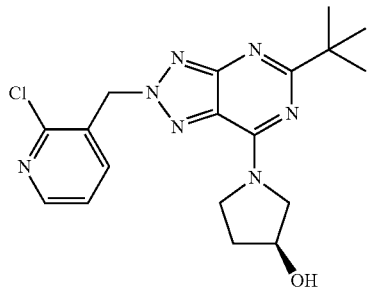 [SMILES: CC(C)(C)c1nc(N2CC[C@H](O)C2)c2nn(Cc3cccnc3Cl)nc2n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 3-(bromomethyl)-2-chloropyridine hydrobromide and isolated as light brown gum. MS (m/e): 388.3 (MH+).

Example 78

(S)-1-[5-tert-Butyl-2-(2,3-dichloro-benzyl)-2H-[1,2,3]triazolo[4,5-d]pyrimidin-7-yl]-pyrrolidin-3-ol

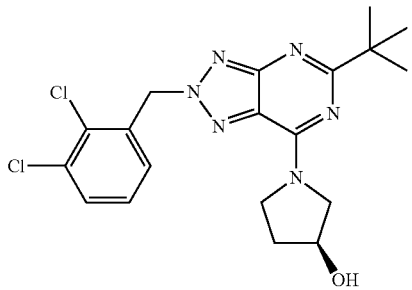 [SMILES: CC(C)(C)c1nc(N2CC[C@H](O)C2)c2nn(Cc3cccc(Cl)c3Cl)nc2n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 1-(bromomethyl)-2,3-dichlorobenzene and isolated as light brown gum. MS (m/e): 421.3 (MH+).

Example 79

(S)-1-[5-tert-Butyl-2-(2-trifluoromethyl-benzyl)-2H-[1,2,3]triazolo[4,5-d]pyrimidin-7-yl]-pyrrolidin-3-ol

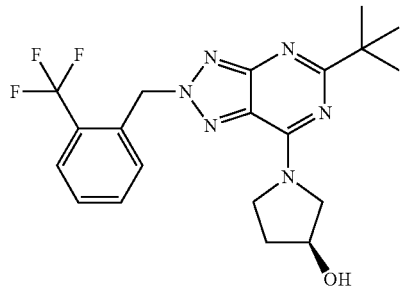 [SMILES: CC(C)(C)c1nc(N2CC[C@H](O)C2)c2nn(Cc3ccccc3C(F)(F)F)nc2n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 1-(bromomethyl)-2-(trifluoromethyl)benzene and isolated as light yellow gum. MS (m/e): 421.3 (MH+).

Example 80

(S)-1-[5-tert-Butyl-2-(2-methanesulfonyl-benzyl)-2H-[1,2,3]triazolo[4,5-d]pyrimidin-7-yl]-pyrrolidin-3-ol

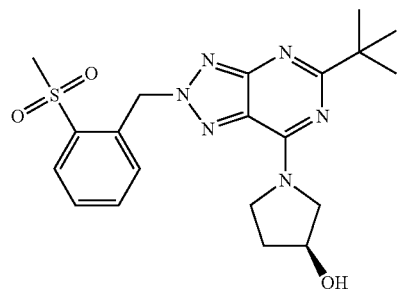 [SMILES: CC(C)(C)c1nc(N2CC[C@H](O)C2)c2nn(Cc3ccccc3S(C)(=O)=O)nc2n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 1-(bromomethyl)-2-(methylsulfonyl)benzene and isolated as white solid. MS (m/e): 431.3 (MH+).

Example 81

5-tert-Butyl-7-(3,3-difluoro-pyrrolidin-1-yl)-2-(2,5-dimethyl-2H-pyrazol-3-ylmethyl)-2H-[1,2,3]triazolo[4,5-d]pyrimidine

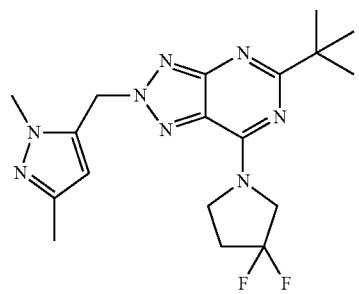 [SMILES: Cc1cc(Cn2nc3nc(C(C)(C)C)nc(N4CCC(F)(F)C4)c3n2)n(C)n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 5-(chloromethyl)-1,3-dimethyl-1H-pyrazole and isolated as light yellow gum. MS (m/e): 391.3 (MH+).

Example 82

5-tert-Butyl-7-(3,3-difluoro-pyrrolidin-1-yl)-2-(3-methyl-3H-[1,2,3]triazol-4-ylmethyl)-2H-[1,2,3]triazolo[4,5-d]pyrimidine

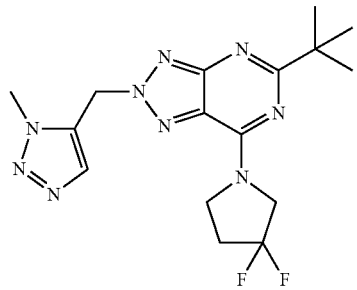 [SMILES: Cn1nncc1Cn1nc2nc(C(C)(C)C)nc(N3CCC(F)(F)C3)c2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 5-(chloromethyl)-1-methyl-1H-1,2,3-triazole hydrochloride and isolated as light yellow solid. MS (m/e): 378.3 (MH+).

Example 83

5-tert-Butyl-7-(3,3-difluoro-pyrrolidin-1-yl)-2-(4,5-dimethyl-4H-[1,2,4]triazol-3-ylmethyl)-2H-[1,2,3]triazolo[4,5-d]pyrimidine

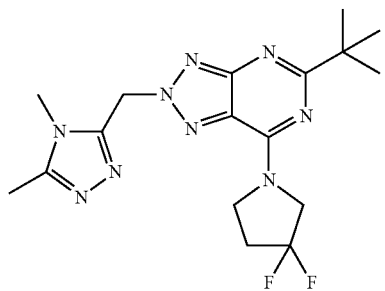 [SMILES: Cc1nnc(Cn2nc3nc(C(C)(C)C)nc(N4CCC(F)(F)C4)c3n2)n1C]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-(chloromethyl)-4,5-dimethyl-4H-1,2,4-triazole and isolated as light yellow solid. MS (m/e): 392.3 (MH+).

Example 84

5-tert-Butyl-7-(3,3-difluoro-pyrrolidin-1-yl)-2-(2-methyl-1-oxy-pyridin-3-ylmethyl)-2H-[1,2,3]triazolo[4,5-d]pyrimidine

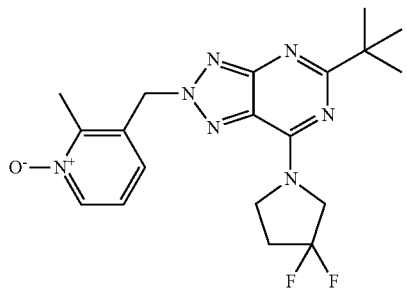 [SMILES: Cc1c(Cn2nc3nc(C(C)(C)C)nc(N4CCC(F)(F)C4)c3n2)ccc[n+]1[O-]]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 3-(chloromethyl)-2-methylpyridine 1-oxide and isolated as light yellow gum. MS (m/e): 404.3 (MH+).

Example 85

(S)-1-[5-tert-Butyl-2-(3,4-dichloro-pyridin-2-ylmethyl)-2H-[1,2,3]triazolo[4,5-d]pyrimidin-7-yl]-pyrrolidin-3-ol

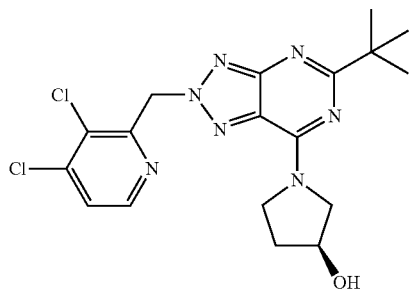 [SMILES: CC(C)(C)c1nc(N2CC[C@H](O)C2)c2nn(Cc3nccc(Cl)c3Cl)nc2n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 2-(bromomethyl)-3,4-dichloropyridine hydrobromide and isolated as white solid. MS (m/e): 422.2 (MH+).

Example 86

(S)-1-[5-tert-Butyl-2-(5-methyl-[1,2,4]oxadiazol-3-ylmethyl)-2H-[1,2,3]triazolo[4,5-d]pyrimidin-7-yl]-pyrrolidin-3-ol

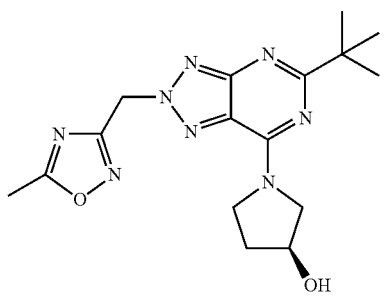 [SMILES: Cc1nc(Cn2nc3nc(C(C)(C)C)nc(N4CC[C@H](O)C4)c3n2)no1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 3-(chloromethyl)-5-methyl-1,2,4-oxadiazole and isolated as light yellow gum. MS (m/e): 359.5 (MH+).

Example 87

(S)-1-[5-tert-Butyl-2-(5-methyl-[1,3,4]oxadiazol-2-ylmethyl)-2H-[1,2,3]triazolo[4,5-d]pyrimidin-7-yl]-pyrrolidin-3-ol

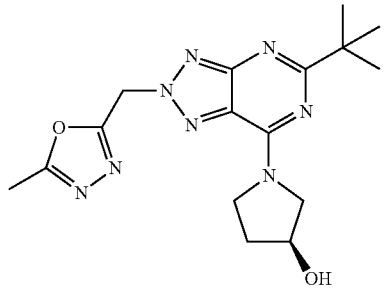 [SMILES: Cc1nnc(Cn2nc3nc(C(C)(C)C)nc(N4CC[C@H](O)C4)c3n2)o1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 2-(chloromethyl)-5-methyl-1,3,4-oxadiazole and isolated as light yellow gum. MS (m/e): 359.5 (MH$^+$).

Example 88

(S)-1-[5-tert-Butyl-2-(1-methyl-1H-tetrazol-5-ylmethyl)-2H-[1,2,3]triazolo[4,5-d]pyrimidin-7-yl]-pyrrolidin-3-ol

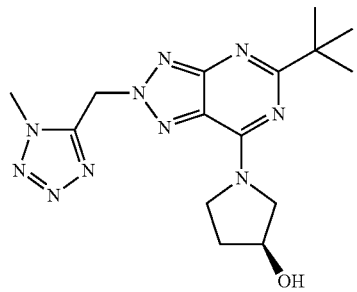 [SMILES: Cn1nnnc1Cn1nc2nc(C(C)(C)C)nc(N3CC[C@H](O)C3)c2n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 5-(chloromethyl)-1-methyl-1H-tetrazole and isolated as yellow gum. MS (m/e): 359.3 (MH$^+$).

Example 89

(S)-1-[5-tert-Butyl-2-(2-methyl-2H-[1,2,4]triazol-3-ylmethyl)-2H-[1,2,3]triazolo[4,5-d]pyrimidin-7-yl]-pyrrolidin-3-ol

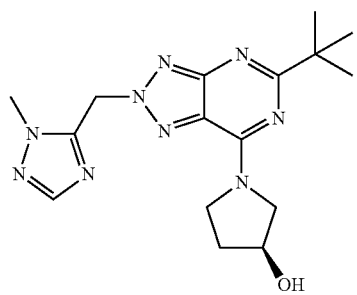 [SMILES: Cn1ncnc1Cn1nc2nc(C(C)(C)C)nc(N3CC[C@H](O)C3)c2n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 5-(chloromethyl)-1-methyl-1H-1,2,4-triazole hydrochloride and isolated as light yellow gum. MS (m/e): 358.2 (MH$^+$).

Example 90

(S)-1-[5-tert-Butyl-2-(3-methyl-3H-[1,2,3]triazol-4-ylmethyl)-2H-[1,2,3]triazolo[4,5-d]pyrimidin-7-yl]-pyrrolidin-3-ol

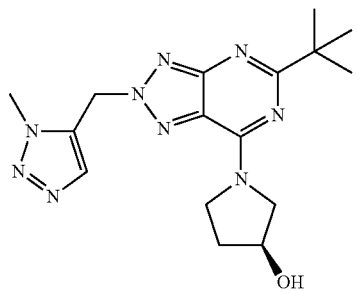 [SMILES: Cn1nncc1Cn1nc2nc(C(C)(C)C)nc(N3CC[C@H](O)C3)c2n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 5-(chloromethyl)-1-methyl-1H-1,2,3-triazole hydrochloride and isolated as light yellow gum. MS (m/e): 358.3 (MH$^+$).

Example 91

(S)-1-[5-tert-Butyl-2-(2,5-dimethyl-2H-pyrazol-3-ylmethyl)-2H-[1,2,3]triazolo[4,5-d]pyrimidin-7-yl]-pyrrolidin-3-ol

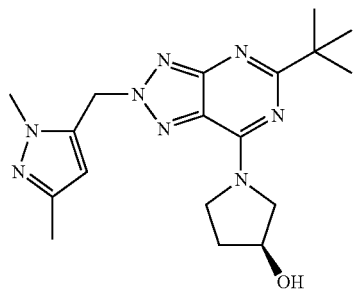 [SMILES: Cc1cc(Cn2nc3nc(C(C)(C)C)nc(N4CC[C@H](O)C4)c3n2)n(C)n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 5-(chloromethyl)-1,3-dimethyl-1H-pyrazole and isolated as light yellow gum. MS (m/e): 371.3 (MH$^+$).

Example 92

5-tert-Butyl-2-(1-cyclopropyl-1H-tetrazol-5-ylmethyl)-7-(3,3-difluoro-pyrrolidin-1-yl)-2H-[1,2,3]triazolo[4,5-d]pyrimidine

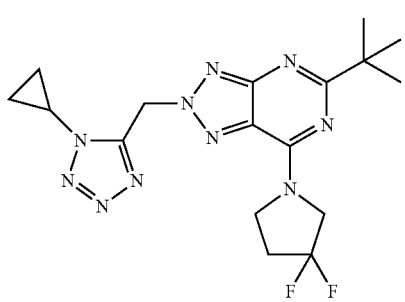 [SMILES: CC(C)(C)c1nc(N2CCC(F)(F)C2)c2nn(Cc3nnnn3C3CC3)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 5-(chloromethyl)-1-cyclopropyl-1H-tetrazole and isolated as red gum. MS (m/e): 405.3 (MH$^+$).

Example 93

(S)-1-{5-tert-Butyl-2-[2-(7-nitro-benzo[1,2,5]oxadiazol-4-ylamino)-pyridin-3-ylmethyl]-2H-[1,2,3]triazolo[4,5-d]pyrimidin-7-yl}-pyrrolidin-3-ol

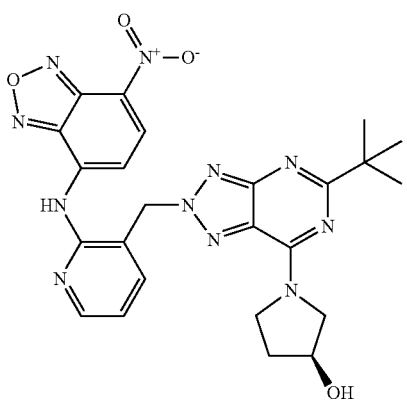 [SMILES: CC(C)(C)c1nc(N2CC[C@H](O)C2)c2nn(Cc3cccnc3Nc3ccc([N+](=O)[O-])c4nonc34)nc2n1]

A mixture of (S)-1-(5-tert-butyl-2-((2-chloropyridin-3-yl)methyl)-2H-[1,2,3]triazolo[4,5-d]pyrimidin-7-yl)pyrrolidin-3-ol (5.70 mg, 14.7 µmol) (example 75), 7-nitrobenzo[c][1,2,5]oxadiazol-4-amine (3.18 mg, 17.6 µmol), Pd$_2$(dba)$_3$ (1.35 mg, 1.47 µmol), xantphos (2.55 mg, 4.41 µmol) and Cs$_2$CO$_3$ (9.58 mg, 29.4 µmol) in dioxane (500 µl) was heated to 120° C. (microwave) and stirred for 20 min. The crude material was filtered, concentrated and purified by preparative HPLC on reversed phase eluting with a gradient formed from acetonitrile, water and NEt$_3$. After evaporation of the product containing fractions 3.1 mg (40%) of the title compound was isolated as red solid. MS (m/e): 532.4 (MH$^+$).

Example 94

(S)-1-[5-tert-Butyl-2-(1-cyclopropyl-1H-tetrazol-5-ylmethyl)-2H-[1,2,3]triazolo[4,5-d]pyrimidin-7-yl]-pyrrolidin-3-ol

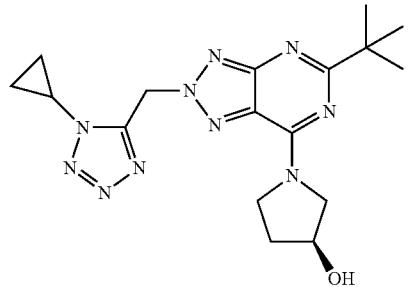 [SMILES: CC(C)(C)c1nc(N2CC[C@H](O)C2)c2nn(Cc3nnnn3C3CC3)nc2n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 5-(chloromethyl)-1-cyclopropyl-1H-tetrazole and isolated as light yellow gum. MS (m/e): 385.3 (MH$^+$).

Example 95

(S)-1-[5-tert-Butyl-2-(2,5-dimethyl-2H-[1,2,4]triazol-3-ylmethyl)-2H-[1,2,3]triazolo[4,5-d]pyrimidin-7-yl]-pyrrolidin-3-ol

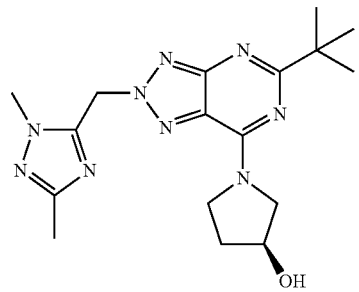 [SMILES: Cc1nc(Cn2nc3nc(C(C)(C)C)nc(N4CC[C@H](O)C4)c3n2)n(C)n1]

In analogy to the procedure described for the synthesis of (S)-1-[5-tert-Butyl-2-(4-methyl-furazan-3-ylmethyl)-2H-[1,2,3]triazolo[4,5-d]pyrimidin-7-yl]-pyrrolidin-3-ol (example 73), the title compound was prepared from Trifluoro-acetic acid (S)-1-(5-tert-butyl-3H-[1,2,3]triazolo[4,5-d]pyrimidin-7-yl)-pyrrolidin-3-yl-ester and 5-(chloromethyl)-1,3-dimethyl-1H-1,2,4-triazole and isolated as colorless gum. MS (m/e): 372.3 (MH$^+$).

Example 96

5-tert-Butyl-7-(3,3-difluoro-pyrrolidin-1-yl)-2-(2,5-dimethyl-2H-[1,2,4]triazol-3-ylmethyl)-2H-[1,2,3]triazolo[4,5-d]pyrimidine

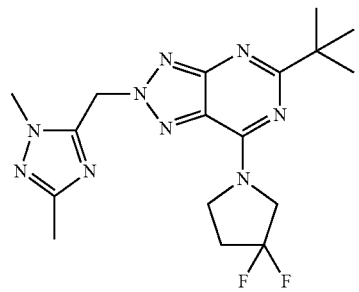 [SMILES: Cc1nc(Cn2nc3nc(C(C)(C)C)nc(N4CCC(F)(F)C4)c3n2)n(C)n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-butyl-7-(3,3-difluoropyrrolidin-1-yl)-3H-[1,2,3]triazolo[4,5-d]pyrimidine and 5-(chloromethyl)-1,3-dimethyl-1H-1,2,4-triazole and isolated as light yellow gum. MS (m/e): 392.3 (MH+).

Example 97

(2S,3S)-1-[5-tert-Butyl-2-(1-cyclopropyl-1H-tetrazol-5-ylmethyl)-2H-[1,2,3]triazolo[4,5-d]pyrimidin-7-yl]-2-hydroxymethyl-pyrrolidin-3-ol

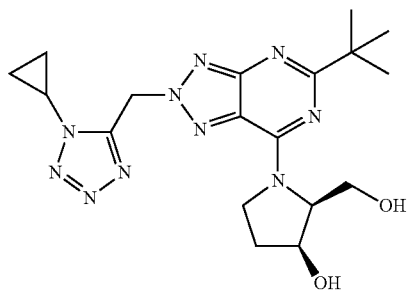 [SMILES: CC(C)(C)c1nc(N2CC[C@H](O)[C@@H]2CO)c2nn(Cc3nnnn3C3CC3)nc2n1]

a) (2S,3S)-1-[5-tert-Butyl-3-(4-methoxy-benzyl)-3H-[1,2,3]triazolo[4,5-d]pyrimidin-7-yl]-2-hydroxymethyl-pyrrolidin-3-ol

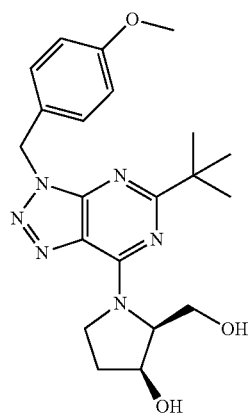 [SMILES: COc1ccc(Cn2nnc3c(N4CC[C@H](O)[C@@H]4CO)nc(C(C)(C)C)nc32)cc1]

In analogy to the procedure described for the synthesis of 4-(5-tert-Butyl-3-(4-methoxybenzyl)-3H-[1,2,3]triazolo[4,5-d]pyrimidin-7-yl)morpholine (example 1, step c) the title compound was prepared from 5-tert-Butyl-3-(4-methoxy-benzyl)-3H-[1,2,3]triazolo[4,5-d]pyrimidin-7(4H)-one after chlorination with POCl$_3$ and nucleophilic substitution with (2S,3S)-2-Hydroxymethyl-1-methyl-pyrrolidin-3-ol as light yellow gum. MS (m/e): 413.4 (MH+).

b) Trifluoro-acetic acid (2S,3S)-1-(5-tert-butyl-3H-[1,2,3]triazolo[4,5-d]pyrimidin-7-yl)-2-(2,2,2-trifluoro-acetoxymethyl)-pyrrolidin-3-yl ester

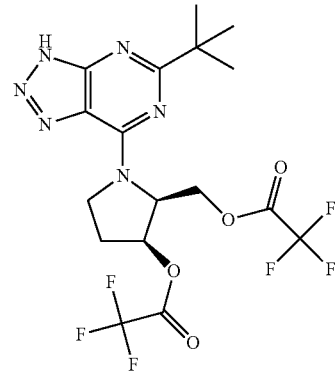 [SMILES: CC(C)(C)c1nc(N2CC[C@H](OC(=O)C(F)(F)F)[C@@H]2COC(=O)C(F)(F)F)c2nn[nH]c2n1]

A mixture of (2S,3S)-1-[5-tert-Butyl-3-(4-methoxy-benzyl)-3H-[1,2,3]triazolo[4,5-d]pyrimidin-7-yl]-2-hydroxymethyl-pyrrolidin-3-ol and triethylsilane in TFA was heated to 70° C. for 22 h and evaporated to dryness. The residue was used without further purification in the consecutive step.

c) (2S,3S)-1-[5-tert-Butyl-2-(1-cyclopropyl-1H-tetrazol-5-ylmethyl)-2H-[1,2,3]triazolo[4,5-d]pyrimidin-7-yl]-2-hydroxymethyl-pyrrolidin-3-ol In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from Trifluoro-acetic acid (2S,3S)-1-(5-tert-butyl-3H-[1,2,3]triazolo[4,5-d]pyrimidin-7-yl)-2-(2,2,2-trifluoro-acetoxymethyl)-pyrrolidin-3-yl ester and 5-(chloromethyl)-1-cyclopropyl-1H-tetrazole. After completion of the substitution reaction methanol was added and the mixture was stirred for 1 h at room temperature and subsequently subjected to purification with preparative HPLC on reversed phase eluting with a gradient formed from acetonitrile, water and NEt$_3$. After evaporation of the product containing fractions the title compound was isolated as light-yellow solid. MS (m/e): 415.4 (MH+).

Example 98

(2S,3S)-1-[5-tert-Butyl-2-(4-methyl-furazan-3-ylmethyl)-2H-[1,2,3]triazolo[4,5-d]pyrimidin-7-yl]-2-hydroxymethyl-pyrrolidin-3-ol

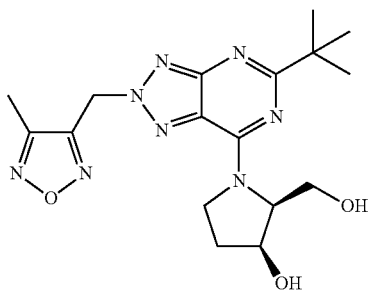 [SMILES: Cc1nonc1Cn1nc2nc(C(C)(C)C)nc(N3CC[C@H](O)[C@@H]3CO)c2n1]

In analogy to the procedure described for the synthesis of (2S,3S)-1-[5-tert-Butyl-2-(1-cyclopropyl-1H-tetrazol-5-yl-methyl)-2H-[1,2,3]triazolo[4,5-d]pyrimidin-7-yl]-2-hydroxymethyl-pyrrolidin-3-ol (example 97), the title compound was prepared from Trifluoro-acetic acid (2S,3S)-1-(5-tert-butyl-3H-[1,2,3]triazolo[4,5-d]pyrimidin-7-yl)-2-(2,2,2-trifluoro-acetoxymethyl)-pyrrolidin-3-yl ester and 3-(bromomethyl)-4-methyl-1,2,5-oxadiazole and isolated as white solid. MS (m/e): 389.3 (MH+).

Example 99

5-tert-Butyl-2-(4-methyl-furazan-3-ylmethyl)-7-(3,3,4,4-tetrafluoro-pyrrolidin-1-yl)-2H-[1,2,3]triazolo[4,5-d]pyrimidine

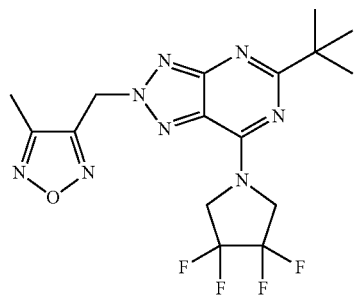 [SMILES: Cc1nonc1Cn1nc2nc(C(C)(C)C)nc(N3CC(F)(F)C(F)(F)C3)c2n1]

a) 5-tert-Butyl-3-(4-methoxy-benzyl)-7-(3,3,4,4-tetrafluoro-pyrrolidin-1-yl)-3H-[1,2,3]triazolo[4,5-d]pyrimidine

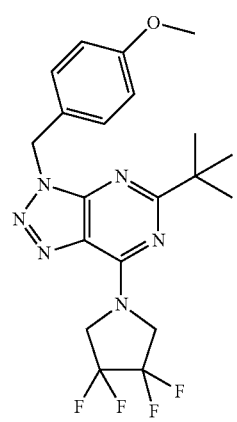 [SMILES: COc1ccc(Cn2nnc3c(N4CC(F)(F)C(F)(F)C4)nc(C(C)(C)C)nc32)cc1]

In analogy to the procedure described for the synthesis of 4-(5-tert-Butyl-3-(4-methoxybenzyl)-3H-[1,2,3]triazolo[4,5-d]pyrimidin-7-yl)morpholine (example 1, step c) the title compound was prepared from 5-tert-Butyl-3-(4-methoxy-benzyl)-3H-[1,2,3]triazolo[4,5-d]pyrimidin-7(4H)-one after chlorination with POCl₃ and nucleophilic substitution with 3,3,4,4-Tetrafluoro-pyrrolidine as purple oil and used in the consecutive step without further purification.

b) 5-tert-Butyl-7-(3,3,4,4-tetrafluoro-pyrrolidin-1-yl)-3H-[1,2,3]triazolo[4,5-d]pyrimidine

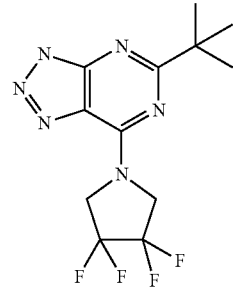 [SMILES: CC(C)(C)c1nc(N2CC(F)(F)C(F)(F)C2)c2nn[nH]c2n1]

A mixture of 5-tert-Butyl-3-(4-methoxy-benzyl)-7-(3,3,4,4-tetrafluoro-pyrrolidin-1-yl)-3H-[1,2,3]triazolo[4,5-d]pyrimidine and triethylsilane in TFA was heated to 70° C. for 22 h and evaporated to dryness. The residue was used without further purification in the consecutive step.

c) 5-tert-Butyl-2-(4-methyl-furazan-3-ylmethyl)-7-(3,3,4,4-tetrafluoro-pyrrolidin-1-yl)-2H-[1,2,3]triazolo[4,5-d]pyrimidine In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-Butyl-7-(3,3,4,4-tetrafluoro-pyrrolidin-1-yl)-3H-[1,2,3]triazolo[4,5-d]pyrimidine and 3-(bromomethyl)-4-methyl-1,2,5-oxadiazole and isolated as light yellow gum. MS (m/e): 415.3 (MH+).

Example 100

5-tert-Butyl-2-(3-methyl-[1,2,4]oxadiazol-5-ylmethyl)-7-(3,3,4,4-tetrafluoro-pyrrolidin-1-yl)-2H-[1,2,3]triazolo[4,5-d]pyrimidine

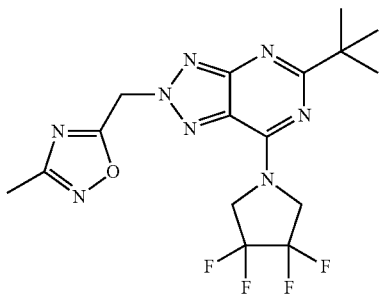 [SMILES: Cc1noc(Cn2nc3nc(C(C)(C)C)nc(N4CC(F)(F)C(F)(F)C4)c3n2)n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-Butyl-7-(3,3,4,4-tetrafluoro-pyrrolidin-1-yl)-3H-[1,2,3]triazolo[4,5-d]pyrimidine and 5-(chloromethyl)-3-methyl-1,2,4-oxadiazole and isolated as light yellow gum. MS (m/e): 415.3 (MH+).

Example 101

5-tert-Butyl-2-(5-methyl-[1,3,4]oxadiazol-2-ylmethyl)-7-(3,3,4,4-tetrafluoro-pyrrolidin-1-yl)-2H-[1,2,3]triazolo[4,5-d]pyrimidine

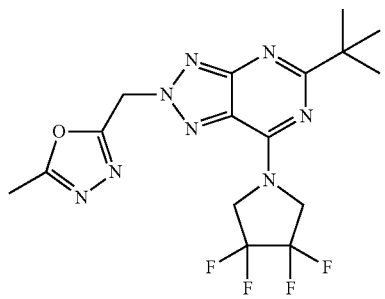 [SMILES: Cc1nnc(Cn2nc3nc(C(C)(C)C)nc(N4CC(F)(F)C(F)(F)C4)c3n2)o1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-Butyl-7-(3,3,4,4-tetrafluoro-pyrrolidin-1-yl)-3H-[1,2,3]triazolo[4,5-d]pyrimidine and 2-(chloromethyl)-5-methyl-1,3,4-oxadiazole and isolated as white solid. MS (m/e): 415.3 (MH$^+$).

Example 102

5-tert-Butyl-2-(1-methyl-1H-tetrazol-5-ylmethyl)-7-(3,3,4,4-tetrafluoro-pyrrolidin-1-yl)-2H-[1,2,3]triazolo[4,5-d]pyrimidine

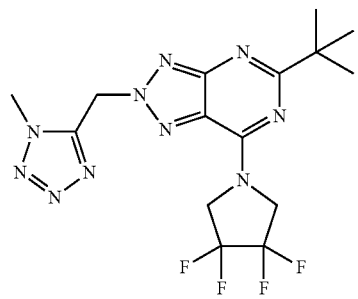 [SMILES: Cn1nnnc1Cn1nc2nc(C(C)(C)C)nc(N3CC(F)(F)C(F)(F)C3)c2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-Butyl-7-(3,3,4,4-tetrafluoro-pyrrolidin-1-yl)-3H-[1,2,3]triazolo[4,5-d]pyrimidine and 5-(chloromethyl)-1-methyl-1H-tetrazole and isolated as light yellow solid. MS (m/e): 415.3 (MH$^+$).

Example 103

5-tert-Butyl-2-(4,5-dimethyl-4H-[1,2,4]triazol-3-ylmethyl)-7-(3,3,4,4-tetrafluoro-pyrrolidin-1-yl)-2H-[1,2,3]triazolo[4,5-d]pyrimidine

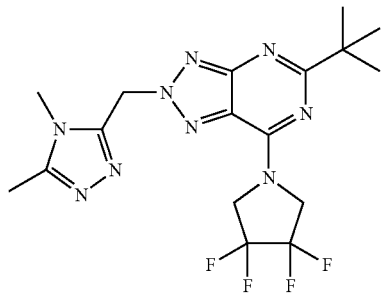 [SMILES: Cc1nnc(Cn2nc3nc(C(C)(C)C)nc(N4CC(F)(F)C(F)(F)C4)c3n2)n1C]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-Butyl-7-(3,3,4,4-tetrafluoro-pyrrolidin-1-yl)-3H-[1,2,3]triazolo[4,5-d]pyrimidine and 3-(chloromethyl)-4,5-dimethyl-4H-1,2,4-triazole hydrochloride and isolated as white solid. MS (m/e): 428.3 (MH$^+$).

Example 104

5-tert-Butyl-2-(3-methyl-3H-[1,2,3]triazol-4-ylmethyl)-7-(3,3,4,4-tetrafluoro-pyrrolidin-1-yl)-2H-[1,2,3]triazolo[4,5-d]pyrimidine

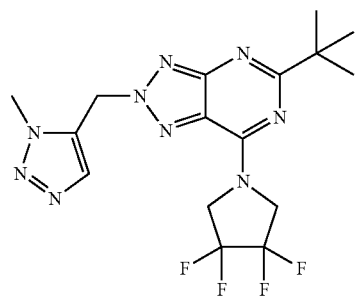 [SMILES: Cn1nncc1Cn1nc2nc(C(C)(C)C)nc(N3CC(F)(F)C(F)(F)C3)c2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-Butyl-7-(3,3,4,4-tetrafluoro-pyrrolidin-1-yl)-3H-[1,2,3]triazolo[4,5-d]pyrimidine and 5-(chloromethyl)-1-methyl-1H-1,2,3-triazole hydrochloride and isolated as yellow gum. MS (m/e): 414.3 (MH$^+$).

Example 105

5-tert-Butyl-2-(4,5-dimethyl-4H-[1,2,4]triazol-3-ylmethyl)-7-(2-oxa-6-aza-spiro[3.3]hept-6-yl)-2H-[1,2,3]triazolo[4,5-d]pyrimidine

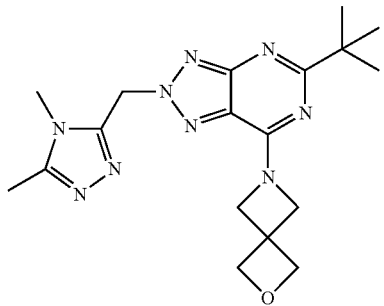 [SMILES: Cc1nnc(Cn2nc3nc(C(C)(C)C)nc(N4CC5(COC5)C4)c3n2)n1C]

a) 5-tert-Butyl-3-(4-methoxy-benzyl)-7-(2-oxa-6-aza-spiro[3.3]hept-6-yl)-3H-[1,2,3]triazolo[4,5-d]pyrimidine

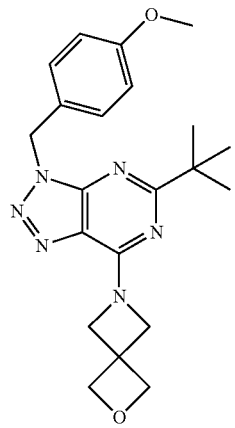 [SMILES: COc1ccc(Cn2nnc3c(N4CC5(COC5)C4)nc(C(C)(C)C)nc32)cc1]

In analogy to the procedure described for the synthesis of 4-(5-tert-Butyl-3-(4-methoxybenzyl)-3H-[1,2,3]triazolo[4,5-d]pyrimidin-7-yl)morpholine (example 1, step c) the title compound was prepared from 5-tert-Butyl-3-(4-methoxy-benzyl)-3H-[1,2,3]triazolo[4,5-d]pyrimidin-7(4H)-one after chlorination with POCl₃ and nucleophilic substitution with 2-oxa-6-aza-spiro[3.3]heptane and used in the consecutive step without further purification.

b) [1-(5-tert-Butyl-3H-[1,2,3]triazolo[4,5-d]pyrimidin-7-yl)-3-chloromethyl-azetidin-3-yl]-methanol

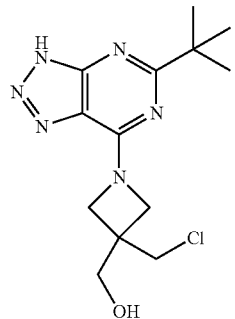 [SMILES: CC(C)(C)c1nc(N2CC(CO)(CCl)C2)c2nn[nH]c2n1]

A mixture of 645-tert-butyl-3-(4-methoxybenzyl)-3H-[1,2,3]triazolo[4,5-d]pyrimidin-7-yl)-2-oxa-6-azaspiro[3.3]heptane (361 mg, 915 μmol) and palladium (II) chloride (81.1 mg, 458 μmol) in MeOH (3.00 mL) was stirred at r.t. for 9 h under H₂ (1 atm, balloon) atmosphere. After replacement of H₂ with N₂, the reaction mixture was filtered with cotton, concentrated in vacuo and used in the consecutive step without further purification.

c) 5-tert-Butyl-7-(2-oxa-6-aza-spiro[3.3]hept-6-yl)-3H-[1,2,3]triazolo[4,5-d]pyrimidine

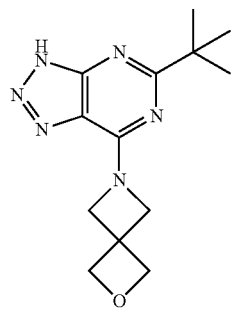 [SMILES: CC(C)(C)c1nc(N2CC3(COC3)C2)c2nn[nH]c2n1]

A mixture of (1-(5-tert-butyl-3H-[1,2,3]triazolo[4,5-d]pyrimidin-7-yl)-3-(chloromethypazetidin-3-yl)methanol (284 mg, 915 μmol) and potassium tert-butoxide (205 mg, 1.83 mmol) in THF (3.00 mL) at 0° C. was stirred to room temperature and stirred at room temperature for 20 h. The reaction mixture was filtered and concentrated in vacuo and used without further purification.

d) 5-tert-Butyl-2-(4,5-dimethyl-4H-[1,2,4]triazol-3-ylmethyl)-7-(2-oxa-6-aza-spiro[3.3]hept-6-yl)-2H-[1,2,3]triazolo[4,5-d]pyrimidine In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-Butyl-7-(2-oxa-6-aza-spiro[3.3]hept-6-yl)-3H-[1,2,3]triazolo[4,5-d]pyrimidine and 5-(chloromethyl)-1-cyclopropyl-1H-tetrazole and isolated as white solid. MS (m/e): 397.3 (MH⁺).

Example 106

5-tert-Butyl-2-(4,5-dimethyl-4H-[1,2,4]triazol-3-ylmethyl)-7-(2-oxa-6-aza-spiro[3.3]hept-6-yl)-2H-[1,2,3]triazolo[4,5-d]pyrimidine

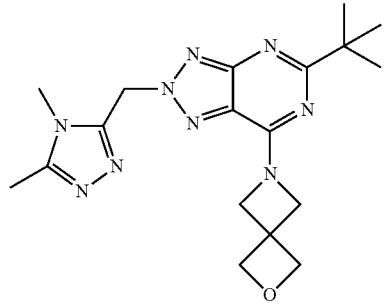 [SMILES: Cc1nnc(Cn2nc3nc(C(C)(C)C)nc(N4CC5(COC5)C4)c3n2)n1C]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-Butyl-7-(2-oxa-6-aza-spiro[3.3]hept-6-yl)-3H-[1,2,3]triazolo[4,5-d]pyrimidine and 3-(chloromethyl)-4,5-dimethyl-4H-1,2,4-triazole hydrochloride and isolated as white solid. MS (m/e): 384.3 (MH⁺).

Example 107

5-tert-Butyl-2-(2-methanesulfonyl-benzyl)-7-(2-oxa-6-aza-spiro[3.3]hept-6-yl)-2H-[1,2,3]triazolo[4,5-d]pyrimidine

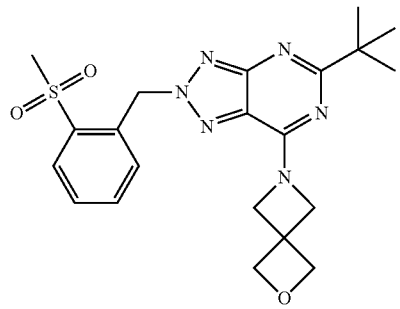 [SMILES: CC(C)(C)c1nc(N2CC3(COC3)C2)c2nn(Cc3ccccc3S(C)(=O)=O)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-Butyl-7-(2-oxa-6-aza-spiro[3.3]hept-6-yl)-3H-[1,2,3]triazolo[4,5-d]pyrimidine and 1-(bromomethyl)-2-(methylsulfonyl)benzene and isolated as white solid. MS (m/e): 443.3 (MH+).

Example 108

5-tert-Butyl-2-(3-chloro-pyridin-2-ylmethyl)-7-(2-oxa-6-aza-spiro[3.3]hept-6-yl)-2H-[1,2,3]triazolo[4,5-d]pyrimidine

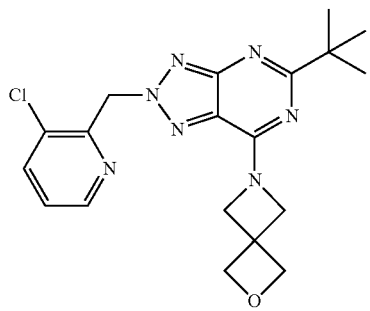 [SMILES: CC(C)(C)c1nc(N2CC3(COC3)C2)c2nn(Cc3ncccc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 5-tert-Butyl-7-(2-oxa-6-aza-spiro[3.3]hept-6-yl)-3H-[1,2,3]triazolo[4,5-d]pyrimidine and 3-chloro-2-(chloromethyl)pyridine and isolated as light brown gum. MS (m/e): 400.3 (MH+).

Example 109

(S)-1-[2-(2-Chloro-benzyl)-5-(2,2,2-trifluoro-ethoxy)-2H-[1,2,3]triazolo[4,5-d]pyrimidin-7-yl]-pyrrolidin-3-ol

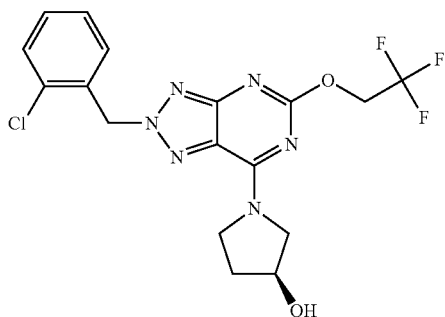 [SMILES: O[C@H]1CCN(c2nc(OCC(F)(F)F)nc3nn(Cc4ccccc4Cl)nc23)C1]

a) 3-(4-Methoxy-benzyl)-3H-[1,2,3]triazolo[4,5-d]pyrimidine-5,7-diol

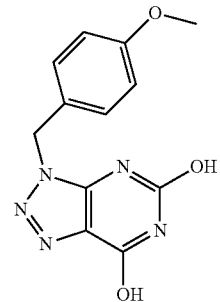 [SMILES: COc1ccc(Cn2nnc3c(O)nc(O)nc32)cc1]

A mixture of 5-Amino-1-(4-methoxybenzyl)-1H-1,2,3-triazole-4-carboxamide (example 1, step a) (7.59 g, 30.7 mmol), diethyl carbonate (4.72 g, 39.9 mmol) and sodium ethoxide (3.76 g, 55.3 mmol) in ethanol (97.1 mL) was heated to reflux overnight. The solid was filtered, washed with EtOH and dried to give 3-(4-methoxybenzyl)-3H-[1,2,3]triazolo[4,5-d]pyrimidine-5,7(4H,6H)-dione (8.542 g, 15.6 mmol, 50.9% yield) which was used in the consecutive step without further purification. MS (m/e): 272.0 (MH+).

b) 5,7-Dichloro-3-(4-methoxy-benzyl)-3H-[1,2,3]triazolo[4,5-d]pyrimidine

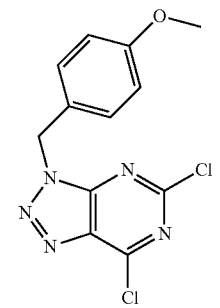 [SMILES: COc1ccc(Cn2nnc3c(Cl)nc(Cl)nc32)cc1]

A mixture of 3-(4-Methoxy-benzyl)-3H-[1,2,3]triazolo[4,5-d]pyrimidine-5,7-diol (example 109, a) and N,N-diethyl aniline (2.73 mL) at 0° C. was treated with POCl3 (44.4 mL) and heated to 120° C. for 4 h. The excess POCl3 was removed by distillation and the residue was poured into 100 mL water/ice and extracted with DCM. The combined organic layers were dried with MgSO4, filtered and evaporated. The title compound was used in the consecutive step without further purification.

c) (S)-1-[5-Chloro-3-(4-methoxy-benzyl)-3H-[1,2,3]triazolo[4,5-d]pyrimidin-7-yl]-pyrrolidin-3-ol

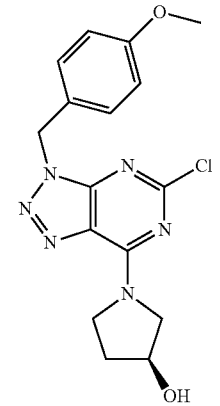 [SMILES: COc1ccc(Cn2nnc3c(N4CC[C@H](O)C4)nc(Cl)nc32)cc1]

A mixture of 5,7-Dichloro-3-(4-methoxy-benzyl)-3H-[1,2,3]triazolo[4,5-d]pyrimidine (example 109, b) (2.95 g), (S)-pyrrolidinol (1.82 g, 20.9 mmol) and DIPEA (9.83 g, 76.1 mmol) in DCM was stirred at room temperature for 30 min. The mixture was poured into water, extracted with DCM and the combined organic layers were dried with MgSO$_4$, filtered and evaporated to yield the crude title compound which was used in the consecutive step without further purification. MS (m/e): 361.3 (MH$^+$).

d) (S)-1-[3-(4-Methoxy-benzyl)-5-(2,2,2-trifluoro-ethoxy)-3H-[1,2,3]triazolo[4,5-d]pyrimidin-7-yl]-pyrrolidin-3-ol

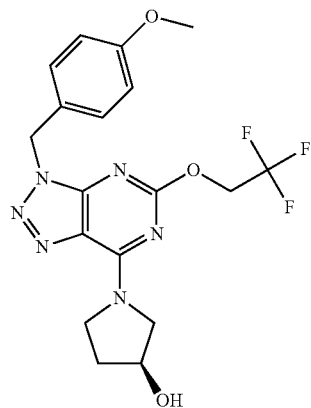 [SMILES: COc1ccc(Cn2nnc3c(N4CC[C@H](O)C4)nc(OCC(F)(F)F)nc32)cc1]

A mixture of 2,2,2-trifluoroethanol (936 mg, 9.35 mmol) in THF was treated with NaH for 1 h at room temperature. (S)-1-[5-Chloro-3-(4-methoxy-benzyl)-3H-[1,2,3]triazolo[4,5-d]pyrimidin-7-yl]-pyrrolidin-3-ol (example 109, c) was added and the mixture was stirred at 100° C. for 2 h. The reaction mixture was poured into 1 M HCl and extracted with EtOAc. The combined organic layers were dried over MgSO$_4$ and concentrated in vacuo to yield the crude title compound which was used in the consecutive step without further purification. MS (m/e): 425.4 (MH$^+$).

e) (S)-1-[5-(2,2,2-Trifluoro-ethoxy)-3H-[1,2,3]triazolo[4,5-d]pyrimidin-7-yl]-pyrrolidin-3-ol

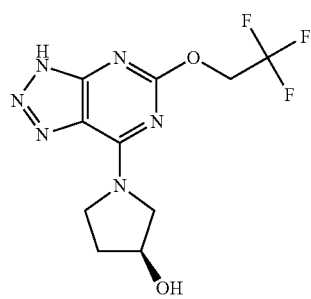 [SMILES: O[C@H]1CCN(c2nc(OCC(F)(F)F)nc3[nH]nnc23)C1]

(S)-1-[3-(4-Methoxy-benzyl)-5-(2,2,2-trifluoro-ethoxy)-3H-[1,2,3]triazolo[4,5-d]pyrimidin-7-yl]-pyrrolidin-3-ol (example 109, d) in 4.57 mL TFA was heated to 80° C. over night and evaporated. The residue was treated with 1M NaOH and washed with EtOAc. The combined organic layer was evaporated to yield the crude title compound which was used in the consecutive step without further purification. MS (m/e): 305.2 (MH$^+$).

f) (S)-1-[2-(2-Chloro-benzyl)-5-(2,2,2-trifluoro-ethoxy)-2H-[1,2,3]triazolo[4,5-d]pyrimidin-7-yl]-pyrrolidin-3-ol In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from (S)-1-[5-(2,2,2-Trifluoro-ethoxy)-3H-[1,2,3]triazolo[4,5-d]pyrimidin-7-yl]-pyrrolidin-3-ol and 1-(bromomethyl)-2-chlorobenzene. MS (m/e): 429.4 (MH$^+$).

Example 110

(S)-1-[5-(2,2,2-Trifluoro-ethoxy)-2-(2-trifluoromethyl-benzyl)-2H-[1,2,3]triazolo[4,5-d]pyrimidin-7-yl]-pyrrolidin-3-ol

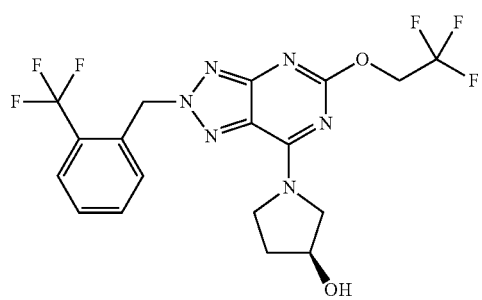 [SMILES: O[C@H]1CCN(c2nc(OCC(F)(F)F)nc3nn(Cc4ccccc4C(F)(F)F)nc23)C1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from (S)-1-[5-(2,2,2-Trifluoro-ethoxy)-3H-[1,2,3]triazolo[4,5-d]pyrimidin-7-yl]-pyrrolidin-3-ol and 1-(bromomethyl)-2-(trifluoromethyl)benzene. MS (m/e): 463.4 (MH$^+$).

Example 111

(S)-1-[2-(2-Chloro-benzyl)-5-isopropoxy-2H-[1,2,3]triazolo[4,5-d]pyrimidin-7-yl]-pyrrolidin-3-ol

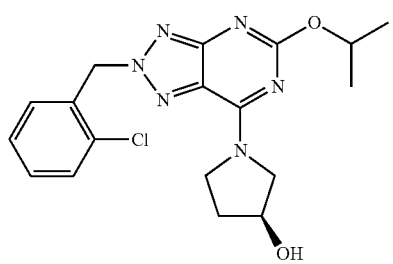 [SMILES: CC(C)Oc1nc(N2CC[C@H](O)C2)c2nn(Cc3ccccc3Cl)nc2n1]

a) Trifluoro-acetic acid (S)-1-(5-isopropoxy-3H-[1,2,3]triazolo[4,5-d]pyrimidin-7-yl)-pyrrolidin-3-yl ester

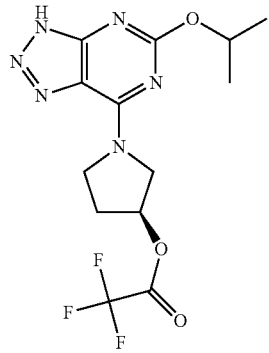 [SMILES: CC(C)Oc1nc(N2CC[C@H](OC(=O)C(F)(F)F)C2)c2nn[nH]c2n1]

In analogy to the procedure described for the synthesis of (S)-1-[5-(2,2,2-Trifluoro-ethoxy)-3H-[1,2,3]triazolo[4,5-d]pyrimidin-7-yl]-pyrrolidin-3-ol (example 108, e) the title compound was prepared from (S)-1-[5-Chloro-3-(4-methoxy-benzyl)-3H-[1,2,3]triazolo[4,5-d]pyrimidin-7-yl]-pyrrolidin-3-ol (example 108, c) through nucleophilic substitution with iso-propanol and subsequent cleavage of the 4-methoxy benzyl group with TFA and used crude in the subsequent step.

b) (S)-1-[2-(2-Chloro-benzyl)-5-isopropoxy-2H-[1,2,3]triazolo[4,5-d]pyrimidin-7-yl]-pyrrolidin-3-ol In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from Trifluoro-acetic acid (S)-1-(5-isopropoxy-3H-[1,2,3]triazolo[4,5-d]pyrimidin-7-yl)-pyrrolidin-3-yl ester and 1-(bromomethyl)-2-chlorobenzene. MS (m/e): 389.3 (MH$^+$)

Example 112

7-(3,3-Difluoro-pyrrolidin-1-yl)-5-(2,2-dimethyl-propoxy)-2-(1-methyl-1H-tetrazol-5-ylmethyl)-2H-[1,2,3]triazolo[4,5-d]pyrimidine

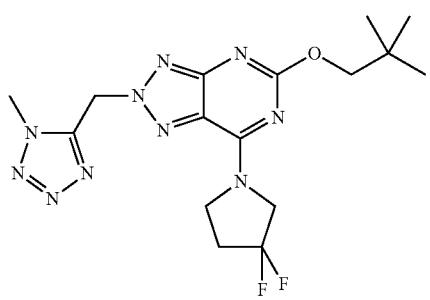 [SMILES: Cn1nnnc1Cn1nc2nc(OCC(C)(C)C)nc(N3CCC(F)(F)C3)c2n1]

a) 5-Chloro-7-(3,3-difluoro-pyrrolidin-1-yl)-3-(4-methoxy-benzyl)-3H-[1,2,3]triazolo[4,5-d]pyrimidine

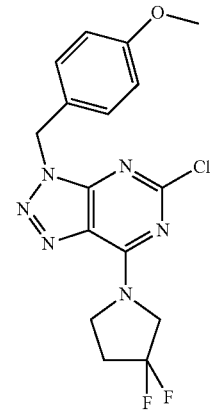 [SMILES: COc1ccc(Cn2nnc3c(N4CCC(F)(F)C4)nc(Cl)nc32)cc1]

In analogy to the procedure described for the synthesis of (S)-1-[5-Chloro-3-(4-methoxy-benzyl)-3H-[1,2,3]triazolo[4,5-d]pyrimidin-7-yl]-pyrrolidin-3-ol (example 108, c) the title compound was prepared from 5,7-Dichloro-3-(4-methoxy-benzyl)-3H-[1,2,3]triazolo[4,5-d]pyrimidine and 3,3-difluoro-pyrrolidine and used in the consecutive step without further purification.

b) 7-(3,3-Difluoro-pyrrolidin-1-yl)-5-(2,2-dimethyl-propoxy)-3H-[1,2,3]triazolo[4,5-d]pyrimidine

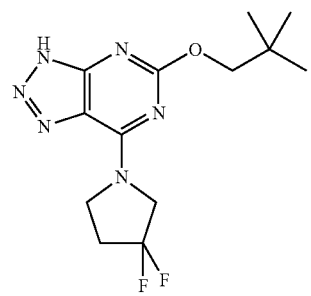 [SMILES: CC(C)(C)COc1nc(N2CCC(F)(F)C2)c2nn[nH]c2n1]

In analogy to the procedure described for the synthesis of (S)-1-[5-(2,2,2-Trifluoro-ethoxy)-3H-[1,2,3]triazolo[4,5-d]pyrimidin-7-yl]-pyrrolidin-3-ol (example 108, e) the title compound was prepared from 5-Chloro-7-(3,3-difluoro-pyrrolidin-1-yl)-3-(4-methoxy-benzyl)-3H-[1,2,3]triazolo[4,5-d]pyrimidine (example 112, a) through nucleophilic substitution with 2,2-dimethylpropan-1-ol and subsequent cleavage of the 4-methoxy benzyl group with TFA and used crude in the subsequent step.

c) 7-(3,3-Difluoro-pyrrolidin-1-yl)-5-(2,2-dimethyl-propoxy)-2-(1-methyl-1H-tetrazol-5-ylmethyl)-2H-[1,2,3]triazolo[4,5-d]pyrimidine In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 7-(3,3-Difluoro-pyrrolidin-1- yl)-5-(2,2-dimethyl-propoxy)-3H-[1,2,3]triazolo[4,5-d]pyrimidine and 5-(chloromethyl)-1-methyl-1H-tetrazole. MS (m/e): 409.4 (MH⁺).

Example 113

(R)-1-[5-tert-Butyl-2-(1-methyl-1H-tetrazol-5-ylmethyl)-2H-[1,2,3]triazolo[4,5-d]pyrimidin-7-yl]-pyrrolidin-3-ol

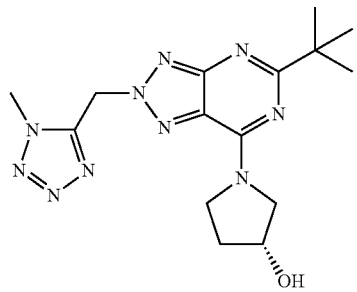 [SMILES: Cn1nnnc1Cn1nc2nc(C(C)(C)C)nc(N3CC[C@@H](O)C3)c2n1]

a) (R)-1-(3-Benzyl-5-tert-butyl-3H-[1,2,3]triazolo[4,5-d]pyrimidin-7-yl)-pyrrolidin-3-ol

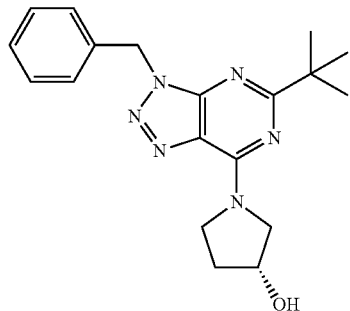 [SMILES: CC(C)(C)c1nc(N2CC[C@@H](O)C2)c2nnn(Cc3ccccc3)c2n1]

In analogy to the procedure described for the synthesis of 4-(5-tert-Butyl-3-(4-methoxybenzyl)-3H-[1,2,3]triazolo[4,5-d]pyrimidin-7-yl)morpholine/example 1c) the title compound was prepared from 3-benzyl-5-tert-butyl-7-chloro-triazolo[4,5-d]pyrimidine and (R)-pyrrolidin-3-ol and isolated as white foam. MS (m/e): 352.4 (MH⁺).

b) (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (R)-1-(3-Benzyl-5-tert-butyl-3H-[1,2,3]triazolo[4,5-d]pyrimidin-7-yl)-pyrrolidin-3-ol was hydrogenated over Pd/C and the resulting (R)-1-(5-tert-Butyl-3H-[1,2,3]triazolo[4,5-d]pyrimidin-7-yl)-pyrrolidin-3-ol was reacted in analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b) with 5-(chloromethyl)-1-methyl-1H-tetrazole. MS (m/e): 359.3 (MH⁺)

Example 114

1-[5-tert-Butyl-2-(1-methyl-1H-tetrazol-5-ylmethyl)-2H-[1,2,3]triazolo[4,5-d]pyrimidin-7-yl]-pyrrolidin-3-ol

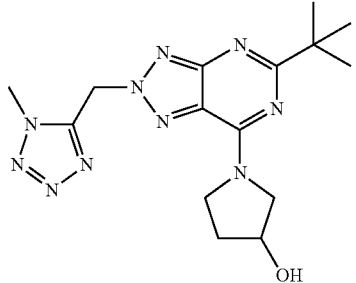 [SMILES: Cn1nnnc1Cn1nc2nc(C(C)(C)C)nc(N3CCC(O)C3)c2n1]

a) 1-(3-Benzyl-5-tert-butyl-3H-[1,2,3]triazolo[4,5-d]pyrimidin-7-yl)-pyrrolidin-3-ol In analogy to the procedure described for the synthesis of (R)-1-(3-Benzyl-5-tert-butyl-3H-[1,2,3]triazolo[4,5-d]pyrimidin-7-yl)-pyrrolidin-3-ol (example 113, a) the title compound was prepared from 3-benzyl-5-tert-butyl-7-chloro-triazolo[4,5-d]pyrimidine and pyrrolidin-3-ol and isolated as light yellow oil.

b) 1-[5-tert-Butyl-2-(1-methyl-1H-tetrazol-5-ylmethyl)-2H-[1,2,3]triazolo[4,5-d]pyrimidin-7-yl]-pyrrolidin-3-ol In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) 1-(3-Benzyl-5-tert-butyl-3H-[1,2,3]triazolo[4,5-d]pyrimidin-7-yl)-pyrrolidin-3-ol was hydrogenated and subsequently reacted with 5-(chloromethyl)-1-methyl-1H-tetrazole and isolated as light yellow oil. MS (m/e): 359.3 (MH⁺).

Example 115

7-(3,3-Difluoro-pyrrolidin-1-yl)-2-(2-trifluoromethyl-benzyl)-5-((S)-2,2,2-trifluoro-1-methyl-ethoxy)-2H-[1,2,3]triazolo[4,5-d]pyrimidine

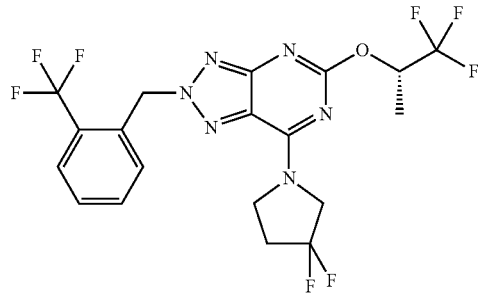 [SMILES: C[C@H](Oc1nc(N2CCC(F)(F)C2)c2nn(Cc3ccccc3C(F)(F)F)nc2n1)C(F)(F)F]

a) 7-(3,3-Difluoro-pyrrolidin-1-yl)-5-((S)-2,2,2-trifluoro-1-methyl-ethoxy)-3H-[1,2,3]triazolo[4,5-d]pyrimidine

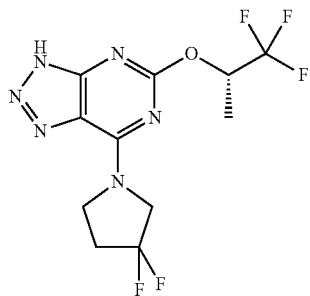 [SMILES: C[C@H](Oc1nc(N2CCC(F)(F)C2)c2nn[nH]c2n1)C(F)(F)F]

In analogy to the procedure described for the synthesis of 7-(3,3-Difluoro-pyrrolidin-1-yl)-5-(2,2-dimethyl-propoxy)-3H-[1,2,3]triazolo[4,5-d]pyrimidine (example 112, b) the title compound was prepared from 5-Chloro-7-(3,3-difluoro-pyrrolidin-1-yl)-3-(4-methoxy-benzyl)-3H-[1,2,3]triazolo[4,5-d]pyrimidine (example 112, a) through nucleophilic substitution with (S)-1,1,1-Trifluoro-propan-2-ol and subsequent cleavage of the 4-methoxy benzyl group with TFA and used crude in the subsequent step.

b) 7-(3,3-Difluoro-pyrrolidin-1-yl)-2-(2-trifluoromethyl-benzyl)-5-((S)-2,2,2-trifluoro-1-methyl-ethoxy)-2H-[1,2,3]triazolo[4,5-d]pyrimidine In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 7-(3,3-Difluoro-pyrrolidin-1-yl)-5-(2,2-dimethyl-propoxy)-3H-[1,2,3]triazolo[4,5-d]pyrimidine and 1-(bromomethyl)-2-(trifluoromethyl)benzene. MS (m/e): 497.4 (MH$^+$).

Example 116

7-(3,3-Difluoro-pyrrolidin-1-yl)-2-(2-methanesulfonyl-benzyl)-5-((S)-2,2,2-trifluoro-1-methyl-ethoxy)-2H-[1,2,3]triazolo[4,5-d]pyrimidine

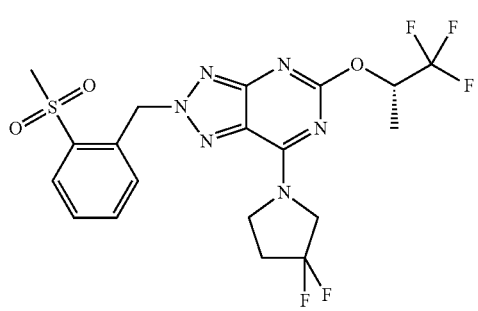 [SMILES: C[C@H](Oc1nc(N2CCC(F)(F)C2)c2nn(Cc3ccccc3S(C)(=O)=O)nc2n1)C(F)(F)F]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 7-(3,3-Difluoro-pyrrolidin-1-yl)-5-(2,2-dimethyl-propoxy)-3H-[1,2,3]triazolo[4,5-d]pyrimidine and 1-(bromomethyl)-2-(methylsulfonyl)benzene. MS (m/e): 507.4 (MH$^+$).

Example 117

2-(3-Chloro-pyridin-2-ylmethyl)-7-(3,3-difluoro-pyrrolidin-1-yl)-5-((S)-2,2,2-trifluoro-1-methyl-ethoxy)-2H-[1,2,3]triazolo[4,5-d]pyrimidine

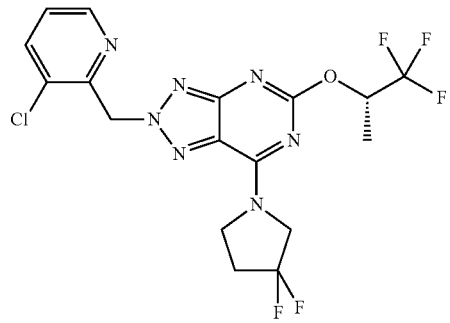 [SMILES: C[C@H](Oc1nc(N2CCC(F)(F)C2)c2nn(Cc3ncccc3Cl)nc2n1)C(F)(F)F]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 7-(3,3-Difluoro-pyrrolidin-1-yl)-5-(2,2-dimethyl-propoxy)-3H-[1,2,3]triazolo[4,5-d]pyrimidine and 3-chloro-2-(chloromethyl)pyridine. MS (m/e): 464.4 (MH$^+$).

Example 118

7-(3,3-Difluoro-pyrrolidin-1-yl)-2-(5-methyl-[1,3,4]oxadiazol-2-ylmethyl)-5-((S)-2,2,2-trifluoro-1-methyl-ethoxy)-2H-[1,2,3]triazolo[4,5-d]pyrimidine

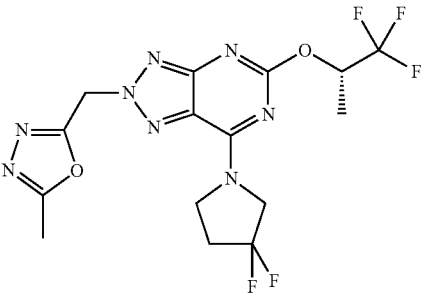 [SMILES: Cc1nnc(Cn2nc3nc(O[C@@H](C)C(F)(F)F)nc(N4CCC(F)(F)C4)c3n2)o1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 7-(3,3-Difluoro-pyrrolidin-1-yl)-5-(2,2-dimethyl-propoxy)-3H-[1,2,3]triazolo[4,5-d]pyrimidine and 2-(chloromethyl)-5-methyl-1,3,4-oxadiazole. MS (m/e): 435.4 (MH$^+$).

Example 119

7-(3,3-Difluoro-pyrrolidin-1-yl)-2-(3-methyl-[1,2,4]oxadiazol-5-ylmethyl)-5-((S)-2,2,2-trifluoro-1-methyl-ethoxy)-2H-[1,2,3]triazolo[4,5-d]pyrimidine

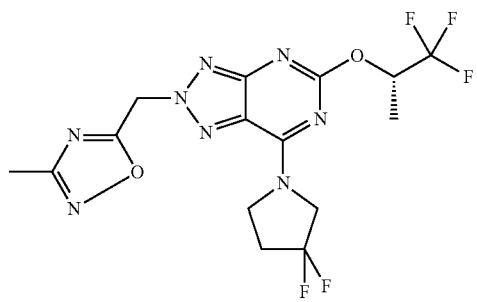 [SMILES: Cc1noc(Cn2nc3nc(O[C@@H](C)C(F)(F)F)nc(N4CCC(F)(F)C4)c3n2)n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 7-(3,3-Difluoro-pyrrolidin-1-yl)-5-(2,2-dimethyl-propoxy)-3H-[1,2,3]triazolo[4,5-d]pyrimidine and 5-(chloromethyl)-3-methyl-1,2,4-oxadiazole. MS (m/e): 435.4 (MH+).

Example 120

7-(3,3-Difluoro-pyrrolidin-1-yl)-2-(1-methyl-1H-tetrazol-5-ylmethyl)-5-((S)-2,2,2-trifluoro-1-methyl-ethoxy)-2H-[1,2,3]triazolo[4,5-d]pyrimidine

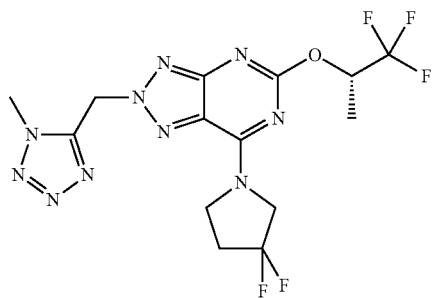 [SMILES: C[C@H](Oc1nc(N2CCC(F)(F)C2)c2nn(Cc3nnnn3C)nc2n1)C(F)(F)F]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 7-(3,3-Difluoro-pyrrolidin-1-yl)-5-(2,2-dimethyl-propoxy)-3H-[1,2,3]triazolo[4,5-d]pyrimidine and 5-(chloromethyl)-1-methyl-1H-tetrazole. MS (m/e): 435.3 (MH+)

Example 121

7-(3,3-Difluoro-pyrrolidin-1-yl)-2-(4-methyl-furazan-3-ylmethyl)-5-((S)-2,2,2-trifluoro-1-methyl-ethoxy)-2H-[1,2,3]triazolo[4,5-d]pyrimidine

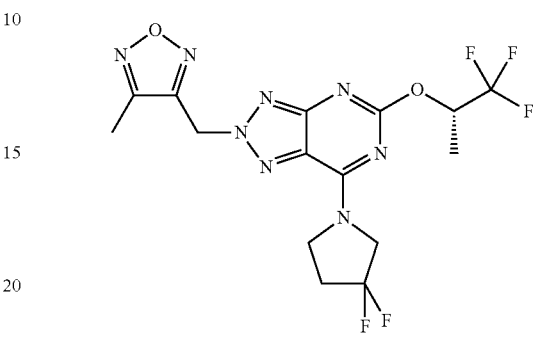

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 7-(3,3-Difluoro-pyrrolidin-1-yl)-5-(2,2-dimethyl-propoxy)-3H-[1,2,3]triazolo[4,5-d]pyrimidine and 3-(bromomethyl)-4-methyl-1,2,5-oxadiazole. MS (m/e): 435.3 (MH+).

Example 122

7-(3,3-Difluoro-pyrrolidin-1-yl)-5-((S)-2,2,2-trifluoro-1-methyl-ethoxy)-2-(3,3,3-trifluoro-propyl)-2H-[1,2,3]triazolo[4,5-d]pyrimidine

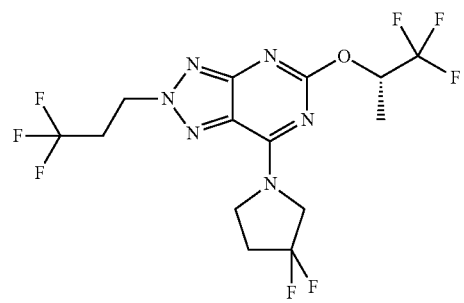 [SMILES: C[C@H](Oc1nc(N2CCC(F)(F)C2)c2nn(CCC(F)(F)F)nc2n1)C(F)(F)F]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 7-(3,3-Difluoro-pyrrolidin-1-yl)-5-(2,2-dimethyl-propoxy)-3H-[1,2,3]triazolo[4,5-d]pyrimidine and 3-bromo-1,1,1-trifluoropropane. MS (m/e): 435.3 (MH+).

Example 123

2-(1-Cyclopropyl-1H-tetrazol-5-ylmethyl)-7-(3,3-difluoro-pyrrolidin-1-yl)-5-((S)-2,2,2-trifluoro-1-methyl-ethoxy)-2H-[1,2,3]triazolo[4,5-d]pyrimidine

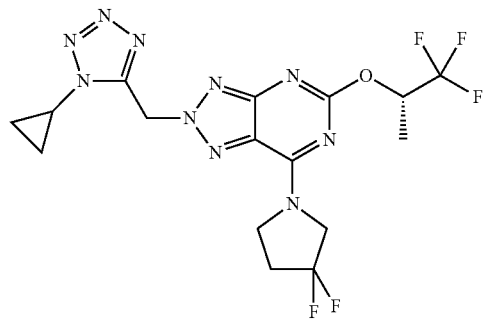 [SMILES: C[C@H](Oc1nc(N2CCC(F)(F)C2)c2nn(Cc3nnnn3C3CC3)nc2n1)C(F)(F)F]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from 7-(3,3-Difluoro-pyrrolidin-1-yl)-5-(2,2-dimethyl-propoxy)-3H-[1,2,3]triazolo[4,5-d]pyrimidine and 5-(chloromethyl)-1-cyclopropyl-1H-tetrazole. MS (m/e): 461.4 (MH+).

Example 124-a and Example 124-b (S)-1-[5-tert-Butyl-2-(2-chloro-benzyl)-2H-[1,2,3]triazolo[4,5-d]pyrimidin-7-yl]-3-methyl-pyrrolidin-3-ol and (R)-1-[5-tert-Butyl-2-(2-chloro-benzyl)-2H-[1,2,3]triazolo[4,5-d]pyrimidin-7-yl]-3-methyl-pyrrolidin-3-ol

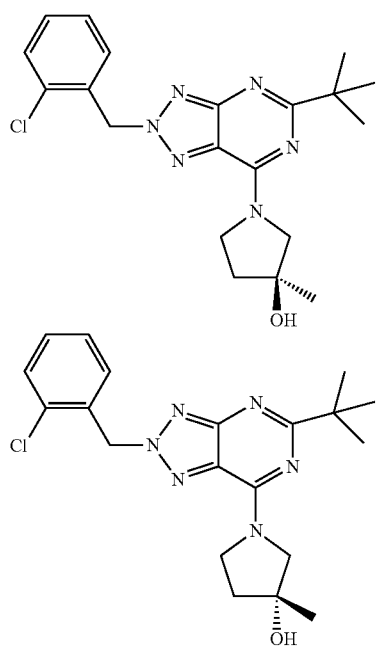

a) 1-(3-Benzyl-5-tert-butyl-3H-[1,2,3]triazolo[4,5-d]pyrimidin-7-yl)-3-methyl-pyrrolidin-3-ol

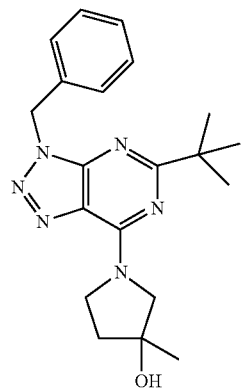 [SMILES: CC1(O)CCN(c2nc(C(C)(C)C)nc3c2nnn3Cc2ccccc2)C1]

In analogy to the procedure described for the synthesis of (R)-1-(3-Benzyl-5-tert-butyl-3H-[1,2,3]triazolo[4,5-d]pyrimidin-7-yl)-pyrrolidin-3-ol (example 113, a) the title compound was prepared from 3-benzyl-5-tert-butyl-7-chloro-triazolo[4,5-d]pyrimidine and 3-Methyl-pyrrolidin-3-ol and subjected to separation by chiral HPLC to yield (S)-1-(3-benzyl-5-tert-butyl-3H-[1,2,3]triazolo[4,5-d]pyrimidin-7-yl)-3-methylpyrrolidin-3-ol and (R)-1-(3-benzyl-5-tert-butyl-3H-[1,2,3]triazolo[4,5-d]pyrimidin-7-yl)-3-methylpyrrolidin-3-ol. The enantiopure intermediates where isolated with 39% and 36% yield.

b) (S)-1-[5-tert-Butyl-2-(2-chloro-benzyl)-2H-[1,2,3]triazolo[4,5-d]pyrimidin-7-yl]-3-methyl-pyrrolidin-3-ol and (R)-1-[5-tert-Butyl-2-(2-chloro-benzyl)-2H-[1,2,3]triazolo[4,5-d]pyrimidin-7-yl]-3-methyl-pyrrolidin-3-ol In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (S)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 1-(bromomethyl)-2-chlorobenzene. MS (m/e): 401.4 (MH+).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (R)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 1-(bromomethyl)-2-chlorobenzene. MS (m/e): 401.4 (MH+).

Example 125-a and Example 125-b (S)-1-[5-tert-Butyl-2-(2-trifluoromethyl-benzyl)-2H-[1,2,3]triazolo[4,5-d]pyrimidin-7-yl]-3-methyl-pyrrolidin-3-ol and (R)-1-[5-tert-Butyl-2-(2-trifluoromethyl-benzyl)-2H-[1,2,3]triazolo[4,5-d]pyrimidin-7-yl]-3-methyl-pyrrolidin-3-ol

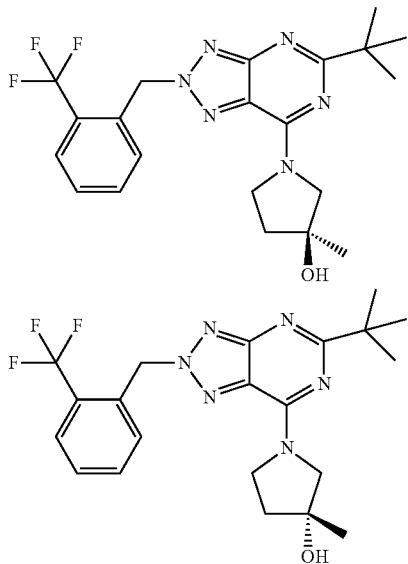

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (S)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 1-(bromomethyl)-2-(trifluoromethyl)benzene. MS (m/e): 435.4 (MH$^+$).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (R)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 1-(bromomethyl)-2-(trifluoromethyl)benzene. MS (m/e): 435.4 (MH$^+$).

Example 126-a and Example 126-b (S)-1-[5-tert-Butyl-2-(2-methanesulfonyl-benzyl)-2H-[1,2,3]triazolo[4,5-d]pyrimidin-7-yl]-3-methyl-pyrrolidin-3-ol and (R)-1-[5-tert-Butyl-2-(2-methanesulfonyl-benzyl)-2H-[1,2,3]triazolo[4,5-d]pyrimidin-7-yl]-3-methyl-pyrrolidin-3-ol

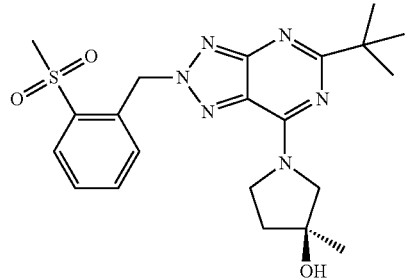

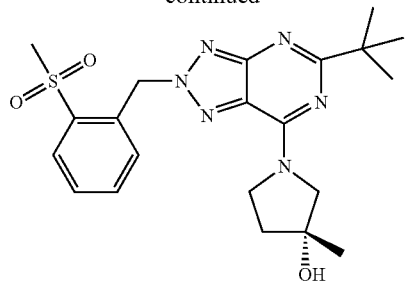

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (S)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 1-(bromomethyl)-2-(methylsulfonyl)benzene. MS (m/e): 445.4 (MH$^+$).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (R)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 1-(bromomethyl)-2-(methylsulfonyl)benzene. MS (m/e): 445.4 (MH$^+$).

Example 127-a and Example 127-b (S)-1-[5-tert-Butyl-2-(3-chloro-pyridin-2-ylmethyl)-2H-[1,2,3]triazolo[4,5-d]pyrimidin-7-yl]-3-methyl-pyrrolidin-3-ol and (R)-1-[5-tert-Butyl-2-(3-chloro-pyridin-2-ylmethyl)-2H-[1,2,3]triazolo[4,5-d]pyrimidin-7-yl]-3-methyl-pyrrolidin-3-ol

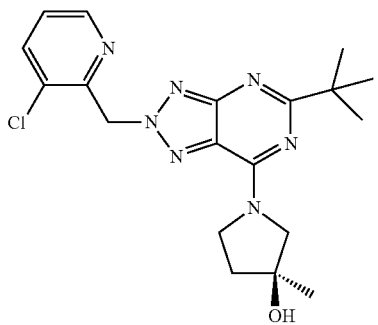

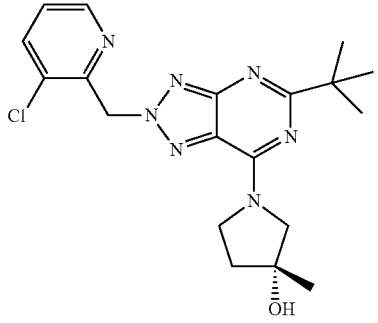

In analogy to the procedure described for the synthesis of (R)-1-(5-tert-butyl-3-((1-methyl-1H-tetrazol-5-yl)methyl)-

3H-[1,2,3]triazolo[4,5-d]pyrimidin-7-yl)pyrrolidin-3-ol (example 113, b) (S)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 3-chloro-2-(chloromethyl)pyridine. MS (m/e): 402.4 (MH+).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (R)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 3-chloro-2-(chloromethyl)pyridine. MS (m/e): 402.4 (MH+).

Example 128-a and Example 128-b (S)-1-[5-tert-Butyl-2-(5-methyl-[1,3,4]oxadiazol-2-ylmethyl)-2H-[1,2,3]triazolo[4,5-d]pyrimidin-7-yl]-3-methyl-pyrrolidin-3-ol and (R)-1-[5-tert-Butyl-2-(5-methyl-[1,3,4]oxadiazol-2-ylmethyl)-2H-[1,2,3]triazolo[4,5-d]pyrimidin-7-yl]-3-methyl-pyrrolidin-3-ol

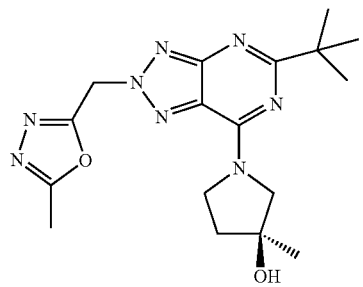

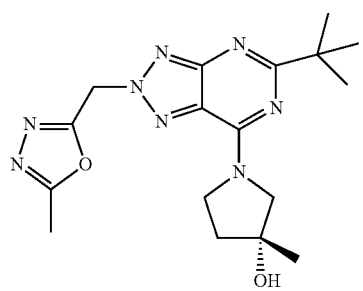

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (S)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 2-(chloromethyl)-5-methyl-1,3,4-oxadiazole. MS (m/e): 373.4 (MH+).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (R)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 2-(chloromethyl)-5-methyl-1,3,4-oxadiazole. MS (m/e): 373.4 (MH+).

Example 129-a and Example 129-b (S)-1-[5-tert-Butyl-2-(3-methyl-[1,2,4]oxadiazol-5-ylmethyl)-2H-[1,2,3]triazolo[4,5-d]pyrimidin-7-yl]-3-methyl-pyrrolidin-3-ol and (R)-1-[5-tert-Butyl-2-(3-methyl-[1,2,4]oxadiazol-5-ylmethyl)-2H-[1,2,3]triazolo[4,5-d]pyrimidin-7-yl]-3-methyl-pyrrolidin-3-ol

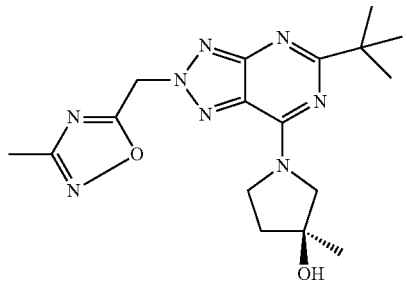

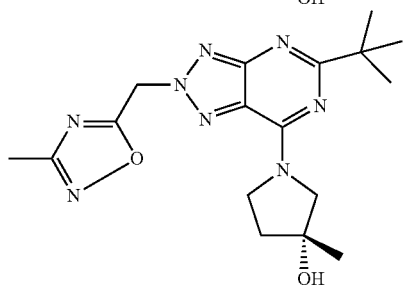

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (S)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 5-(chloromethyl)-3-methyl-1,2,4-oxadiazole. MS (m/e): 373.4 (MH+).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (R)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 5-(chloromethyl)-3-methyl-1,2,4-oxadiazole. MS (m/e): 373.4 (MH+).

Example 130-a and Example 130-b (S)-1-[5-tert-Butyl-2-(1-methyl-1H-tetrazol-5-ylmethyl)-2H-[1,2,3]triazolo[4,5-d]pyrimidin-7-yl]-3-methyl-pyrrolidin-3-ol and (R)-1-[5-tert-Butyl-2-(1-methyl-1H-tetrazol-5-ylmethyl)-2H-[1,2,3]triazolo[4,5-d]pyrimidin-7-yl]-3-methyl-pyrrolidin-3-ol

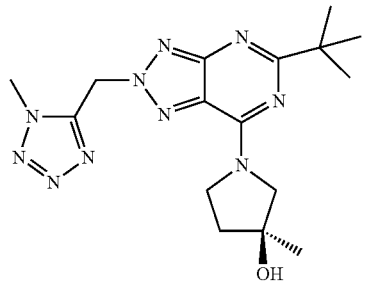

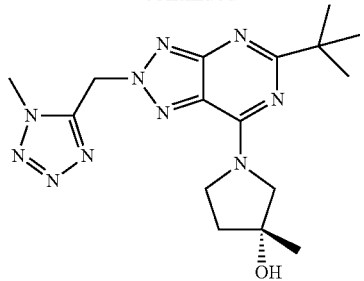

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (S)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 5-(chloromethyl)-1-methyl-1H-tetrazole. MS (m/e): 373.4 (MH⁺).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (R)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 5-(chloromethyl)-1-methyl-1H-tetrazole. MS (m/e): 373.4 (MH⁺).

Example 131-a and Example 131-b (S)-1-[5-tert-Butyl-2-(4-methyl-furazan-3-ylmethyl)-2H-[1,2,3]triazolo[4,5-d]pyrimidin-7-yl]-3-methyl-pyrrolidin-3-ol and (R)-1-[5-tert-Butyl-2-(4-methyl-furazan-3-ylmethyl)-2H-[1,2,3]triazolo[4,5-d]pyrimidin-7-yl]-3-methyl-pyrrolidin-3-ol

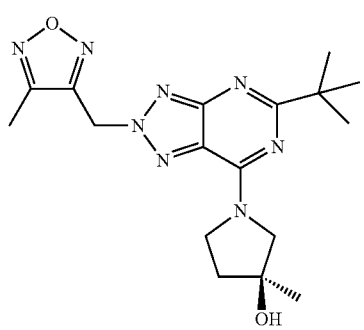

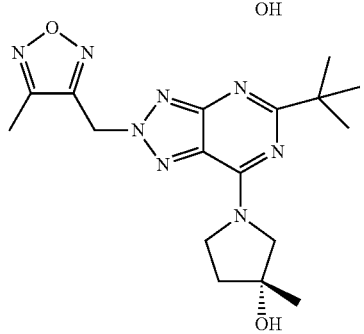

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (S)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 3-(bromomethyl)-4-methyl-1,2,5-oxadiazole. MS (m/e): 373.4 (MH⁺).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (R)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 3-(bromomethyl)-4-methyl-1,2,5-oxadiazole. MS (m/e): 373.4 (MH⁺).

Example 132-a and Example 132-b (S)-1-[5-tert-Butyl-2-(3,3,3-trifluoro-propyl)-2H-[1,2,3]triazolo[4,5-d]pyrimidin-7-yl]-3-methyl-pyrrolidin-3-ol and (R)-1-[5-tert-Butyl-2-(3,3,3-trifluoro-propyl)-2H-[1,2,3]triazolo[4,5-d]pyrimidin-7-yl]-3-methyl-pyrrolidin-3-ol

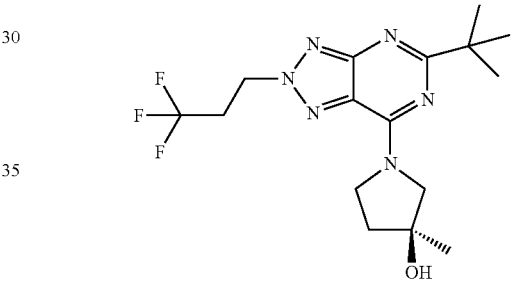

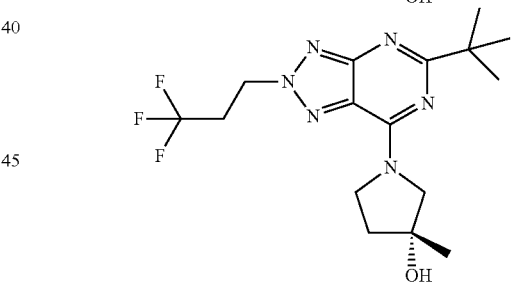

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (S)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 3-bromo-1,1,1-trifluoropropane. MS (m/e): 373.4 (MH⁺).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (R)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 3-bromo-1,1,1-trifluoropropane. MS (m/e): 373.4 (MH⁺).

Example 133-a and Example 133-b (S)-1-[5-tert-Butyl-2-(1-cyclopropyl-1H-tetrazol-5-ylmethyl)-2H-[1,2,3]triazolo[4,5-d]pyrimidin-7-yl]-3-methyl-pyrrolidin-3-ol and (R)-1-[5-tert-Butyl-2-(1-cyclopropyl-1H-tetrazol-5-ylmethyl)-2H-[1,2,3]triazolo[4,5-d]pyrimidin-7-yl]-3-methyl-pyrrolidin-3-ol

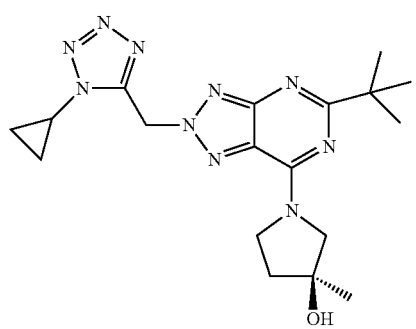

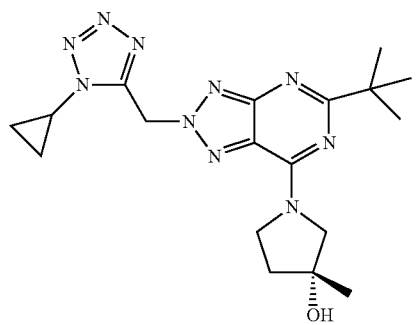

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (S)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 5-(chloromethyl)-1-cyclopropyl-1H-tetrazole. MS (m/e): 399.4 (MH$^+$).

In analogy to the procedure described for the synthesis of (R)-1-(5-tert-butyl-3-((1-methyl-1H-tetrazol-5-yl)methyl)-3H-[1,2,3]triazolo[4,5-d]pyrimidin-7-yl)pyrrolidin-3-ol (example 113, b) (R)-1-[5-tert-Butyl-2-(2-chloro-benzyl)-2H-[1,2,3]triazolo[4,5-d]pyrimidin-7-yl]-3-methyl-pyrrolidin-3-ol was hydrogenated and subsequently reacted with 5-(chloromethyl)-1-cyclopropyl-1H-tetrazole. MS (m/e): 399.4 (MH$^+$).

Example 134

N—{(S)-1-[2-(2-Chloro-benzyl)-5-(2,2-dimethyl-propoxy)-2H-[1,2,3]triazolo[4,5-d]pyrimidin-7-yl]-pyrrolidin-3-yl}-acetamide

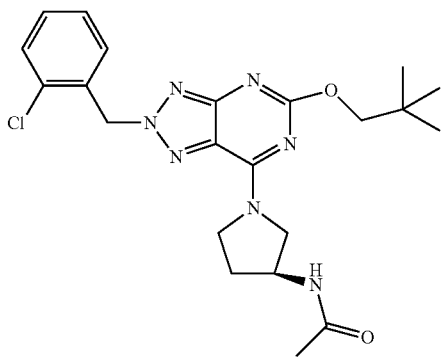 [SMILES: CC(=O)N[C@H]1CCN(c2nc(OCC(C)(C)C)nc3nn(Cc4ccccc4Cl)nc23)C1]

a) N—{(S)-1-[5-Chloro-3-(4-methoxy-benzyl)-3H-[1,2,3]triazolo[4,5-d]pyrimidin-7-yl]-pyrrolidin-3-yl}-acetamide

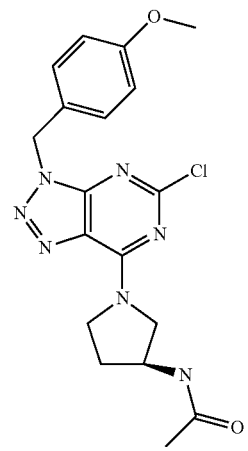 [SMILES: COc1ccc(Cn2nnc3c(N4CC[C@H](NC(C)=O)C4)nc(Cl)nc32)cc1]

In analogy to the procedure described for the synthesis of (S)-1-[5-Chloro-3-(4-methoxy-benzyl)-3H-[1,2,3]triazolo[4,5-d]pyrimidin-7-yl]-pyrrolidin-3-ol (example 108, c) the title compound was prepared from 5,7-Dichloro-3-(4-methoxy-benzyl)-3H-[1,2,3]triazolo[4,5-d]pyrimidine and (S)—N-Pyrrolidin-3-yl-acetamide and used in the consecutive step without further purification.

b) N—{(S)-1-[5-(2,2,2-Trifluoro-ethoxy)-3H-[1,2,3]triazolo[4,5-d]pyrimidin-7-yl]-pyrrolidin-3-yl}-acetamide

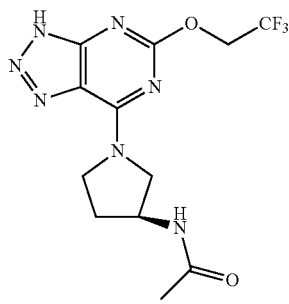 [SMILES: CC(=O)N[C@H]1CCN(c2nc(OCC(F)(F)F)nc3[nH]nnc23)C1]

In analogy to the procedure described for the synthesis of (S)-1-[5-(2,2,2-Trifluoro-ethoxy)-3H-[1,2,3]triazolo[4,5-d]pyrimidin-7-yl]-pyrrolidin-3-ol (example 108, e) the title compound was prepared from N—{(S)-1-[5-Chloro-3-(4-methoxy-benzyl)-3H-[1,2,3]triazolo[4,5-d]pyrimidin-7-yl]-pyrrolidin-3-yl}-acetamide (example 134, a) through nucleophilic substitution with 2,2,2-trifluoro-ethanol and subsequent cleavage of the 4-methoxy benzyl group with TFA and used crude in the subsequent step.

c) N—{(S)-1-[2-(2-Chloro-benzyl)-5-(2,2-dimethyl-propoxy)-2H-[1,2,3]triazolo[4,5-d]pyrimidin-7-yl]-pyrrolidin-3-yl}-acetamide In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from N—{(S)-1-[5-(2,2,2-Trifluoro-ethoxy)-3H-[1,2,3]triazolo[4,5-d]pyrimidin-7-yl]-pyrrolidin-3-yl}-acetamide and 1-(bromomethyl)-2-chlorobenzene. MS (m/e): 458.4 (MH$^+$).

Example 135

N—{(S)-1-[2-(3-Chloro-pyridin-2-ylmethyl)-5-(2,2-dimethyl-propoxy)-2H-[1,2,3]triazolo[4,5-d]pyrimidin-7-yl]-pyrrolidin-3-yl}-acetamide

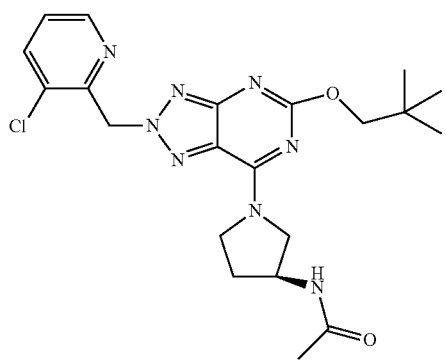 [SMILES: CC(=O)N[C@H]1CCN(c2nc(OCC(C)(C)C)nc3nn(Cc4ncccc4Cl)nc23)C1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from N—{(S)-1-[5-(2,2,2-Trifluoro-ethoxy)-3H-[1,2,3]triazolo[4,5-d]pyrimidin-7-yl]-pyrrolidin-3-yl}-acetamide and 3-chloro-2-(chloromethyl)pyridine. MS (m/e): 459.4 (MH$^+$).

Example 136 tert-Butyl-[7-(3,3-difluoro-pyrrolidin-1-yl)-2-(2-trifluoromethyl-benzyl)-2H-[1,2,3]triazolo[4,5-d]pyrimidin-5-yl]-amine

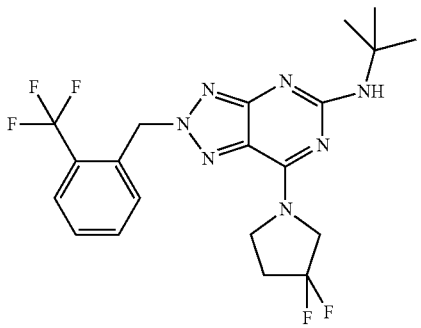 [SMILES: CC(C)(C)Nc1nc(N2CCC(F)(F)C2)c2nn(Cc3ccccc3C(F)(F)F)nc2n1]

a) tert-Butyl-[7-(3,3-difluoro-pyrrolidin-1-yl)-3H-[1,2,3]triazolo[4,5-d]pyrimidin-5-yl]-amine

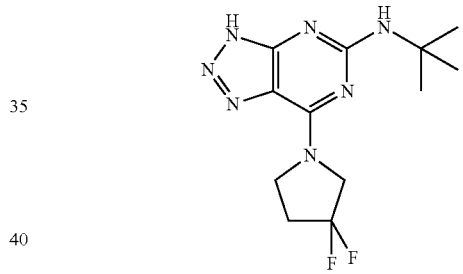

In analogy to the procedure described for the synthesis of (S)-1-[5-(2,2,2-Trifluoro-ethoxy)-3H-[1,2,3]triazolo[4,5-d]pyrimidin-7-yl]-pyrrolidin-3-ol (example 108, e) the title compound was prepared from 5-Chloro-7-(3,3-difluoro-pyrrolidin-1-yl)-3-(4-methoxy-benzyl)-3H-[1,2,3]triazolo[4,5-d]pyrimidine (example 112, a) through nucleophilic substitution with tert-butylamine and subsequent cleavage of the 4-methoxy benzyl group with TFA and used crude in the subsequent step.

b) tert-Butyl-[7-(3,3-difluoro-pyrrolidin-1-yl)-2-(2-trifluoromethyl-benzyl)-2H-[1,2,3]triazolo[4,5-d]pyrimidin-5-yl]-amine In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from tert-Butyl-[7-(3,3-difluoro-pyrrolidin-1-yl)-3H-[1,2,3]triazolo[4,5-d]pyrimidin-5-yl]-amine and 1-(bromomethyl)-2-(trifluoromethyl)benzene. MS (m/e): 456.4 (MH$^+$).

Example 137 tert-Butyl-[7-(3,3-difluoro-pyrrolidin-1-yl)-2-(2-methanesulfonyl-benzyl)-2H-[1,2,3]triazolo[4,5-d]pyrimidin-5-yl]-amine

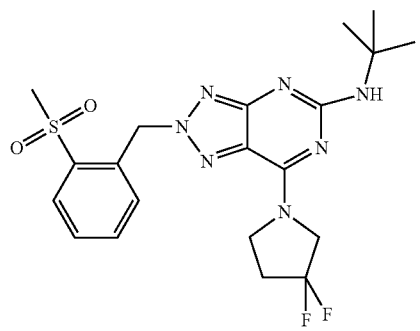 [SMILES: CC(C)(C)Nc1nc(N2CCC(F)(F)C2)c2nn(Cc3ccccc3S(C)(=O)=O)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from tert-Butyl-[7-(3,3-difluoro-pyrrolidin-1-yl)-3H-[1,2,3]triazolo[4,5-d]pyrimidin-5-yl]-amine and 1-(bromomethyl)-2-(methylsulfonyl)benzene. MS (m/e): 466.4 (MH$^+$)

Example 138 tert-Butyl-[2-(3-chloro-pyridin-2-ylmethyl)-7-(3,3-difluoro-pyrrolidin-1-yl)-2H-[1,2,3]triazolo[4,5-d]pyrimidin-5-yl]-amine

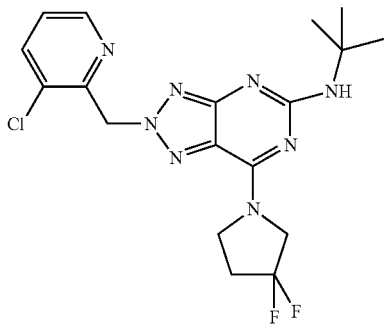 [SMILES: CC(C)(C)Nc1nc(N2CCC(F)(F)C2)c2nn(Cc3ncccc3Cl)nc2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from tert-Butyl-[7-(3,3-difluoro-pyrrolidin-1-yl)-3H-[1,2,3]triazolo[4,5-d]pyrimidin-5-yl]-amine and 3-chloro-2-(chloromethyl)pyridine. MS (m/e): 423.3 (MH$^+$).

Example 139 tert-Butyl-[7-(3,3-difluoro-pyrrolidin-1-yl)-2-(1-methyl-1H-tetrazol-5-ylmethyl)-2H-[1,2,3]triazolo[4,5-d]pyrimidin-5-yl]-amine

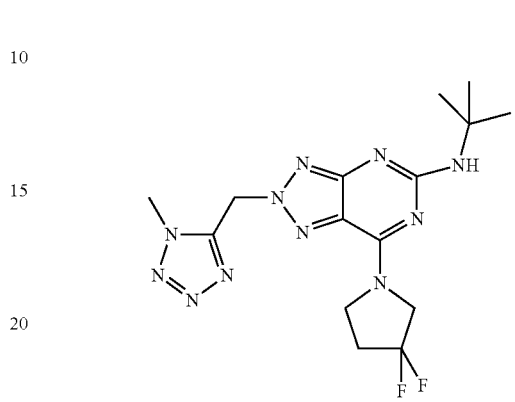

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from tert-Butyl-[7-(3,3-difluoro-pyrrolidin-1-yl)-3H-[1,2,3]triazolo[4,5-d]pyrimidin-5-yl]-amine and 5-(chloromethyl)-1-methyl-1H-tetrazole. MS (m/e): 394.4 (MH$^+$).

Example 140 tert-Butyl-[7-(3,3-difluoro-pyrrolidin-1-yl)-2-(4-methyl-furazan-3-ylmethyl)-2H-[1,2,3]triazolo[4,5-d]pyrimidin-5-yl]-amine

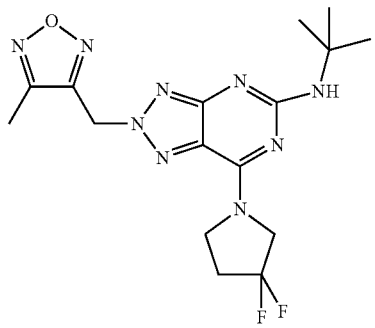 [SMILES: Cc1nonc1Cn1nc2nc(NC(C)(C)C)nc(N3CCC(F)(F)C3)c2n1]

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from tert-Butyl-[7-(3,3-difluoro-pyrrolidin-1-yl)-3H-[1,2,3]triazolo[4,5-d]pyrimidin-5-yl]-amine and 3-(bromomethyl)-4-methyl-1,2,5-oxadiazole. MS (m/e): 394.4 (MH$^+$)

Example 141

N—{(S)-1-[2-(2-Chloro-benzyl)-5-((S)-2,2,2-trifluoro-1-methyl-ethoxy)-2H-[1,2,3]triazolo[4,5-d]pyrimidin-7-yl]-pyrrolidin-3-yl}-acetamide

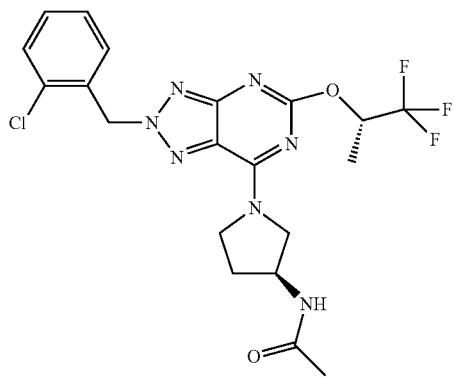 [SMILES: CC(=O)N[C@H]1CCN(c2nc(O[C@@H](C)C(F)(F)F)nc3nn(Cc4ccccc4Cl)nc23)C1]

a) N—{(S)-1-[5-((S)-2,2,2-Trifluoro-1-methylethoxy)-3H-[1,2,3]triazolo[4,5-d]pyrimidin-7-yl]-pyrrolidin-3-yl}-acetamide

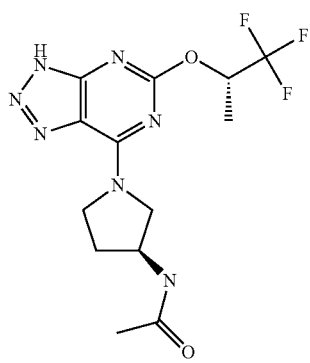 [SMILES: CC(=O)N[C@H]1CCN(c2nc(O[C@@H](C)C(F)(F)F)nc3[nH]nnc23)C1]

In analogy to the procedure described for the synthesis of (S)-1-[5-(2,2,2-Trifluoro-ethoxy)-3H-[1,2,3]triazolo[4,5-d]pyrimidin-7-yl]-pyrrolidin-3-ol (example 108, e) the title compound was prepared from N—{(S)-1-[5-Chloro-3-(4-methoxy-benzyl)-3H-[1,2,3]triazolo[4,5-d]pyrimidin-7-yl]-pyrrolidin-3-yl}-acetamide (example 134, a) through nucleophilic substitution with (S)-1,1,1-Trifluoro-propan-2-ol and subsequent cleavage of the 4-methoxy benzyl group through hydrogenation and used crude in the subsequent step.

b) N—{(S)-1-[2-(2-Chloro-benzyl)-5-((S)-2,2,2-trifluoro-1-methyl-ethoxy)-2H-[1,2,3]triazolo[4,5-d]pyrimidin-7-yl]-pyrrolidin-3-yl}-acetamide In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from N—{(S)-1-[5-((S)-2,2,2-Trifluoro-1-methyl-ethoxy)-3H-[1,2,3]triazolo[4,5-d]pyrimidin-7-yl]-pyrrolidin-3-yl}-acetamide and 1-(bromomethyl)-2-chlorobenzene. MS (m/e): 484.4 (MH$^+$).

Example 142

N—{(S)-1-[2-(2-Trifluoromethyl-benzyl)-5-((S)-2,2,2-trifluoro-1-methyl-ethoxy)-2H-[1,2,3]triazolo[4,5-d]pyrimidin-7-yl]-pyrrolidin-3-yl}-acetamide

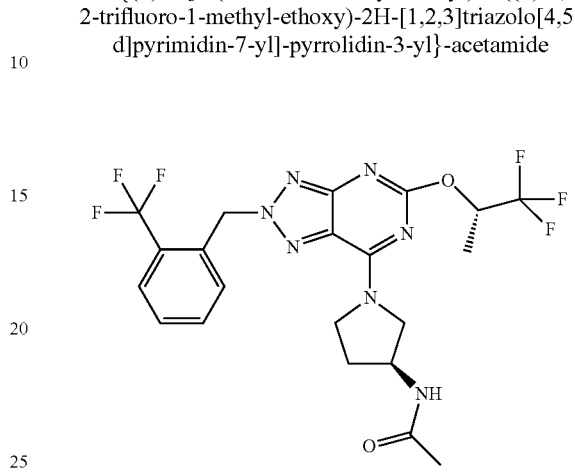

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from N—{(S)-1-[5-((S)-2,2,2-Trifluoro-1-methyl-ethoxy)-3H-[1,2,3]triazolo[4,5-d]pyrimidin-7-yl]-pyrrolidin-3-yl}-acetamide and 1-(bromomethyl)-2-(trifluoromethyl)benzene. MS (m/e): 518.5 (MH$^+$).

Example 143

N—{(S)-1-[2-(2-Methanesulfonyl-benzyl)-5-((S)-2,2,2-trifluoro-1-methyl-ethoxy)-2H-[1,2,3]triazolo[4,5-d]pyrimidin-7-yl]-pyrrolidin-3-yl}-acetamide

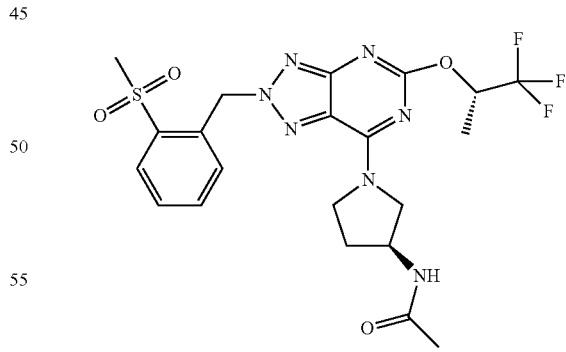

In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from N—{(S)-1-[5-((S)-2,2,2-Trifluoro-1-methyl-ethoxy)-3H-[1,2,3]triazolo[4,5-d]pyrimidin-7-yl]-pyrrolidin-3-yl}-acetamide and 1-(bromomethyl)-2-(methylsulfonyl)benzene. MS (m/e): 528.5 (MH$^+$).

Example 144

N—{(S)-1-[5-tert-Butylamino-2-(2-chloro-benzyl)-2H-[1,2,3]triazolo[4,5-d]pyrimidin-7-yl]-pyrrolidin-3-yl}-acetamide

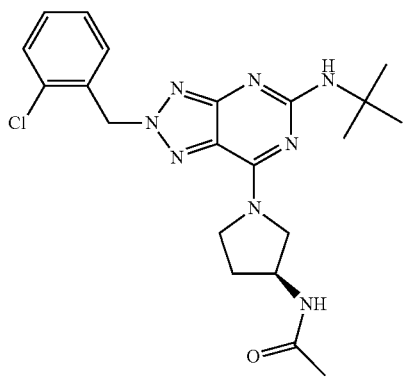 [SMILES: CC(=O)N[C@H]1CCN(c2nc(NC(C)(C)C)nc3nn(Cc4ccccc4Cl)nc23)C1]

a) N—[(S)-1-(5-tert-Butylamino-3H-[1,2,3]triazolo[4,5-d]pyrimidin-7-yl)-pyrrolidin-3-yl]-acetamide

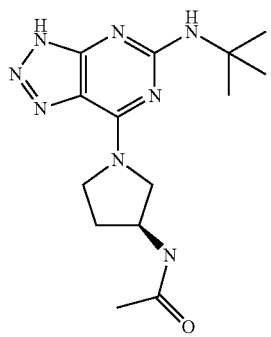 [SMILES: CC(=O)N[C@H]1CCN(c2nc(NC(C)(C)C)nc3[nH]nnc23)C1]

In analogy to the procedure described for the synthesis of (S)-1-[5-(2,2,2-Trifluoro-ethoxy)-3H-[1,2,3]triazolo[4,5-d]pyrimidin-7-yl]-pyrrolidin-3-ol (example 108, e) the title compound was prepared from N—{(S)-1-[5-Chloro-3-(4-methoxy-benzyl)-3H-[1,2,3]triazolo[4,5-d]pyrimidin-7-yl]-pyrrolidin-3-yl}-acetamide (example 134, a) through nucleophilic substitution with tert-butylamine and subsequent cleavage of the 4-methoxy benzyl group through hydrogenation and used crude in the subsequent step.

b) N—{(S)-1-[5-tert-Butylamino-2-(2-chloro-benzyl)-2H-[1,2,3]triazolo[4,5-d]pyrimidin-7-yl]-pyrrolidin-3-yl}-acetamide In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from N—[(S)-1-(5-tert-Butylamino-3H-[1,2,3]triazolo[4,5-d]pyrimidin-7-yl)-pyrrolidin-3-yl]-acetamide and 1-(bromomethyl)-2-chlorobenzene. MS (m/e): 443.4 (MH$^+$).

Example 145

(S)-1-[5-tert-Butylamino-2-(1-methyl-1H-tetrazol-5-ylmethyl)-2H-[1,2,3]triazolo[4,5-d]pyrimidin-7-yl]-pyrrolidin-3-ol

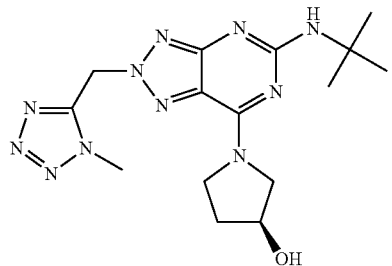 [SMILES: Cn1nnnc1Cn1nc2nc(NC(C)(C)C)nc(N3CC[C@H](O)C3)c2n1]

a) (S)-1-(5-tert-Butylamino-3H-[1,2,3]triazolo[4,5-d]pyrimidin-7-yl)-pyrrolidin-3-ol

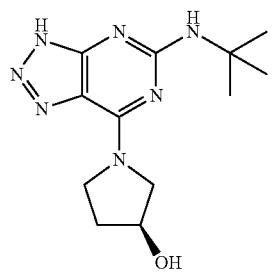 [SMILES: CC(C)(C)Nc1nc(N2CC[C@H](O)C2)c2nn[nH]c2n1]

In analogy to the procedure described for the synthesis of d) (S)-1-[3-(4-Methoxy-benzyl)-5-(2,2,2-trifluoro-ethoxy)-3H-[1,2,3]triazolo[4,5-d]pyrimidin-7-yl]-pyrrolidin-3-ol (example 109, d) the title compound was prepared from (S)-1-[5-Chloro-3-(4-methoxy-benzyl)-3H-[1,2,3]triazolo[4,5-d]pyrimidin-7-yl]-pyrrolidin-3-ol (example 109, c) and tert-butyl amine, subsequent cleavage of the PMB protecting group and used in the consecutive step without further purification.

b) (S)-1-[5-tert-Butylamino-2-(1-methyl-1H-tetrazol-5-ylmethyl)-2H-[1,2,3]triazolo[4,5-d]pyrimidin-7-yl]-pyrrolidin-3-ol In analogy to the procedure described for the synthesis of 5-tert-butyl-7-(3,3-difluoro-pyrrolidin-1-yl)-2-ethyl-2H-[1,2,3]triazolo[4,5-d]pyrimidine (example 3, step b), the title compound was prepared from (S)-1-(5-tert-Butylamino-3H-[1,2,3]triazolo[4,5-d]pyrimidin-7-yl)-pyrrolidin-3-ol and 5-(chloromethyl)-1-methyl-1H-tetrazole. MS (m/e): 374.3 (MH$^+$).

Example 146

Pharmacological Tests

The following tests were carried out in order to determine the activity of the compounds of formula I:
Radioligand Binding Assay
The affinity of the compounds of the invention for cannabinoid CB1 receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM $MgCl_2$, 2.5 mM EDTA, and 0.5% (wt/vol) fatty acid free BSA, pH 7.4 for CB1 receptor and 50 mM Tris, 5 mM $MgCl_2$, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using nonlinear regression analysis (Activity Base, ID Business Solution, Limited), with the Kd values for [3H]CP55,940 determined from saturation experiments. The compounds of formula (I) show an excellent affinity for the CB2 receptor with affinities below 10 µM, more particularly of 1 nM to 3 µM and most particularly of 1 nM to 100 nM. The compounds according to formula I have an activity in the above assay (Ki) particularly of 0.5 nM to 10 µM, more particularly of 0.5 nM to 3 µM and most particularly of 0.5 nM to 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µl and incubated for 30 min at 30° C. Using the cAMP-Nano-TRF detection kit the assay (Roche Diagnostics) was stopped by the addition of 50 µl lysis reagent (Tris, NaCl, 1.5% Triton X100, 2.5% NP40, 10% $NaN_3$) and 50 µl detection solutions (20 µM mAb Alexa700-cAMP 1:1, and 48 µM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.1 nM cAMP.

$EC_{50}$ values were determined using Activity Base analysis (ID Business Solution, Limited). The $EC_{50}$ values for a wide range of cannabinoid agonists generated from this assay were in agreement with the values published in the scientific literature.

All compounds are CB2 agonists with $EC_{50}$ below 3 uM, particularly below 1 uM, more particularly below 0.5 uM, and selectivity versus CB1 in the corresponding assay of at least 10 fold.

For example, the following compounds showed the following human $EC_{50}$ values in the functional cAMP assay described above:

| Example | human CB2 $EC_{50}$ [µM] | human CB2 $EC_{50}$ [µM] |
|---|---|---|
| 1 | 0.0033 | >10 |
| 2 | 0.0022 | >10 |
| 3 | 0.0185 | >10 |
| 4 | 0.008 | >10 |
| 5 | 0.0647 | >10 |
| 6 | 0.0005 | 0.306 |
| 7 | 0.0041 | >10 |
| 8 | 0.0065 | >10 |
| 9 | 0.0034 | >10 |
| 10 | 0.0041 | >10 |
| 11 | 0.0012 | >10 |
| 12 | 0.0015 | >10 |
| 13 | 0.001 | >10 |
| 14 | 0.0005 | 0.065 |
| 15 | 0.0007 | 0.21 |
| 16 | 0.0039 | >10 |
| 17 | 0.0008 | >10 |
| 18 | 0.0014 | >10 |
| 19 | 0.0022 | >10 |
| 20 | 0.0002 | 0.034 |
| 21 | 0.0001 | 0.183 |
| 22 | 0.0002 | >10 |
| 23 | 0.0002 | 0.086 |
| 24 | 0.0004 | >10 |
| 25 | 0.0001 | 0.205 |
| 26 | 0.0013 | 0.386 |
| 27 | 0.0009 | >10 |
| 28 | 0.0002 | 0.134 |
| 29 | 0.0008 | 0.098 |
| 30 | 0.0007 | nd |
| 31 | 0.0005 | nd |
| 32 | 0.019 | nd |
| 33 | 0.0012 | >10 |
| 34 | 0.0005 | >10 |
| 35 | 0.0005 | 0.6416 |
| 36 | 0.0002 | 0.0203 |
| 37 | 0.0009 | >10 |
| 38 | 0.0011 | 0.0986 |
| 39 | 0.0002 | >10 |
| 40 | 0.0043 | >10 |
| 41 | 0.0005 | 0.4975 |
| 42 | 0.0106 | >10 |
| 43 | 0.022 | >10 |
| 44 | 0.0002 | 0.4545 |
| 45 | 0.0076 | >10 |
| 46 | 0.0028 | >10 |
| 47 | 0.0006 | >10 |
| 48 | 0.0055 | >10 |
| 49 | 0.0004 | 0.1498 |
| 50 | 0.0015 | >10 |
| 51 | 0.0009 | >10 |
| 52 | 0.013 | >10 |
| 53 | 0.0072 | >10 |
| 54 | 0.0065 | >10 |
| 55 | 0.0087 | >10 |
| 56 | 0.0126 | >10 |
| 57 | 0.0036 | >10 |
| 58 | 0.0043 | >10 |
| 59 | 0.0035 | >10 |
| 60 | 0.0127 | >10 |
| 61 | 0.0026 | >10 |
| 62 | 0.0058 | >10 |
| 63 | 0.004 | >10 |
| 64 | 0.0024 | >10 |
| 65 | 0.0186 | >10 |
| 66 | 0.0004 | 0.2337 |
| 67 | 0.0013 | 1.6275 |
| 68 | 0.0023 | >10 |
| 69 | 0.0011 | >10 |
| 70 | 0.0336 | >10 |
| 71 | 0.0014 | 0.105 |
| 72 | 0.0118 | >10 |
| 73 | 0.0071 | >10 |
| 74 | 0.0613 | >10 |
| 75 | 0.0046 | >10 |
| 76 | 0.0059 | >10 |
| 77 | 0.0155 | >10 |
| 78 | 0.006 | >10 |

| Example | human CB2 EC$_{50}$ [μM] | human CB2 EC$_{50}$ [μM] |
|---|---|---|
| 79 | 0.0004 | >10 |
| 80 | 0.0103 | >10 |
| 81 | 0.0094 | >10 |
| 82 | 0.0028 | >10 |
| 83 | 0.0061 | >10 |
| 84 | 0.094 | >10 |
| 85 | 0.0102 | >10 |
| 86 | 0.0522 | >10 |
| 87 | 0.2578 | >10 |
| 88 | 0.0521 | >10 |
| 89 | 0.3715 | >10 |
| 90 | 0.0407 | >10 |
| 91 | 0.1244 | >10 |
| 92 | 0.005 | 1.576 |
| 93 | 0.2695 | >10 |
| 94 | 0.2514 | >10 |
| 95 | 0.2574 | >10 |
| 96 | 0.0226 | >10 |
| 97 | 0.1445 | >10 |
| 98 | 0.2108 | >10 |
| 99 | 0.0009 | >10 |
| 100 | 0.0046 | >10 |
| 101 | 0.0157 | >10 |
| 102 | 0.0063 | >10 |
| 103 | 0.0209 | >10 |
| 104 | 0.0101 | >10 |
| 105 | 0.1103 | >10 |
| 106 | 0.0627 | >10 |
| 107 | 0.0084 | >10 |
| 108 | 0.0052 | 0.3625 |
| 109 | 0.1066 | >10 |
| 110 | 0.06 | >10 |
| 111 | 0.2654 | >10 |
| 112 | 0.0309 | >10 |
| 113 | 1.6631 | >10 |
| 114 | 0.1644 | >10 |
| 115 | 0.0312 | >10 |
| 116 | 0.0231 | >10 |
| 117 | 0.0212 | >10 |
| 118 | 0.4409 | >10 |
| 119 | 0.4393 | >10 |
| 120 | 0.0694 | >10 |
| 121 | 0.0075 | >10 |
| 122 | 0.0084 | >10 |
| 123 | 0.0493 | >10 |
| 124-a | 0.0025 | >10 |
| 124-b | 0.0068 | >10 |
| 125-a | 0.0004 | 0.3978 |
| 125-b | 0.0037 | >10 |
| 126-a | 0.0106 | >10 |
| 126-b | 0.024 | >10 |
| 127-a | 0.0051 | 0.7573 |
| 127-b | 0.0119 | 0.6091 |
| 128-a | 0.0702 | >10 |
| 128-b | 0.7891 | >10 |
| 129-a | 0.1968 | >10 |
| 129-b | 0.3164 | >10 |
| 130-a | 0.1718 | >10 |
| 130-b | 0.7985 | >10 |
| 131-a | 0.0102 | >10 |
| 131-b | 0.0614 | >10 |
| 132-a | 0.0181 | >10 |
| 132-b | 0.0698 | >10 |
| 133-a | 0.1255 | >10 |
| 133-b | 0.5466 | >10 |
| 134 | 0.6818 | >10 |
| 135 | 0.6056 | >10 |
| 136 | 0.035 | >10 |
| 137 | 0.0053 | >10 |
| 138 | 0.054 | >10 |
| 139 | 0.0281 | >10 |
| 140 | 0.0061 | >10 |
| 141 | 1.15 | >10 |
| 142 | 1.11 | >10 |
| 143 | 1.73 | >10 |
| 144 | 1.95 | >10 |
| 145 | 1.09 | >10 |

β-Arrestin Translocation Assay—Pathhunter™ (DiscoveRx)

PathHunter™ β-arrestin CHO-K1 CNR1 cell line (catalog number #93-0200C2) and the β-arrestin CHO-K1 CNR2 cell line (catalog number #93-0706C2) were purchased from DiscoveRx Corporation. The cell line was engineered to express the β-galactosidase EA fragment fused to β-arrestin and the ProLink complementary peptide fused to the target receptor. The PathHunter™ protein complementation assay (DiscoveRx Corporation #93-0001) was performed according to the manufacturer's protocol. Assay plates were seeded containing 7500 (CNR1) and 10000 (CNR2) cells in 384 well plates (Corning Costar #3707, white, clear bottom) in 20 μL cell plating reagent 2 (Discoverx #93-0563R2A). After incubation at 37° C. (5% CO$_2$, 95% relative humidity) overnight, 5 μl of test compound was added (1% final DMSO concentration) and the incubation continued at 30° C. for 90 min. Detection reagent (12 μl) was then added and the incubation continued at room temperature for 60 min. Plates were then analyzed for a chemiluminescent signal using a Victor $^3$V reader (Perkin Elmer).

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
| --- | --- |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

What is claimed is:

1. A compound selected from the group consisting of
5-tert-Butyl-2-(2-chloro-benzyl)-7-morpholin-4-yl-2H-[1,2,3]triazolo[4,5-d]pyrimidine;
5-tert-Butyl-2-(2-chloro-4-fluoro-benzyl)-7-morpholin-4-yl-2H-[1,2,3]triazolo[4,5-d]pyrimidine;
5-tert-Butyl-7-(3,3-difluoro-pyrrolidin-1-yl)-2-ethyl-2H-[1,2,3]triazolo[4,5-d]pyrimidine;
5-tert-Butyl-7-(3,3-difluoro-pyrrolidin-1-yl)-2-(2-methoxy-ethyl)-2H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-2-yl]-ethanol;
5-tert-Butyl-2-cyclohexylmethyl-7-(3,3-difluoro-pyrrolidin-1-yl)-2H-[1,2,3]triazolo[4,5-d]pyrimidine;
5-tert-Butyl-2-(3-chloro-benzyl)-7-(3,3-difluoro-pyrrolidin-1-yl)-2H-[1,2,3]triazolo[4,5-d]pyrimidine;
5-tert-Butyl-2-(4-chloro-benzyl)-7-(3,3-difluoro-pyrrolidin-1-yl)-2H-[1,2,3]triazolo[4,5-d]pyrimidine;
5-tert-Butyl-2-(2,3-dichloro-benzyl)-7-(3,3-difluoro-pyrrolidin-1-yl)-2H-[1,2,3]triazolo[4,5-d]pyrimidine;
5-tert-Butyl-2-(2,4-dichloro-benzyl)-7-(3,3-difluoro-pyrrolidin-1-yl)-2H-[1,2,3]triazolo[4,5-d]pyrimidine;
5-tert-Butyl-2-(2,5-dichloro-benzyl)-7-(3,3-difluoro-pyrrolidin-1-yl)-2H-[1,2,3]triazolo[4,5-d]pyrimidine;
5-tert-Butyl-2-(2,6-dichloro-benzyl)-7-(3,3-difluoro-pyrrolidin-1-yl)-2H-[1,2,3]triazolo[4,5-d]pyrimidine;
5-tert-Butyl-2-(2-chloro-4-fluoro-benzyl)-7-(3,3-difluoro-pyrrolidin-1-yl)-2H-[1,2,3]triazolo[4,5-d]pyrimidine;
5-tert-Butyl-2-(2-chloro-6-fluoro-benzyl)-7-(3,3-difluoro-pyrrolidin-1-yl)-2H-[1,2,3]triazolo[4,5-d]pyrimidine; and
5-tert-Butyl-7-(3,3-difluoro-pyrrolidin-1-yl)-2-pyridin-2-ylmethyl-2H-[1,2,3]triazolo[4,5-d]pyrimidine.

2. A compound selected from the group consisting of
5-tert-Butyl-7-(3,3-difluoro-pyrrolidin-1-yl)-2-pyridin-3-ylmethyl-2H-[1,2,3]triazolo[4,5-d]pyrimidine;
5-tert-Butyl-7-(3,3-difluoro-pyrrolidin-1-yl)-2-pyridin-4-ylmethyl-2H-[1,2,3]triazolo[4,5-d]pyrimidine;
5-tert-Butyl-7-(3,3-difluoro-pyrrolidin-1-yl)-2-(2,2,2-trifluoro-ethyl)-2H-[1,2,3]triazolo[4,5-d]pyrimidine;
5-tert-Butyl-2-(2-chloro-4,5-difluoro-benzyl)-7-(3,3-difluoro-pyrrolidin-1-yl)-2H-[1,2,3]triazolo[4,5-d]pyrimidine;
5-tert-Butyl-2-(2-chloro-3,6-difluoro-benzyl)-7-(3,3-difluoro-pyrrolidin-1-yl)-2H-[1,2,3]triazolo[4,5-d]pyrimidine;
2-(2-Bromo-benzyl)-5-tert-butyl-7-(3,3-difluoro-pyrrolidin-1-yl)-2H-[1,2,3]triazolo[4,5-d]pyrimidine;
5-tert-Butyl-7-(3,3-difluoro-pyrrolidin-1-yl)-2-(2-trifluoromethyl-benzyl)-2H-[1,2,3]triazolo[4,5-d]pyrimidine;
5-tert-Butyl-7-(3,3-difluoro-pyrrolidin-1-yl)-2-(2-methoxy-benzyl)-2H-[1,2,3]triazolo[4,5-d]pyrimidine;
5-tert-Butyl-7-(3,3-difluoro-pyrrolidin-1-yl)-2-(2-trifluoromethoxy-benzyl)-2H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-2-ylmethyl]benzonitrile;
5-tert-Butyl-7-(3,3-difluoro-pyrrolidin-1-yl)-2-phenethyl-2H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-2-yl]-1-phenyl-ethanone;
5-tert-Butyl-2-[(R)-1-(2-chloro-phenyl)-ethyl]-7-(3,3-difluoro-pyrrolidin-1-yl)-2H-[1,2,3]triazolo[4,5-d]pyrimidine;
5-tert-Butyl-2-[(S)-1-(2-chloro-phenyl)-ethyl]-7-(3,3-difluoro-pyrrolidin-1-yl)-2H-[1,2,3]triazolo[4,5-d]pyrimidine; and
5-tert-Butyl-2-(2-chloro-3-fluoro-benzyl)-7-(3,3-difluoro-pyrrolidin-1-yl)-2H-[1,2,3]triazolo[4,5-d]pyrimidine.

3. A compound selected from the group consisting of
5-tert-Butyl-2-(2-chloro-5-fluoro-benzyl)-7-(3,3-difluoro-pyrrolidin-1-yl)-2H-[1,2,3]triazolo[4,5-d]pyrimidine;
5-tert-Butyl-7-(3,3-difluoro-pyrrolidin-1-yl)-2-oxetan-3-yl-2H-[1,2,3]triazolo[4,5-d]pyrimidine;
5-tert-Butyl-2-(2,6-dichloro-3-fluoro-benzyl)-7-(3,3-difluoro-pyrrolidin-1-yl)-2H-[1,2,3]triazolo[4,5-d]pyrimidine;
5-tert-Butyl-2-(2-chloro-pyridin-3-ylmethyl)-7-(3,3-difluoro-pyrrolidin-1-yl)-2H-[1,2,3]triazolo[4,5-d]pyrimidine;
5-tert-Butyl-2-(4-chloro-pyridin-3-ylmethyl)-7-(3,3-difluoro-pyrrolidin-1-yl)-2H-[1,2,3]triazolo[4,5-d]pyrimidine;
5-tert-Butyl-2-(3-chloro-pyridin-2-ylmethyl)-7-(3,3-difluoro-pyrrolidin-1-yl)-2H-[1,2,3]triazolo[4,5-d]pyrimidine;
5-tert-Butyl-2-(2,5-dichloro-pyridin-3-ylmethyl)-7-(3,3-difluoro-pyrrolidin-1-yl)-2H-[1,2,3]triazolo[4,5-d]pyrimidine;
5-tert-Butyl-2-(3,6-dichloro-pyridin-2-ylmethyl)-7-(3,3-difluoro-pyrrolidin-1-yl)-2H-[1,2,3]triazolo[4,5-d]pyrimidine;
5-tert-Butyl-7-(3,3-difluoro-pyrrolidin-1-yl)-2-(4-methyl-furazan-3-ylmethyl)-2H-[1,2,3]triazolo[4,5-d]pyrimidine;
5-tert-Butyl-7-(3,3-difluoro-pyrrolidin-1-yl)-2-(3-methyl-[1,2,4]oxadiazol-5-ylmethyl)-2H-[1,2,3]triazolo[4,5-d]pyrimidine;
5-tert-Butyl-2-[2-(2-chloro-phenyl)-ethyl]-7-(3,3-difluoro-pyrrolidin-1-yl)-2H-[1,2,3]triazolo[4,5-d]pyrimidine;
5-tert-Butyl-2 [2-(3-chloro-phenyl)-ethyl]-7-(3,3-difluoro-pyrrolidin-1-yl)-2H-[1,2,3]triazolo[4,5-d]pyrimidine;

5-tert-Butyl-2-[2-(4-chloro-phenyl)-ethyl]-7-(3,3-difluoro-pyrrolidin-1-yl)-2H-[1,2,3]triazolo[4,5-d]pyrimidine;

5-tert-Butyl-2-(2,4-dichloro-pyridin-3-ylmethyl)-7-(3,3-difluoro-pyrrolidin-1-yl)-2H-[1,2,3]triazolo[4,5-d]pyrimidine; and 5-tert-Butyl-7-(3,3-difluoro-pyrrolidin-1-yl)-2-(R)-tetrahydro-furan-3-yl-2H-[1,2,3]triazolo[4,5 d]pyrimidine.

4. A compound selected from the group consisting of 5-tert-Butyl-7-(3,3-difluoro-pyrrolidin-1-yl)-2-(S)-tetrahydro-furan-3-yl-2H-[1,2,3]triazolo[4,5-d]pyrimidine;

2-[5-tert-Butyl-7-(3,3-difluoro-pyrrolidin-1-yl)-[1,2,3]triazolo[4,5-d]pyrimidin-2-yl]-1-(2-chloro-phenyl)-ethanone;

5-tert-Butyl-2-(2,3-dichloro-6-fluoro-benzyl)-7-(3,3-difluoro-pyrrolidin-1-yl)-2H-[1,2,3]triazolo[4,5-d]pyrimidine;

5-tert-Butyl-7-(3,3-difluoro-pyrrolidin-1-yl)-2-(2-methanesulfonyl-benzyl)-2H-[1,2,3]triazolo[4,5-d]pyrimidine;

5-tert-Butyl-7-(3,3-difluoro-pyrrolidin-1-yl)-2-(2-pyridin-2-yl-ethyl)-2H-[1,2,3]triazolo[4,5-d]pyrimidine;

5-tert-Butyl-7-(3,3-difluoro-pyrrolidin-1-yl)-2-(3-methyl-oxetan-3-ylmethyl)-2H-[1,2,3]triazolo[4,5-d]pyrimidine;

2-[5-tert-Butyl-7-(3,3-difluoro-pyrrolidin-1-yl)-[1,2,3]triazolo[4,5-d]pyrimidin-2-yl]-1-(3-chloro-phenyl)-ethanone;

2-[5-tert-Butyl-7-(3,3-difluoro-pyrrolidin-1-yl)-[1,2,3]triazolo[4,5-d]pyrimidin-2-yl]-1-(4-chloro-phenyl)-ethanone;

2-[5-tert-Butyl-7-(3,3-difluoro-pyrrolidin-1-yl)-[1,2,3]triazolo[4,5-d]pyrimidin-2-yl]-1-pyridin-3-yl-ethanone;

5-tert-Butyl-7-(3,3-difluoro-pyrrolidin-1-yl)-2-(2,3,6-trichloro-benzyl)-2H-[1,2,3]triazolo[4,5-d]pyrimidine;

5-tert-Butyl-2-(2-chloro-3-trifluoromethyl-benzyl)-7-(3,3-difluoro-pyrrolidin-1-yl)-2H-[1,2,3]triazolo[4,5-d]pyrimidine;

5-tert-Butyl-2-(2-chloro-6-fluoro-3-methoxy-benzyl)-7-(3,3-difluoro-pyrrolidin-1-yl)-2H-[1,2,3]triazolo[4,5-d]pyrimidine;

5-tert-Butyl-7-(3,3-difluoro-pyrrolidin-1-yl)-2-(2-pyridin-3-yl-ethyl)-2H-[1,2,3]triazolo[4,5-d]pyrimidine;

5-tert-Butyl-7-(3,3-difluoro-pyrrolidin-1-yl)-2-(2-pyridin-4-yl-ethyl)-2H-[1,2,3]triazolo[4,5-d]pyrimidine; and 5-tert-Butyl-2-(2,3-dichloro-6-trifluoromethyl-benzyl)-7-(3,3-difluoro-pyrrolidin-1-yl)-2H-[1,2,3]triazolo[4,5-d]pyrimidine.

5. A compound selected from the group consisting of 5-tert-Butyl-2-(3,4-dichloro-pyridin-2-ylmethyl)-7-(3,3-difluoro-pyrrolidin-1-yl)-2H-[1,2,3]triazolo[4,5-d]pyrimidine;

5-tert-Butyl-7-(3,3-difluoro-pyrrolidin-1-yl)-2-(1,1-dioxo-1λ6-thietan-3-yl)-2H-[1,2,3]triazolo[4,5-d]pyrimidine;

5-tert-Butyl-7-(3,3-difluoro-pyrrolidin-1-yl)-2-(1,1-dioxo-tetrahydro-1λ6-thiophen-3-yl)-2H-[1,2,3]triazolo[4,5-d]pyrimidine;

2-[5-tert-Butyl-7-(3,3-difluoro-pyrrolidin-1-yl)-[1,2,3]triazolo[4,5-d]pyrimidin-2-yl]-1-pyridin-2-yl-ethanone;

5-tert-Butyl-7-(3,3-difluoro-pyrrolidin-1-yl)-2-(5-methyl-[1,3,4]oxadiazol-2-ylmethyl)-2H-[1,2,3]triazolo[4,5-d]pyrimidine;

5-tert-Butyl-2-(3-chloro-pyridin-4-ylmethyl)-7-(3,3-difluoro-pyrrolidin-1-yl)-2H-[1,2,3]triazolo[4,5-d]pyrimidine;

5-tert-Butyl-7-(3,3-difluoro-pyrrolidin-1-yl)-2-(5-methyl-[1,2,4]oxadiazol-3-ylmethyl)-2H-[1,2,3]triazolo[4,5-d]pyrimidine;

5-tert-Butyl-7-(3,3-difluoro-pyrrolidin-1-yl)-2-(1-methyl-1H-tetrazol-5-ylmethyl)-2H-[1,2,3]triazolo[4,5-d]pyrimidine;

5-tert-Butyl-7-(3,3-difluoro-pyrrolidin-1-yl)-2-(2-methyl-2H-[1,2,4]triazol-3-ylmethyl)-2H-[1,2,3]triazolo[4,5-d]pyrimidine;

5-tert-Butyl-7-(3,3-difluoro-pyrrolidin-1-yl)-2-(5-methanesulfonyl-4-methyl-4H-[1,2,4]triazol-3-ylmethyl)-2H-[1,2,3]triazolo[4,5-d]pyrimidine;

{3-[5-tert-Butyl-7-(3,3-difluoro-pyrrolidin-1-yl)-[1,2,3]triazolo[4,5-d]pyrimidin-2-ylmethyl]-5-chloro-pyridin-4-yl}-dimethyl-amine;

5-tert-Butyl-7-(3,3-difluoro-pyrrolidin-1-yl)-2-(3-trifluoromethyl-1H-pyrazol-4-ylmethyl)-2H-[1,2,3]triazolo[4,5-d]pyrimidine;

(S)-1-[5-tert-Butyl-2-(4-methyl-furazan-3-ylmethyl)-2H-[1,2,3]triazolo[4,5-d]pyrimidin-7-yl]-pyrrolidin-3-ol;

(S)-1-[5-tert-Butyl-2-(3-methyl-[1,2,4]oxadiazol-5-ylmethyl)-2H-[1,2,3]triazolo[4,5-d]pyrimidin-7-yl]-pyrrolidin-3-ol; and (S)-1-[5-tert-Butyl-2-(3-chloro-pyridin-2-ylmethyl)-2H-[1,2,3]triazolo[4,5-d]pyrimidin-7-yl]-pyrrolidin-3-ol.

6. A compound selected from the group consisting of (S)-1-[5-tert-Butyl-2-(3,6-dichloro-pyridin-2-ylmethyl)-2H-[1,2,3]triazolo[4,5-d]pyrimidin-7-yl]-pyrrolidin-3-ol;

(S)-1-[5-tert-Butyl-2-(2-chloro-pyridin-3-ylmethyl)-2H-[1,2,3]triazolo[4,5-d]pyrimidin-7-yl]-pyrrolidin-3-ol;

(S)-1-[5-tert-Butyl-2-(2,3-dichloro-benzyl)-2H-[1,2,3]triazolo[4,5-d]pyrimidin-7-yl]-pyrrolidin-3-ol;

(S)-1-[5-tert-Butyl-2-(2-trifluoromethyl-benzyl)-2H-[1,2,3]triazolo[4,5-d]pyrimidin-7-yl]-pyrrolidin-3-ol;

(S)-1-[5-tert-Butyl-2-(2-methanesulfonyl-benzyl)-2H-[1,2,3]triazolo[4,5-d]pyrimidin-7-yl]-pyrrolidin-3-ol;

5-tert-Butyl-7-(3,3-difluoro-pyrrolidin-1-yl)-2-(2,5-dimethyl-2H-pyrazol-3-ylmethyl)-2H-[1,2,3]triazolo[4,5-d]pyrimidine;

5-tert-Butyl-7-(3,3-difluoro-pyrrolidin-1-yl)-2-(3-methyl-3H-[1,2,3]triazol-4-ylmethyl)-2H-[1,2,3]triazolo[4,5-d]pyrimidine;

5-tert-Butyl-7-(3,3-difluoro-pyrrolidin-1-yl)-2-(4,5-dimethyl-4H-[1,2,4]triazol-3-ylmethyl)-2H-[1,2,3]triazolo[4,5-d]pyrimidine;

5-tert-Butyl-7-(3,3-difluoro-pyrrolidin-1-yl)-2-(2-methyl-1-oxy-pyridin-3-ylmethyl)-2H-[1,2,3]triazolo[4,5-d]pyrimidine;

(S)-1-[5-tert-Butyl-2-(3,4-dichloro-pyridin-2-ylmethyl)-2H-[1,2,3]triazolo[4,5-d]pyrimidine-7-yl]-pyrrolidin-3-ol;

(S)-1-[5-tert-Butyl-2-(5-methyl-[1,2,4]oxadiazol-3-ylmethyl)-2H-[1,2,3]triazolo[4,5-d]pyrimidin-7-yl]-pyrrolidin-3-ol;

(S)-1-[5-tert-Butyl-2-(5-methyl-[1,3,4]oxadiazol-2-ylmethyl)-2H-[1,2,3]triazolo[4,5-d]pyrimidin-7-yl]-pyrrolidin-3-al;

(S)-1-[5-tert-Butyl-2-(1-methyl-1H-tetrazol-5-ylmethyl)-2H-[1,2,3]triazolo[4,5-d]pyrimidin-7-yl]-pyrrolidin-3-ol;

(S)-1-[5-tert-Butyl-2-(2-methyl-2H-[1,2,4]triazol-3-ylmethyl)-2H-[1,2,3]triazolo[4,5-d]pyrimidin-7-yl]-pyrrolidin-3-ol; and (S)-1-[5-tert-Butyl-2-(3-methyl-3H-[1,2,3]triazol-4-ylmethyl)-2H-[1,2,3]triazolo[4,5-d]pyrimidin-7-yl]-pyrrolidin-3-ol.

7. A compound selected from the group consisting of (S)-1-[5-tert-Butyl-2-(2,5-dimethyl-2H-pyrazol-3-ylmethyl)-2H-[1,2,3]triazolo[4,5-d]pyrimidin-7-yl]-pyrrolidin-3-ol;

5-tert-Butyl-2-(1-cyclopropyl-1H-tetrazol-5-ylmethyl)-7-(3,3-difluoro-pyrrolidin-1-yl)-2H-[1,2,3]triazolo[4,5-d]pyrimidine;

(S)-1-{5-tert-Butyl-2-[2-(7-nitro-benzo[1,2,5]oxadiazol-4-ylamino)-pyridin-3-ylmethyl]-2H-[1,2,3]triazolo[4,5-d]pyrimidin-7-yl}-pyrrolidin-3-ol;

(S)-1-[5-tert-Butyl-2-(1-cyclopropyl-1H-tetrazol-5-ylmethyl)-2H-[1,2,3]triazolo[4,5-d]pyrimidin-7-yl]-pyrrolidin-3-ol;

(S)-1-[5-tert-Butyl-2-(2,5-dimethyl-2H-[1,2,4]triazol-3-ylmethyl)-2H-[1,2,3]triazolo[4,5-d]pyrimidin-7-yl]-pyrrolidin-3-ol;

5-tert-Butyl-7-(3,3-difluoro-pyrrolidin-1-yl)-2-(2,5-dimethyl-2H-[1,2,4]triazol-3-ylmethyl)-2H-[1,2,3]triazolo[4,5-d]pyrimidine;

(2S,3S)-1-[5-tert-Butyl-2-(1-cyclopropyl-1H-tetrazol-5-ylmethyl)-2H-[1,2,3]triazolo[4,5-d]pyrimidin-7-yl]-2-hydroxymethyl-pyrrolidin-3-ol;

(2S,3S)-1-[5-tert-Butyl-2-(4-methyl-furazan-3-ylmethyl)-2H-[1,2,3]triazolo[4,5-d]pyrimidin-7-yl]-2-hydroxymethyl-pyrrolidin-3-al;

5-tert-Butyl-2-(4-methyl-furazan-3-ylmethyl)-7-(3,3,4,4-tetrafluoro-pyrrolidin-1-yl)-2H-[1,2,3]triazolo[4,5-d]pyrimidine;

5-tert-Butyl-2-(3-methyl-[1,2,4]oxadiazol-5-ylmethyl)-7-(3,3,4,4-tetrafluoro-pyrrolidin-1-yl)-2H-[1,2,3]triazolo[4,5-d]pyrimidine;

5-tert-Butyl-2-(5-methyl-[1,3,4]oxadiazol-2-ylmethyl)-7-(3,3,4,4-tetrafluoro-pyrrolidin-1-yl)-2H-[1,2,3]triazolo[4,5-d]pyrimidine;

5-tert-Butyl-2-(1-methyl-1H-tetrazol-5-ylmethyl)-7-(3,3,4,4-tetrafluoro-pyrrolidin-1-yl)-2H-[1,2,3]triazolo[4,5-d]pyrimidine;

5-tert-Butyl-2-(4,5-dimethyl-4H-[1,2,4]triazol-3-ylmethyl)-7-(3,3,4,4-tetrafluoro-pyrrolidin-1-yl)-2H-[1,2,3]triazolo[4,5-d]pyrimidine;

5-tert-Butyl-2-(3-methyl-3H-[1,2,3]triazol-4-ylmethyl)-7-(3,3,4,4-tetrafluoro-pyrrolidin-1-yl)-2H-[1,2,3]triazolo[4,5-d]pyrimidine; and 5-tert-Butyl-2-(1-cyclopropyl-1H-tetrazol-5-ylmethyl)-7-(2-oxa-6-aza-spiro[3.3]hept-6-yl)-2H-[1,2,3]triazolo[4,5-d]pyrimidine.

8. A compound selected from the group consisting of 5-tert-Butyl-2-(4,5-dimethyl-4H-[1,2,4]triazol-3-ylmethyl)-7-(2-oxa-6-aza-spiro[3.3]hept-6-yl)-2H-[1,2,3]triazolo[4,5-d]pyrimidine;

5-tert-Butyl-2-(2-methanesulfonyl-benzyl)-7-(2-oxa-6-aza-spiro[3.3]hept-6-yl)-2H-[1,2,3]triazolo[4,5-d]pyrimidine;

5-tert-Butyl-2-(3-chloro-pyridin-2-ylmethyl)-7-(2-oxa-6-aza-spiro[3.3]hept-6-yl)-2H-[1,2,3]triazolo[4,5-d]pyrimidine;

(S)-1-[2-(2-Chloro-benzyl)-5-(2,2,2-trifluoro-ethoxy)-2H-[1,2,3]triazolo[4,5-d]pyrimidin-7-yl]-pyrrolidin-3-ol;

(S)-1-[5-(2,2,2-Trifluoro-ethoxy)-2-(2-trifluoromethyl-benzyl)-2H-[1,2,3]triazolo[4,5-d]pyrimidin-7-yl]-pyrrolidin-3-ol;

(S)-1-[2-(2-Chloro-benzyl)-5-isopropoxy-2H-[1,2,3]triazolo[4,5-d]pyrimidin-7-yl]-pyrrolidin-3-ol;

7-(3,3-Difluoro-pyrrolidin-1-yl)-5-(2,2-dimethyl-propoxy)-2-(1-methyl-1H-tetrazol-5-ylmethyl)-2H-[1,2,3]triazolo[4,5-d]pyrimidine;

(R)-1-[5-tert-Butyl-2-(1-methyl-1H-tetrazol-5-ylmethyl)-2H-[1,2,3]triazolo[4,5-d]pyrimidin-7-yl]-pyrrolidin-3-ol;

1-[5-tert-Butyl-2-(1-methyl-1H-tetrazol-5-ylmethyl)-2H-[1,2,3]triazolo[4,5-d]pyrimidin-7-yl]-pyrrolidin-3-ol;

7-(3,3-Difluoro-pyrrolidin-1-yl)-2-(2-trifluoromethyl-benzyl)-5-((S)-2,2,2-trifluoro-1-methyl-ethoxy)-2H-[1,2,3]triazolo[4,5-d]pyrimidine;

7-(3,3-Difluoro-pyrrolidin-1-yl)-2-(2-methanesulfonyl-benzyl)-5-((S)-2,2,2-trifluoro-1-methyl-ethoxy)-2H-[1,2,3]triazolo[4,5-d]pyrimidine;

2-(3-Chloro-pyridin-2-ylmethyl)-7-(3,3-difluoro-pyrrolidin-1-yl)-5-((S)-2,2,2-trifluoro-1-methyl-ethoxy)-2H-[1,2,3]triazolo[4,5-d]pyrimidine;

7-(3,3-Difluoro-pyrrolidin-1-yl)-2-(5-methyl-[1,3,4]oxadiazol-2-ylmethyl)-5-((S)-2,2,2-trifluoro-1-methyl-ethoxy)-2H-[1,2,3]triazolo[4,5-d]pyrimidine;

7-(3,3-Difluoro-pyrrolidin-1-yl)-2-(3-methyl-[1,2,4]oxadiazol-5-ylmethyl)-5-((S)-2,2,2-trifluoro-1-methyl-ethoxy)-2H-[1,2,3]triazolo[4,5-d]pyrimidine; and 7-(3,3-Difluoro-pyrrolidin-1-yl)-2-(1-methyl-1H-tetrazol-5-ylmethyl)-5-((S)-2,2,2-trifluoro-1-methyl-ethoxy)-2H-[1,2,3]triazolo[4,5-d]pyrimidine.

9. A compound selected from the group consisting of 7-(3,3-Difluoro-pyrrolidin-1-yl)-2-(4-methyl-furazan-3-ylmethyl)-5-((S)-2,2,2-trifluoro-1-methyl-ethoxy)-2H-[1,2,3]triazolo[4,5-d]pyrimidine;

7-(3,3-Difluoro-pyrrolidin-1-yl)-5-((S)-2,2,2-trifluoro-1-methyl-ethoxy)-2-(3,3,3-trifluoro-propyl)-2H-[1,2,3]triazolo[4,5-d]pyrimidine;

2-(1-Cyclopropyl-1H-tetrazol-5-ylmethyl)-7-(3,3-difluoro-pyrrolidin-1-yl)-5-((S)-2,2,2-trifluoro-1-methyl-ethoxy)-2H-[1,2,3]triazolo[4,5-d]pyrimidine;

(S)-1-[5-tert-Butyl-2-(2-chloro-benzyl)-2H-[1,2,3]triazolo[4,5-d]pyrimidin-7-yl]-3-methyl-pyrrolidin-3-ol;

(R)-1-[5-tert-Butyl-2-(2-chloro-benzyl)-2H-[1,2,3]triazolo[4,5-d]pyrimidin-7-yl]-3-methyl-pyrrolidin-3-ol;

(S)-1-[5-tert-Butyl-2-(2-trifluoromethyl-benzyl)-2H-[1,2,3]triazolo[4,5-d]pyrimidin-7-yl]-3-methyl-pyrrolidin-3-ol;

(R)-1-[5-tert-Butyl-2-(2-trifluoromethyl-benzyl)-2H-[1,2,3]triazolo[4,5-d]pyrimidin-7-yl]-3-methyl-pyrrolidin-3-ol;

(S)-1-[5-tert-Butyl-2-(2-methanesulfonyl-benzyl)-2H-[1,2,3]triazolo[4,5-d]pyrimidin-7-yl]-3-methyl-pyrrolidin-3-ol;

(R)-1-[5-tert-Butyl-2-(2-methanesulfonyl-benzyl)-2H-[1,2,3]triazolo[4,5-d]pyrimidin-7-yl]-3-methyl-pyrrolidin-3-ol;

(S)-1-[5-tert-Butyl-2-(3-chloro-pyridin-2-ylmethyl)-2H-[1,2,3]triazolo[4,5-d]pyrimidin-7-yl]-3-methyl-pyrrolidin-3-ol;

(R)-1-[5-tert-Butyl-2-(3-chloro-pyridin-2-ylmethyl)-2H-[1,2,3]triazolo[4,5-d]pyrimidin-7-yl]-3-methyl-pyrrolidin-3-ol;

(S)-1-[5-tert-Butyl-2-(5-methyl-[1,3,4]oxadiazol-2-ylmethyl)-2H-[1,2,3]triazolo[4,5-d]pyrimidin-7-yl]-3-methyl-pyrrolidin-3-ol;

(R)-1-[5-tert-Butyl-2-(5-methyl-[1,3,4]oxadiazol-2-ylmethyl)-2H-[1,2,3]triazolo[4,5-d]pyrimidin-7-yl]-3-methyl-pyrrolidin-3-ol;
(S)-1-[5-tert-Butyl-2-(3-methyl-[1,2,4]oxadiazol-5-ylmethyl)-2H-[1,2,3]triazolo[4,5-d]pyrimidin-7-yl]-3-methyl-pyrrolidin-3-ol; and
(R)-1-[5-tert-Butyl-2-(3-methyl-[1,2,4]oxadiazol-5-ylmethyl)-2H-[1,2,3]triazolo[4,5-d]pyrimidin-7-yl]-3-methyl-pyrrolidin-3-ol.

10. A compound selected from the group consisting of
(S)-1-[5-tert-Butyl-2-(1-methyl-1H-tetrazol-5-ylmethyl)-2H-[1,2,3]triazolo[4,5-d]pyrimidin-7-yl]-3-methyl-pyrrolidin-3-ol;
(R)-1-[5-tert-Butyl-2-(1-methyl-1H-tetrazol-5-ylmethyl)-2H-[1,2,3]triazolo[4,5-d]pyrimidin-7-yl]-3-methyl-pyrrolidin-3-ol;
(S)-1-[5-tert-Butyl-2-(4-methyl-furazan-3-ylmethyl)-2H-[1,2,3]triazolo[4,5-d]pyrimidin-7-yl]-3-methyl-pyrrolidin-3-ol;
(R)-1-[5-tert-Butyl-2-(4-methyl-furazan-3-ylmethyl)-2H-[1,2,3]triazolo[4,5-d]pyrimidin-7-yl]-3-methyl-pyrrolidin-3-ol;
(S)-1-[5-tert-Butyl-2-(3,3,3-trifluoro-propyl)-2H-[1,2,3]triazolo[4,5-d]pyrimidin-7-yl]-3-methyl-pyrrolidin-3-ol;
(R)-1-[5-tert-Butyl-2-(3,3,3-trifluoro-propyl)-2H-[1,2,3]triazolo[4,5-d]pyrimidin-7-yl]-3-methyl-pyrrolidin-3-ol;
(S)-1-[5-tert-Butyl-2-(1-cyclopropyl-1H-tetrazol-5-ylmethyl)-2H-[1,2,3]triazolo[4,5-d]pyrimidin-7-yl]-3-methyl-pyrrolidin-3-ol;
(R)-1-[5-tert-Butyl-2-(1-cyclopropyl-1H-tetrazol-5-ylmethyl)-2H-[1,2,3]triazolo[4,5-d]pyrimidin-7-yl]-3-methyl-pyrrolidin-3-ol;
N—{(S)-1-[2-(2-Chloro-benzyl)-5-(2,2-dimethyl-propoxy)-2H-[1,2,3]triazolo[4,5-d]pyrimidin-7-yl]-pyrrolidin-3-yl}-acetamide;
N—{(S)-1-[2-(3-Chloro-pyridin-2-ylmethyl)-5-(2,2-dimethyl-propoxy)-2H-[1,2,3]triazolo[4,5-d]pyrimidin-7-yl]-pyrrolidin-3-yl}-acetamide;
tert-Butyl-[7-(3,3-difluoro-pyrrolidin-1-yl)-2-(2-trifluoromethyl-benzyl)-2H-[1,2,3]triazolo[4,5-d]pyrimidin-5-yl]-amine;
tert-Butyl-[7-(3,3-difluoro-pyrrolidin-1-yl)-2-(2-methanesulfonyl-benzyl)-2H-[1,2,3]triazolo[4,5-d]pyrimidin-5-yl]-amine;
tert-Butyl-[2-(3-chloro-pyridin-2-ylmethyl)-7-(3,3-difluoro-pyrrolidin-1-yl)-2H-[1,2,3]triazolo[4,5-d]pyrimidin-5-yl]-amine;
tert-Butyl-[7-(3,3-difluoro-pyrrolidin-1-yl)-2-(1-methyl-1H-tetrazol-5-ylmethyl)-2H-[1,2,3]triazolo[4,5-d]pyrimidin-5-yl]-amine; and
tert-Butyl-[7-(3,3-difluoro-pyrrolidin-1-yl)-2-(4-methyl-furazan-3-ylmethyl)-2H-[1,2,3]triazolo[4,5-d]pyrimidin-5-yl]-amine.

11. A compound selected from the group consisting of
N—{(S)-1-[2-(2-Chloro-benzyl)-5-((S)-2,2,2-trifluoro-1-methyl-ethoxy)-2H-[1,2,3]triazolo[4,5-d]pyrimidin-7-yl]-pyrrolidin-3-yl}-acetamide;
N—{(S)-1-[2-(2-Trifluoromethyl-benzyl)-5-((S)-2,2,2-trifluoro-1-methyl-ethoxy)-2H-[1,2,3]triazolo[4,5-d]pyrimidin-7-yl]-pyrrolidin-3-yl}-acetamide;
N—{(S)-1-[2-(2-Methanesulfonyl-benzyl)-5-((S)-2,2,2-trifluoro-1-methyl-ethoxy)-2H-[1,2,3]triazolo[4,5-d]pyrimidin-7-yl]-pyrrolidin-3-yl}-acetamide;
N—{(S)-1-[5-tert-Butylamino-2-(2-chloro-benzyl)-2H-[1,2,3]triazolo[4,5-d]pyrimidin-7-yl]-pyrrolidin-3-yl}-acetamide; and
(S)-1-[5-tert-Butylamino-2-(1-methyl-1H-tetrazol-5-ylmethyl)-2H-[1,2,3]triazolo[4,5-d]pyrimidin-7-yl]-pyrrolidin-3-ol.

12. A compound selected from the group consisting of
5-tert-Butyl-2-(2-chloro-benzyl)-7-morpholin-4-yl-2H-[1,2,3]triazolo[4,5-d]pyrimidine;
5-tert-Butyl-2-cyclohexylmethyl-7-(3,3-difluoro-pyrrolidin-1-yl)-2H-[1,2,3]triazolo[4,5-d]pyrimidine;
5-tert-Butyl-7-(3,3-difluoro-pyrrolidin-1-yl)-2-pyridin-4-ylmethyl-2H-[1,2,3]triazolo[4,5-d]pyrimidine;
5-tert-Butyl-7-(3,3-difluoro-pyrrolidin-1-yl)-2-(2,2,2-trifluoro-ethyl)-2H-[1,2,3]triazolo[4,5-d]pyrimidine;
2-(2-Bromo-benzyl)-5-tert-butyl-7-(3,3-difluoro-pyrrolidin-1-yl)-2H-[1,2,3]triazolo[4,5-d]pyrimidine;
2-[5-tert-Butyl-7-(3,3-difluoro-pyrrolidin-1-yl)-[1,2,3]triazolo[4,5-d]pyrimidin-2-ylmethyl]-benzonitrile;
5-tert-Butyl-7-(3,3-difluoro-pyrrolidin-1-yl)-2-phenethyl-2H-[1,2,3]triazolo[4,5-d]pyrimidine;
5-tert-Butyl-2-[(R)-1-(2-chloro-phenyl)-ethyl]-7-(3,3-difluoro-pyrrolidin-1-yl)-2H-[1,2,3]triazolo[4,5-d]pyrimidine;
5-tert-Butyl-2-(4-chloro-pyridin-3-ylmethyl)-7-(3,3-difluoro-pyrrolidin-1-yl)-2H-[1,2,3]triazolo[4,5-d]pyrimidine;
5-tert-Butyl-2-(3-chloro-pyridin-2-ylmethyl)-7-(3,3-difluoro-pyrrolidin-1-yl)-2H-[1,2,3]triazolo[4,5-d]pyrimidine;
5-tert-Butyl-7-(3,3-difluoro-pyrrolidin-1-yl)-2-(4-methyl-furazan-3-ylmethyl)-2H-[1,2,3]triazolo[4,5-d]pyrimidine;
5-tert-Butyl-2-(3-chloro-pyridin-4-ylmethyl)-7-(3,3-difluoro-pyrrolidin-1-yl)-2H-[1,2,3]triazolo[4,5-d]pyrimidine; and
(S)-1-[5-tert-Butyl-2-(2-trifluoromethyl-benzyl)-2H-[1,2,3]triazolo[4,5-d]pyrimidin-7-yl]-pyrrolidin-3-ol.

13. A pharmaceutical composition comprising the compound according to any one of claims 1, 2, 3, 4, 5, 6, 7, 8, 9, 10, 11 or 12 and a therapeutically inert carrier.

* * * * *